(12) United States Patent
Spiegel et al.

(10) Patent No.: US 11,737,992 B2
(45) Date of Patent: *Aug. 29, 2023

(54) SPHINGOSINE KINASE TYPE 1 INHIBITORS AND USES THEREOF

(71) Applicants: Enzo Therapeutics, Inc., Farmingdale, NY (US); Virginia Commonwealth University, Richmond, VA (US)

(72) Inventors: Sarah Spiegel, Richmond, VA (US); Robert Elliot Zipkin, Wynnewood, PA (US); Jeffrey Kroll Adams, Fort Washington, PA (US)

(73) Assignees: ENZO THERAPEUTICS, INC., Farmingdale, NY (US); VIRGINIA COMMONWEALTH UNIVERSITY, Richmond, VA (US)

(*) Notice: Subject to any disclaimer, the term of this patent is extended or adjusted under 35 U.S.C. 154(b) by 211 days.

This patent is subject to a terminal disclaimer.

(21) Appl. No.: 17/169,662

(22) Filed: Feb. 8, 2021

(65) Prior Publication Data
US 2021/0177776 A1    Jun. 17, 2021

Related U.S. Application Data

(60) Continuation of application No. 16/813,961, filed on Mar. 10, 2020, now Pat. No. 10,945,971, which is a continuation of application No. 16/572,699, filed on Sep. 17, 2019, now Pat. No. 10,624,863, which is a continuation of application No. 16/199,337, filed on Nov. 26, 2018, now Pat. No. 10,456,370, which is a continuation of application No. 15/954,131, filed on Apr. 16, 2018, now Pat. No. 10,166,204, which is a continuation of application No. 15/181,826, filed on Jun. 14, 2016, now Pat. No. 9,974,758, which is a continuation of application No. 13/649,221, filed on Oct. 11, 2012, now Pat. No. 9,388,121, which is a division of application No. 12/584,131, filed on Aug. 31, 2009, now Pat. No. 8,314,151, which is a continuation-in-part of application No. 12/387,228, filed on Apr. 29, 2009, now Pat. No. 8,372,888.

(60) Provisional application No. 61/048,638, filed on Apr. 29, 2008.

(51) Int. Cl.
| | | |
|---|---|---|
| A61K 31/135 | (2006.01) |
| A61P 25/04 | (2006.01) |
| A61P 11/06 | (2006.01) |
| A61K 31/40 | (2006.01) |
| C07C 323/32 | (2006.01) |
| C07D 263/06 | (2006.01) |
| C07D 295/092 | (2006.01) |
| C07C 215/28 | (2006.01) |
| C07C 217/64 | (2006.01) |
| C07C 233/18 | (2006.01) |

(52) U.S. Cl.
CPC .......... *A61K 31/135* (2013.01); *A61K 31/40* (2013.01); *A61P 11/06* (2018.01); *A61P 25/04* (2018.01); *C07C 215/28* (2013.01); *C07C 217/64* (2013.01); *C07C 233/18* (2013.01); *C07C 323/32* (2013.01); *C07D 263/06* (2013.01); *C07D 295/092* (2013.01)

(58) Field of Classification Search
CPC ...... A61K 31/133; A61K 31/135; A61P 25/04
See application file for complete search history.

(56) References Cited

U.S. PATENT DOCUMENTS

| | | | |
|---|---|---|---|
| 2,868,844 A | 1/1959 | Coffield et al. |
| 3,871,958 A | 3/1975 | Nakazawa et al. |
| 4,707,440 A | 11/1987 | Stavrianopoulos et al. |
| 6,372,800 B1 | 4/2002 | Fujita et al. |
| 8,314,151 B2 | 11/2012 | Spiegel et al. |
| 8,372,888 B2 | 2/2013 | Zipkin et al. |
| 9,388,121 B2 | 7/2016 | Spiegel et al. |
| 9,974,758 B2 | 5/2018 | Spiegel et al. |
| 10,166,204 B2 | 1/2019 | Spiegel et al. |
| 10,456,370 B2 | 10/2019 | Spiegel et al. |
| 2004/0203104 A1 | 10/2004 | Spiegel et al. |
| 2006/0270630 A1 | 11/2006 | Smith et al. |
| 2007/0196493 A1 | 8/2007 | Kinski et al. |
| 2007/0275908 A1 | 11/2007 | Defrees et al. |
| 2008/0145883 A1 | 6/2008 | Baumruker et al. |
| 2008/0167352 A1 | 7/2008 | Smith et al. |
| 2010/0056762 A1 | 3/2010 | Old |
| 2010/0233121 A1 | 9/2010 | Frohna |

FOREIGN PATENT DOCUMENTS

WO    WO2006/004359    1/2006

OTHER PUBLICATIONS

Adamson et al., "Glioblastoma multiforme: a review of where we have been and where we are going," *Expert Opin. Investig. Drugs*, vol. 18, No. 8, pp. 1061-1083 (2009).
Amarente-Mendes, et al., "Bcr-Abl exerts its antiapoptotic effect against diverse apoptotic stimuli through blockage of mitochondrial release of cytochrome C and activation of caspase3," *Blood*, vol. 91, pp. 1700-1705 (1998).
Bektas et al., "A spingosine kinase inhibitor induces cell death in temoxolomide resistant gliobastoma cells," *Cancer Chemotherapy and Pharmacology*, vol. 64, No. 5, pp. 1053-1058 (2009).
Berdyshev et al., "De novo biosynthesis of dihydrosphingosine-1-phosphate by sphingosine kinase 1 in mammalian cells," *Cellular Signaling*, vol. 18, p. 1779-1792 (2006).
Berge et al., "Pharmaceutical Salts," *Journal of Pharmaceutical Sciences*, vol. 66, No. 1, pp. 1-19 (1977).
Bernal et al., A Novel Activation Pathway for Thrombin-Dependent Induction of the Chemokine MCP-1 from Endothelial Cells., Session Type 110-III, XP-002376618, one page, 2003.

(Continued)

*Primary Examiner* — Theodore R. Howell
(74) *Attorney, Agent, or Firm* — Quarles & Brady LLP

(57) ABSTRACT

Provided are inhibitors of sphingosine kinase Type I that are useful in the treatment of neuropathic pain.

10 Claims, 19 Drawing Sheets

Specification includes a Sequence Listing.

(56) References Cited

OTHER PUBLICATIONS

Betito et al., "Reguation by sphingosine-1-phosphate of Bax and Bad activities during apoptosis in a MEK-dependent manner," *Biochem. Biophys. Res. Common.*, vol. 340, pp. 1273-1277 (2006).
Brinkman, Volker, "Sphingosine 1-phosphate receptors in health and disease: mechanistic insights from gene deletion studies and reverse pharmacology," *Pharmcool Ther.*, vol. 115, pp. 85-105 (2007).
Chandrasekhar et al., "Practical and highly stereoselective approaches to the total synthesis of (−)codonopsinine," *Tetrahedron: Asymmetry*, vol. 17, pp. 1380-1386 (2006).
Chen et al., "Inflammation Triggers Production of Dimethylsphingosine from Oligodendrocytes," Neuroscience, vol. 279, pp. 113-121 (2014).
Cheng et al., "Conversion of Bcl-2 to a Bax-like death effector by caspases," *Science*, vol. 278, pp. 1966-1968 (1997).
Cuvillier et al., "Involvement of sphingosine in mitochondria-dependent Fas-induced apoptosis of Type II Jurkat T cells," *JBC*, vol. 275, pp. 15691-15700 (2000).
Dai et al., "Pharmacological inhibitors of the mitogen-activated protein kinase (MAPK) kinase/MAPK cascade interact synergisticall with UCN-02 to induce mitochondrial dysfunction and apoptosis in human leukemia cells," *Cancer Res.*, vol. 61, pp. 5106-5115 (2001).
De Jonghe et al., "Structure-activity relationship of short chain sphingoid bases as inhibitors of sphingosine kinase," *Biorg. Med. Chem. Lett.*, vol. 9, pp. 3175-3180 (1999).
De Luca et al., "NAD+/NADH as/or CoQ/CoQH2 rations form palsma membrane electron transport may determine ceramide and sphingosine-1-phosphate levels accompanying G1 arrest and apoptosis," *Biofactors*, vol. 25, pp. 43-60 (2005).
DelGado et al., "Inhibitors of sphingolipid metabolism enzymes," *biochmica et biophysica acta*, vol. 1758, No. 12, pp. 1957-1977 (2006).
Edsall et al., "N,N-dimethylsphingosine is a potent competitive inhibitor of sphingosine kinase but not of protein kinase C: modulation of cellular levels of sphingosine 1-phosphate and ceramide," *Biochemistry*, vol. 37, pp. 12892-12898 (1998).
Freeman (ed.), "Cancer Principles & Practice of Oncology," 6th Ed., Lippincott Williams & Wilkins (Philadelphia, PA), pp. 2119-2120 (2001).
French et al., "Discovery and evaluation of inhibitors of human sphingosine kinase," *Cancer Res.*, vol. 63, pp. 5962-5969 (2003).
French et al., "Pharmacology and Antitumor Activity of ABC294640, a Selective Inhibitor of Sphingosine Kinase-2," The Journal of Pharmacology and Experimental Therapeutics, vol. 333, No. 1, pp. 129-139 (2010).
Gamble et al., "Phenoxodiol, an experimental anticancer drug, shows potent antiangiogenic properties in addition to its antitumour effects," *Int. J. Cancer*, vol. 118, pp. 2412-2420 (2006).
Gokel et al., Israel J. Chem., (CAPLUS Abstract), vol. 32, pp. 127-133 (1992).
Guo et al., A Prototype Intelligent Hybrid System for Hard Gelatin Capsule Formulation Development, *Pharmaceutical Technology*, pp. 44-60 (2002).
Hamada et al., "Involvement of Mac-1-mediated adherence and sp=phingosine 1-phosphate insurvival of phorbol ester-treated U937 cells," *Boichem Biophys. Res. Commun.*, vol. 244, pp. 745-750 (1998).
Igarashi et al., "Effect of chemically well-defined sphingosine and its N-methyl derivatives on proteinkinase C and src kinase activities," *Biochemistry*, vol. 28, pp. 6796-6800 (1989).
International Search Report for priority application PCT/US2010/32939 (2 pages).
Jarvis et al., Coordinate regulation of stress- and mitogen-activated protein kinases in the apoptotic actions of ceramide and sphoingosine, *Mol. Pharmacol.*, vol. 52, pp. 935-947 (1997).
Jarvis et al., "Induction of apoptotic DNA damage and cell damage and cell death by activation of the sphingomyelin pathway," *PNAS USA*, vol. 91, pp. 73-77 (1994).

Jeremias et al., "Cell death induction by betulnic acid ceramide and TRAIL inprimary globlastoma multiforme cells," *ACTA Neurochirurgica*, vol. 148, No. 7, pp. 721-729 (2004).
Johnson et al., "Intrinsic cytotoxicity and chemomodulatory actions aof novel phenethyllsothiocynate sphingoid base derivatives in HL-60 human promyelocytic leukemia cells," *J. Pharmacol. Exp. Therap.*, vol. 309, pp. 452-461 (2004).
Kapitonov et al., "Targeting Sphingosine Kinase 1 inhibits Akt Signaling, Induces Apoptosis, and Suppresses Growth of Human Glioblastoma Cells and Xenografts," *Cancer Research*, vol. 69, No. 17, pp. 6915-6923 (2009).
Kawamori et al., "Spingosine kinase 1 is up-regulated in colon carcinogenesis," *The FASEB Journal*, vol. 20, No. 2, pp. 386—(2005).
Kim et al., "Isoflurane Protects Human Kidney Proximal Tubule Cells against Necrosis via Sphingosine Kinase and Sphingosine-1-Phosphate Generation," American Journal of Nephrology, vol. 31, No. 4, pp. 353-362 (2010).
Kim et al., "Sphingosine 1-phosphate (S1P) induces shape change in rat C6 gloma cells through the S1P2 receptor: development of an agonist for S1P receptors," *J. Pharma. Pharmacol.*, vol. 59, pp. 1035-1041 (2007).
Kim et al., "synthesis and Cytotoxicity of New Aromatic Ceramide Analogs with Alkylsulfonamido Chains," *Arch. Pharm. Res.*, vol. 30, No. 5, pp. 570-580 (2007).
Kohno t al., "Intracellular role for sphingosine kinase 1 in intestinal adenoma cell proliferation," *Mol. Cell Biol.*, vol. 26, pp. 7211-7223 (2006).
Li et al., "Sphingosine kinase-1 mediates BCR/ABL-induced upregulation of mci-1 in chronic myeloid leukemia cells," *Onogene*, vol. 26, pp. 7904-7908 (2007).
Liang et al, "Sphingosine-1-Phosphate Links Persistent STAT3 Activation, Chronic Intestinal Inflammation, and Development of Colitis-Associated Cancer," *Cancer Cell*, vol. 23, No. 1, pp. 107-120 (2013).
Lim et al., "Syntheses of sphingosine-1-phosphate analogues and their interaction with EDG/SIP receptors," *Bioorganic & Medicinal Chemistry Letters*, vol. 14, pp. 2499-2503 (2004).
Lynch et al, "Sphingosine 1-phosphate chemical biology," Biochimica et Biophysica Acta, vol. 1781, pp. 508-512 (2008).
Maines et al., "Suppression of Ulcerative Colitis in Mice by Orally Available Inhibitors of Sphingosine Kinase," *Dig. Dis. Sci.*, vol. 53, pp. 997-1012 (2008).
McCormack et al., "Animal models of acute myelogenous leukaemia-development, application and future perspectives," *Leukemia*, vol. 19, pp. 687-706 (2005).
Mitra et al., Role of ABCC1 in export of sphingosine-1-phosphate from mast cells, *PNAS USA*, pp. 16394-16399 (2006).
Moulding et al., "Apoptosis is rapidly triggered by antisense depletion of mci-1 in differentiating U937 cells," *Blood*, vol. 96, pp. 1756-1763 (2000).
Mulzer et al., Chem. Berichte (CAPLUS Abstract), vol. 114, pp. 37-1-24 (1981).
Murakami et al., "Efficient sterodivergent synthesis of erythro- and threo-sphingosines: unprecedented reversal of the stereochemistry in the addition," *Tetrahedron*, vol. 58, pp. 9257-9263 (2002).
Murakami et al., "Synthesis and biological properties of novel sphingosine derivatives,", *Bioorganic & Medicinal Chemistry Letters*, vol. 15, pp. 1115-1119 (2005).
Niedle (Ed.), "Cancer Drug Design and Discovery," Academic Press, pp. 427-431 (2008).
Neviani et al., "FTY720, a new alternative for treating blast crisis chronic myelogenous leukemia nd Philadelphia chromosome-positive acute lymphocytic leukemia," *J. Clin. Invest.*, vol. 117, pp. 24;08-2421 (2007).
Ng et al., "Marked suppression of tumor growth by FTY20 in a rat liver tumor model: the significance of down-regulation of cell suvivall Akt pathway," *Int. J. Oncol.*, vol. 30, pp. 375-380 (2007).
Niiro et al., "(3z)-2-acetylamino-3-octadecen-1-ol as a potent apoptotic agent against HL-60 cells," *biorg. Med. Chem.*, vol. 12, pp. 45-51 (2004).

(56) References Cited

OTHER PUBLICATIONS

Nixon, Graeme F., "Sphingolipids in inflammation: pathological implications and potential therapeutic targets," Journal of Phamacology, vol. 158, pp. 982-993 (2009).
Nyakern et al., Frequent elevation of Akt kinase phosphorylation in blood marrow and peripheral blood mononuclear cells from high-risk myelodysplastic syndrome patients, Leukemia, vol. 20, pp. 230-238 (2006).
Overmeire et al., "Synthesis and biological Evaluation of Ceramide Analogues with Substituted Aromatic Rings or an Allylic Fluoride in the Sphingoid Moiety," J. Med. Chem., vol. 43, pp. 4189-4199 (2000).
Paugh et al., The immunosuppressant FTY720 is phosphorylated by sphingosine kinase type 2, FEBS LETT., vol. 554, pp. 189-193 (2003).
Pettus et al., "The sphingosine kindase 1/sphingosine-1-phosphate pathway mediates COX-2 inductiona nd PGE2 production in response to TNF-α," The FASEB Journal, vol. 17, pp. 1411-1421 (2003).
Pitson et al., "Phosphorylation-dependent translocation of sphingosine kinase to the plasma membrane drives its oncogenic signaling," J. Exp. Med., vol. 201, pp. 49-54 (2005).
Price et al., "A specific sphingosine kinase 1 inhibitor attenuates airway hyperresponsiveness and inflammation in a mast cell-dependent murine model of allergic asthma," J Allergy Clin Immunol, vol. 131, No. 2, pp. 501-511 (2013).
Pyne et al., "Sphigosine 1-Phosphate is a Missing Link between Chronic Inflammation and Colon Cancer," Cancer Cell, vol. 23, pp. 5-7 (2013).
Rosato et al., "Mechanism and functional role of XIAP and Mcl-1 down-regulation in flavopirodo/vorinstat antileukemic intractions," Mol. Cancer Ther. , vol. 6, pp. 692-702 (2007).
Sabbadini, R.A., "Targeting sphinogosine-1-phosphate for cancer therapy," Br. J. Cancer, vol. 95, pp. 1131-1135 (2006).
Sausville et al., "Contributions of Human Tumor Xenografts to Anticancer Drug Development," Cancer Res., vol. 66, No. 7, pp. 3351-3354 (2006).
Singh et al., "Sphingosine-1-phosphate signaling: A novel target for simultaneous adjuvant treatment of triple negative breast cancer and chemotherapy-induced neuropathic pain," Advances in Biological Regulation, vol. 75, 7 pages, (2020).
Snider et al., "A role for sphigosine kinase 1 in dextran sulfate sodium-induced colitis," The FASEB Journal, vol. 23, No. 1, pp. 143-152 (2009).
Sobue et al., "Aunatitative RT-PCR analysis of sphingolipid metabolic enzymes in acute leukemia and myelodysplastic syndromes," Leukemia, vol. 20, pp. 2042-2046 (2006).
Steelman et al., JAK/STAT, Raf/MEK/ERK, P13K/Akt and BCR-ABL in cell cycle progression and leukemogenesis, Leukemia, vol. 18, pp. 189218 (2004).
Suguira et al., "Ceramide kinase, a novel lipid kinase," JBC, vol. 277, pp. 23294-23300 (2002).
Sullards et al., "Analysis of sphingosine 1-phosphate, ceramides and other bioactive sphingolipids by high-performance liquid chromatography-tandem mass spectrometry," Science, STKE, L1 (2001).
Swanton et al., "Regulators of mitotic arrest and ceramide metabolisim are determinants of sensitivity to paclitaxel and other chemotherapeutic drugs," Cancer Cell, vol. 11, pp. 498-512 (2007).
Vernant et al., "The sphingosine kinase 2 inhibitor ABC294640 reduces the growth of prostate cancer cells and results in accumulation of dihydroceramides in vitro and in vivo," Mol Cancer Ther, vol. 14, No. 12, pp. 2744-2752 (2015).
Vernant et al., "The sphingosine kinase 2 inhibitor ABC294640 reduces the growth of prostate cancer cells and results in accumulation of dihydroceramides in vitro and in vivo," Mol Cancer Ther, vol. 14, No. 12, pp. 2744-2762 (2015).
Wang et al., "Activation of the Sphingogsine Kinase-Signaling Pathway by High Glucose Mediates the Proinflammatory Phenotype of Endothelial Cells," Circulation Research, Grune and Stratton, vol. 97, No. 9, pp. 891-899 (2005).
Warunis et al., Berichte der Deutschen Chemischen Gesellscaft (CAPLUS Abstract), vol. 43, pp. 654-660 (1910).
Wolk et al, "The Incidence of Central Nervous System Leukemia in Adults with Acute Leukemia," Cancer, vol. 33, pp. 863-869 (1974).
Zhang et al., "Antinocipceptive effects of FTY720 during trauma-induced neuropathic pain are mediated by spinal S1P receptors," Biol Chem, vol. 396, pp. 783-794 (2015)—Abstract Only.
Zhang et al., "Bci-2 interrupts the ceramide-mediated pathway of cell death," PNAS USA, vol. 93, pp. 5325-5328 (1996).
Zhang et al., "Sphingosine 1-phosphate signaling contributes to cardiac inflammation, dysfunction, and remodeling following myocardial infarction," Am J Physiol Heart Circ Physiol, vol. 310, pp. H250-H261 (2016).
Anelli et al., Sphingosine kinase 1 is up-regulated during hypoxia in U87MG glioma cells, JBC 2008, 3365-3375, 283.
Barthwal et al., Negative regulation of mixed lineage kinase 3 by protein kinase B/AKT leads to cell survival, JBC 2003, 3897-3902, 278.
Coward et al., Safingol (L-threo-sphinganine) induces autophagy in solid tumor cells through inhibition of PKC and the PI3-kinase pathway, Autophagy 2009, 184-193, 5.
Cuvillier et al., Downregulating sphingosine kinase-1 for cancer therapy, Expert. Opin. Ther. Targets 2008, 1009-1020, 12.
Giannini et al., Patient tumor EGFR and PDGFRA gene amplifications retained in an invasive intracranial xenograft model of glioblastoma multiforme, Neuro-Oncology 2005, 164-176, 7.
Giussani et al., Phosphatidylinositol 3-kinase/AKT pathway regulates the endoplasmic reticulum to golgi traffic of ceramide in glioma cells, JBC 2009, 5088-5096, 284.
Haas-Kogan et al., Protein kinase B (PKB/Akt) activity is elevated in glioblastoma cells due to mutation of the tumor suppressor PTEN/MMAC, Current Biology 1998, 1195-1198, 8.
Hannun and Obeid, Principles of bioactive lipid signalling: lessons from sphingolipids, Nature Reviews Molecular Cell Biology 2008, 139-150, 9.
Kim et al., Akt phosphorylates and negatively regulates apoptosis signal-regulating kinase 1, Molecular and Cellular Biology 2001, 893-901, 21.
Kusner et al., The localization and activity of sphingosine kinase 1 are coordinately regulated with actin cytoskeletal dynamics in macrophages, JBC 2007, 23147-23162, 282.
Lepley et al., The G protein-coupled receptor S1P2 regulates Rho/Rho kinase pathway to inhibit tumor cell migration, Cancer Res. 2005, 3788-3795, 65.
Le Scolan et al., Overexpression of sphingosine kinase 1 is an oncogenic event in erythroleukemic progression, Blood 2005, 1808-1816, 106.
Li et al., Clinical significance of sphingosine kinase-1 expression in human astrocytomas progression and overall patient survival, Clin. Cancer Res. 2008, 6996-7003, 14.
Maceyka et al. Filamin A links sphingosine kinase 1 and sphingosine-1-phosphate receptors 1 at lamellipodia to orchestrate cell migration, Molecular and Cellular Biology 2008, 5687-5697, 28.
Maher et al., Malignant glioma: genetics and biology of a grave matter, Genes Dev. 2001, 1311-1333, 15.
Malchinkhuu et al., Role of p38 mitogen-activated kinase and c-Jun terminal kinase in migration response to lysophosphatidic acid and sphingosine-1-phosphate in glioma cells, Oncogene 2005, 6676-6688, 24.
Mattoon et al., The docking protein Gab1 is the primary mediator of EGF-stimulated activation of the PI-3K/Akt cell survival pathway, BMC Biology 2004, 24-35, 2.
Merrill et al., Sphingolipidomics: high-throughput, structure-specific, and quantitative analysis of sphingolipids by liquid chromatography tandem mass spectrometry, Methods 2005, 207-224, 36.
Murph and Mills, Targeting the lipids LPA and S1P and their signalling pathways to inhibit tumour progression, Expert Rev Mol Med 2007, 1-18, 9.
Nakamizo et al., Human bone marrow-derived mesenchymal stem cells in the treatment of gliomas, Cancer Res 2005, 3307-3318, 65.

(56) References Cited

OTHER PUBLICATIONS

Olivera et al., Sphingosine kinase type 1 induces G12/13-mediated stress fiber formation, yet promotes growth and survival independent of G protein-coupled receptors, JBC 2003, 46452-46460, 278.

Paugh et al., A selective sphingosine kinase 1 inhibitor integrates multiple molecular therapeutic targets in human leukemia, Blood 2008, 1382-1391, 112.

Pchejetski et al., Sphingosine kinase-1 as a chemotherapy sensor in prostate adenocarcinoma cell and mouse models, Cancer Res. 2005, 11667-11675, 65.

Qu et al., Iodophenyl tagged sphingosine derivatives: synthesis and preliminary biological evaluation, Bioorg & Med Chem Lett 2009, 3382-3385, 19.

Radeff-Huang et al., Tumor necrosis factor-alpha-stimulated cell proliferation is mediated through sphingosine kinase-dependent Akt activation and cyclin D expression, JBC 2007, 863-870, 282.

Riboni et al., Ceramide levels are inversely associated with malignant progression of human glial tumors, Glia 2002, 105-113, 39.

Sankala et al., Involvement of sphingosine kinase 2 in p53-independent induction of p21 by the chemotherapeutic drug doxorubicin, Cancer Res. 2007, 10466-10474, 67.

Shida et al., Cross-talk between LPA1 and epidermal growth factor receptors mediates up-regulation of sphingosine kinase 1 to promote gastric cancer cell motility and invasion, Cancer Res. 2008, 6569-6577, 68.

Shida et al., Targeting SphK1 as a new strategy against cancer, Current Drug Targets 2008, 662-673, 9.

Stommel et al., Coactivation of receptor tyrosine kinases affects the response of tumor cells to targeted therapies, Science 2007, 287-290, 318.

Wen et al., Malignant gliomas in adults, N. Engl J. Med. 2008, 492-507, 359.

Van Brocklyn et al., Sphingosine-1-phosphate stimulates human glioma cell proliferation through Gi-coupled receptors: role of ERK MAP kinase and phosphatidylinositol 3-kinase beta, Cancer Lett 2002, 195-204, 181.

Van Brocklyn et al., Sphingosine-1-phosphate stimulates motility and invasiveness of human glioblastoma multiforme cells, Cancer Lett 2003, 53-60, 199.

Van Brocklyn et al., Sphingosine kinase-1 expression correlates with poor survival of patients with glioblastoma multiforme: roles of sphingosine kinase isoforms in growth of glioblastoma cell lines, J Neuropathol Exp Neurol 2005, 695-705, 64.

Xia et al., Opposing effects of ERK and JNK-p38 MAP kinases on apoptosis, Science 1995, 1326-1331, 270.

Yacoub et al., MDA-7 regulates cell growth and radiosensitivity in vitro of primary (non-established) human glioma cells, Cancer Biology & Therapy 2004, 739-751, 3.

Yacoub et al., MDA-7/IL-24 plus radiation enhance survival in animals with intracranial primary human GBM tumors, Cancer Biology & Therapy 2008, 917-933, 7.

Yacoub et al., Regulation of GST-MDA-7 toxicity in human glioblastoma cells by ERBB1, ERK1/2, PI3K, and JNK1-3 pathway signaling, Mol Cancer Ther 2008, 314-329, 7.

Young et al., Roles of sphingosine-1-phosphate (S1P) receptors in malignant behaviour of glioma cells. Differential effects of S1P2 on cell migration and invasiveness, Exp Cell Res. 2007, 1615-1627, 313.

Amarente-Mendes et al., Bcr-Abl exerts its antiapoptotic effect against diverse apoptotic stimuli through blockage of mitochondrial release of cytochrome C and activation of caspase-3, Blood 1998, 1700-1705, 91.

Baran et al., Alterations of ceramide/sphingosine 1-phosphate rheostat involved in the regulation of resistance to imatinib-induced apoptosis in k562 human chronic myeloid luekemia cells, JBC 2007, 10922-10934, 282.

Berdyshev et al., De novo biosynthesis of dihydrosphingosine-1-phosphate by sphingosine kinase 1 in mammalian cells, Cell Signal 2006, 1779-1792, 18.

Betito et al., Regulation by sphingosine-1-phosphate of Bax and Bad activities during apoptosis in a MEK-dependent manner, Biochem Biophys Res Commun 2006, 1273-1277, 340.

Bonhoure et al., Overcoming MDR-associated chemoresistance in HL-60 acute myeloid leukemia cells by targeting sphingosine kinase-1, Leukemia 2006, 95-102, 20.

Brinkman, Volker, Sphingosine 1-phosphate receptors in health and disease; mechanistic insights from gene deletion studies and reverse pharmacology, Pharmacol Ther 2007, 85-105, 115.

Cheng et al., Conversion of Bcl-2 to a Bax-like death effector by caspases, Science 1997, 1966-1968, 278.

Cuvillier et al., Suppression of ceramide-mediated programmed cell death by sphingosine-1-phosphate, Nature 1996, 800-803, 381.

Cuvillier et al., Sphingosine 1-phosphate inhibits activation of caspases that cleave poly(ADP-ribose) polymerase and lamins during Fas- and ceramide-mediated apoptosis in Jurkat T lymphocytes, JBC 1998, 2910-2916, 273.

Cuvillier et al., Sphingosine 1-phosphate antagonizes apoptosis of human leukemia cells by inhibiting release of cytochrome C and Smac/DIABLO from mitochondria, Blood 2001, 2828-2836, 98.

Cuvillier et al., Involvement of sphingosine in mitochondria-dependent Fas-induced apoptosis of Type II Jurkat T cells, JBC 2000, 15691-15700, 275.

Dai et al., Pharmacological inhibitors of the mitogen-activated protein kinase (MAPK) kinase/MAPK cascade interact synergistically with UCN-01 to induce mitochondrial dysfunction and apoptosis in human leukemia cells, Cancer Res 2001, 5106-5115, 61.

De Jonghe et al., Structure-activity relationship of short chain sphingoid bases as inhibitors of sphingosine kinase, Bioorg Med Chem Lett 1999, 3175-3180, 9.

De Luca et al., NAD+/NADH as/or CoQ/CoQH2 ratios from plasma membrane electron transport may determine ceramide and sphingosine-1-phosphate levels accompanying G1 arrest and apoptosis, Biofactors 2005, 43-60, 25.

Edsall et al., N,N-dimethylsphingosine is a potent competitive inhibitor of sphingosine kinase but not of protein kinase C: modulation of cellular levels of sphingosine 1-phosphate and ceramide, Biochemistry 1998, 12892-12898, 37.

Filipits et al., Drug resistance factors in acute myeloid leukemia: a comparative analysis, Leukemia 2000, 68-76, 14.

French et al., Discovery and evaluation of inhibitors of human sphingosine kinase, Cancer Res 2003, 5962-5969, 63.

Gamble et al., Phenoxodiol, an experimental anticancer drug, shows potent antiangiogenic properties in addition to its antitumour effects, Int. J. Cancer 2006, 2412-2420, 118.

Hait et al., Sphingosine kinases, sphingosine 1-phosphate, apoptosis and diseases, Biochim Biophys Acta 2006, 2016-2026, 1758.

Hait et al., Role of sphingosine kinase 2 in cell migration toward epidermal growth factor, JBC 2005, 29462-29469, 280.

Hamada et al., Involvement of Mac-1-mediated adherence and sphingosine 1-phosphate in survival of phorbol ester-treated U937 cells, Biochem Biophys Res Commun 1998, 745-750, 244.

Igarashi et al., Effect of chemically well-defined sphingosine and its N-methyl derivatives on protein kinase C and src kinase activities, Biochemistry 1989, 6796-6800, 28.

Jarvis et al., Induction of apoptotic DNA damage and cell damage and cell death by activation of the sphingomyelin pathway, PNAS USA 1994, 73-77, 91.

Jarvis et al., Evidence for involvement of mitogen-activated protein kinase, rather than stress-activated protein kinase, in potentiation of 1-beta-D-arabinofuranosylcytosine-induced apoptosis by interruption of protein kinase c signaling, Mol Pharmacol 1998, 844-856, 54.

Jarvis et al., Coordinate regulation of stress- and mitogen-activated protein kinases in the apoptotic actions of ceramide and sphingosine, Mol Pharmacol 1997, 935-947, 52.

Jendiroba et al., Effective cytotoxicity against human leukemias and chemotherapy-resistant leukemia cell lines by N-N-dimethylsphingosine, Leuk Res. 2002, 301-310, 26.

Johnson et al., Intrinsic cytotoxicity and chemomodulatory actions of novel phenethylisothiocyanate sphingoid base derivatives in HL-60 human promyelocytic leukemia cells, J. Pharmacol. Exp. Therap. 2004, 452-461, 309.

(56) References Cited

OTHER PUBLICATIONS

Kim et al., Synthesis and evaluation of sphingoid analogs as inhibitors of sphingosine kinases, Bioorg & Med Chem 2005, 3475-3485, 13.
Kohama et al., Molecular cloning and functional characterization of murine sphingosine kinase, JBC 1998, 23722-23728, 273.
Kohno et al., Intracellular role for sphingosine kinase 1 in intestinal adenoma cell proliferation, Mol Cell Biol 2006, 7211-7223, 26.
Kono et al., F-12509A, a new sphingosine kinase inhibitor, produced by a discomycete, J. Antibiotics 2000, 459-466, 53.
Kono et al., B-5354 a, b, and c, new sphingosine kinase inhibitors, produced by a marine bacterium; taxonomy, fermentation, isolation, physico-chemical properties and structure determination, J. Antibiotics 2000, 753-758, 53.
Li et al., Sphingosine kinase-1 mediates BCR/ABL-induced upregulation of mcl-1 in chronic myeloid leukemia cells, Oncogene 2007, 7904-7908, 26.
Liu et al., Molecular cloning and functional characterization of a novel mammalian sphingosine kinase type 2 isoform, JBC 2000, 19513-19520, 275.
Maceyka et al., Sphk1 and Sphk2, sphingosine kinase isoenzymes with opposing functions in sphingolipid mechanism, JBC 2005, 37118-37129, 280.
Maggio et al., The histone deacetylase inhibitor MS-275 interacts synergistically with fludarabine to induce apoptosis in human leukemia cells, Cancer Res. 2004, 2590-2600, 64.
Marsolais & Rosen, Chemical modulators of sphingosine-1-phosphate receptors as barrier-oriented therapeutic molecules, Nature Reviews/Drug Discovery 2009, 297-307, 8.
McCormack et al, Animal models of acute myelogenous leukaemia-development, application and future perspectives, Leukemia 2005, 687-706, 19.
Milstien & Spiegel, Targeting sphingosine-1-phosphate: a novel avenue for cancer therapeutics, Cancer Cell 2006, 148-150, 9.
Mitra et al., Role of ABCC1 in export of sphingosine-1-phosphate from mast cells, PNAS USA 2006, 16394-16399, 103.
Moulding et al., Apoptosis is rapidly triggered by antisense depletion of mcl-1 in differentiating U937 cells, Blood 2000, 1756-1763, 96.
Neviani et al., FTY720, a new alternative for treating blast crisis chronic myelogenous leukemia and Philadelphia chromosome-positive acute lymphocytic leukemia, J Clin Invest 2007, 2408-2421, 117.
Ng et al., Marked suppression of tumor growth by FTY720 in a rat liver tumor model: the significance of down-regulation of cell survival Akt pathway, Int J Oncol 2007, 375-380, 30.
Niiro et al., (3z)-2-acetylamino-3-octadecen-1-ol as a potent apoptotic agent against HL-60 cells, Bioorg Med Chem 2004, 45-51,12.
Nyakern et al., Frequent elevation of Akt kinase phosphorylation in blood marrow and peripheral blood mononuclear cells from high-risk myelodysplastic syndrome patients, Leukemia 2006, 230-238, 20.
Ogretman & Hannun, Biologically active sphingolipids in cancer pathogensis and treatment, Nature Rev Cancer 2004, 604-616, 4.
Okada et al., Involvement of N-terminal-extended form of sphingosine kinase 2 in serum-dependent regulation of cell proliferation and apoptosis, JBC 2005, 36318-36325, 280.
Olivera et al., Sphingosine kinase expression increases intracellular sphingosine-1-phosphate and promotes cell growth and survival JBC 1999, 545-558, 147.

Paugh et al., The immunosuppressant FTY720 is phosphorylated by sphingosine kinase type 2, FEBS lett 2003, 189-193, 554.
Pitson et al., Phosphorylation-dependent translocation of sphingosine kinase to the plasma membrane drives its oncogenic signalling, J Exp Med 2005, 49-54, 201.
Rahmani et al., Coadministration of histone deacetylase inhibitors and perifosine synergistically induces apoptosis in human leukemia cells through Akt and ERK1/2 inactivation and the generation of ceramide and reactive oxygen species, Cancer Res 2005, 2422-2432, 65.
Rosato et al., The histone deacetylase inhibitor LAQ824 induces human leukocyte cell death through a process involving XIAP down-regulation, oxidative injury, and the acid sphingomyelinase-dependent generation of ceramide, Mol Pharmacol 2006, 216-225, 69.
Rosato et al., Mechanism and functional role of XIAP and Mcl-1 down-regulation in flavopiridol/vorinstat antileukemic interactions, Mol Cancer Ther 2007, 692-702, 6.
Sabbadini, R.A., Targeting sphingosine-1-phosphate for cancer therapy, Br J Cancer 2006, 1131-1135, 95.
Sobue et al., Quantitative RT-PCR analysis of sphingolipid metabolic enzymes in acute leukemia and myelodysplastic syndromes, Leukemia 2006, 2042-2046, 20.
Spiegel et al. Sphingosine-1-phosphate: an enigmatic signalling lipid, Nature Rev Mol Cell Biol. 2003, 397-407, 4.
Steelman et al., JAK/STAT, Raf/MEK/ERK, P13K/Akt and BCR-ABL in cell cycle progression and leukemogenesis, Leukemia 2004, 189-218, 18.
Suguira et al., Ceramide kinase, a novel lipid kinase, JBC 2002, 23294-23300, 277.
Sukocheva et al. Estrogen transactivates EGFR via the sphingosine 1-phosphate receptor Edg-3: the role of sphingosine kinase-1, J Cell Biol 2006, 301-310, 173.
Sullards, et al., Analysis of sphingosine 1-phosphate, ceramides and other bioactive sphingolipids by high-performance liquid chromatography-tandem mass spectrometry, Science STKE 2001, L1.
Swanton et al., Regulators of mitotic arrest and ceramide metabolism are determinants of sensitivity to paclitaxel and other chemotherapeutic drugs, Cancer Cell 2007, 498-512, 11.
Taha et al., Loss of sphingosine kinase-1 activates the intrinsic pathway of programmed cell death: modulation of sphingolipid levels and the induction of apoptosis, FASEB J 2006, 482-484, 20.
Xia et al., Sphingosine kinase interacts with TRAF2 and dissects tumor necrosis factor-alpha signaling, JBC 2002, 7996-8003, 277.
Zhang et al., Bcl-2 interrupts the ceramide-mediated pathway of cell death, PNAS USA 1996, 5325-5328, 93.
Delgado et al., Inhibitors of sphingolipid metabolism enzymes, Biochimica et Biophysica Acta Biomembranes, 2006, 1957-1977, 1758.
Jeremias et al., Cell death induction by betulinic acid, ceramide and TRAIL in primary glioblastoma multiforme cells, Acta Neurochir (Wien), 2004, 721-729, 146.
Bektas et al., A sphingosine kinase inhibitor induces cell death in temozolomide resistant glioblastoma cells, Cancer Chemother Pharmacol 2009,1053-1058, 64.
Van Brocklyn, James R., Sphingolipid signaling pathways as potential therapeutic targets in gliomas, Mini-Reviews in Medicinal Chemistry 2007, 984-990, 7.
Wong et al., Synthesis and Evaluation of Sphingosine Analogues as Inhibitors of Sphingosine Kinases, J. Med. Chem. 2009, 3618-3626, 52.

U373

LN229

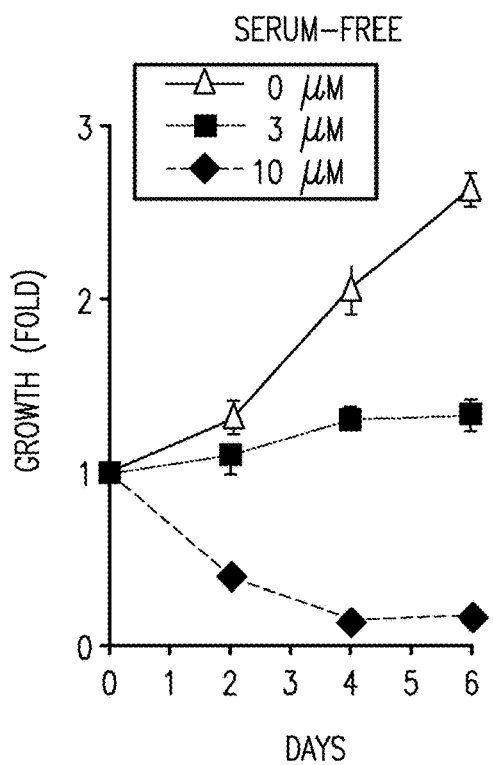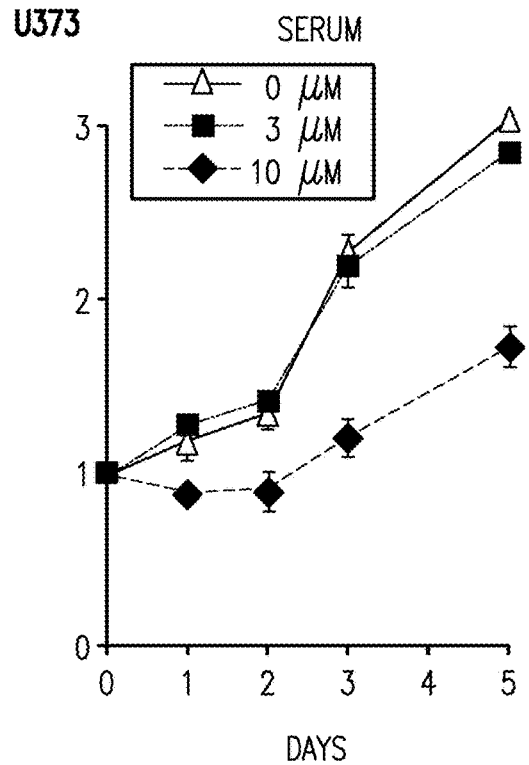
FIG. 1G    FIG. 1H
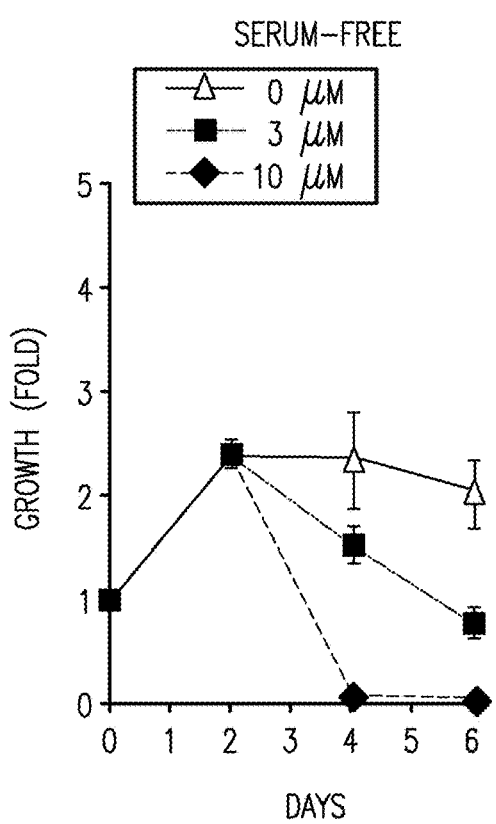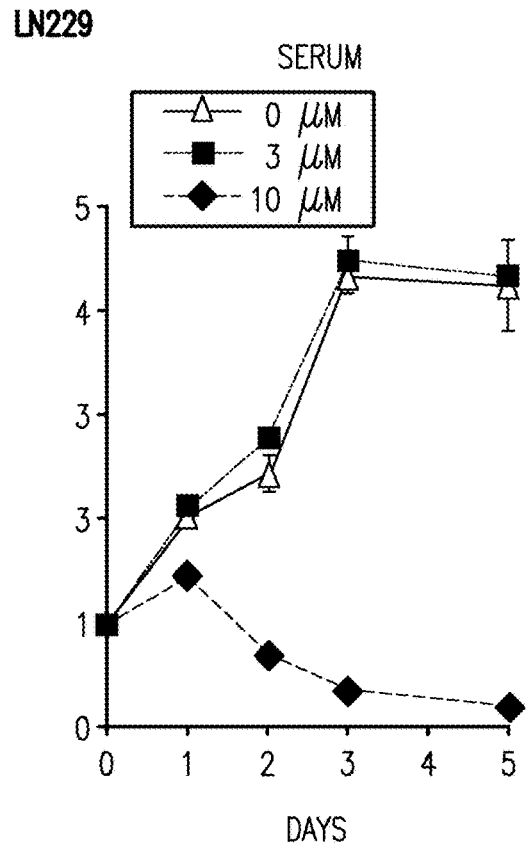
FIG. 1I    FIG. 1J

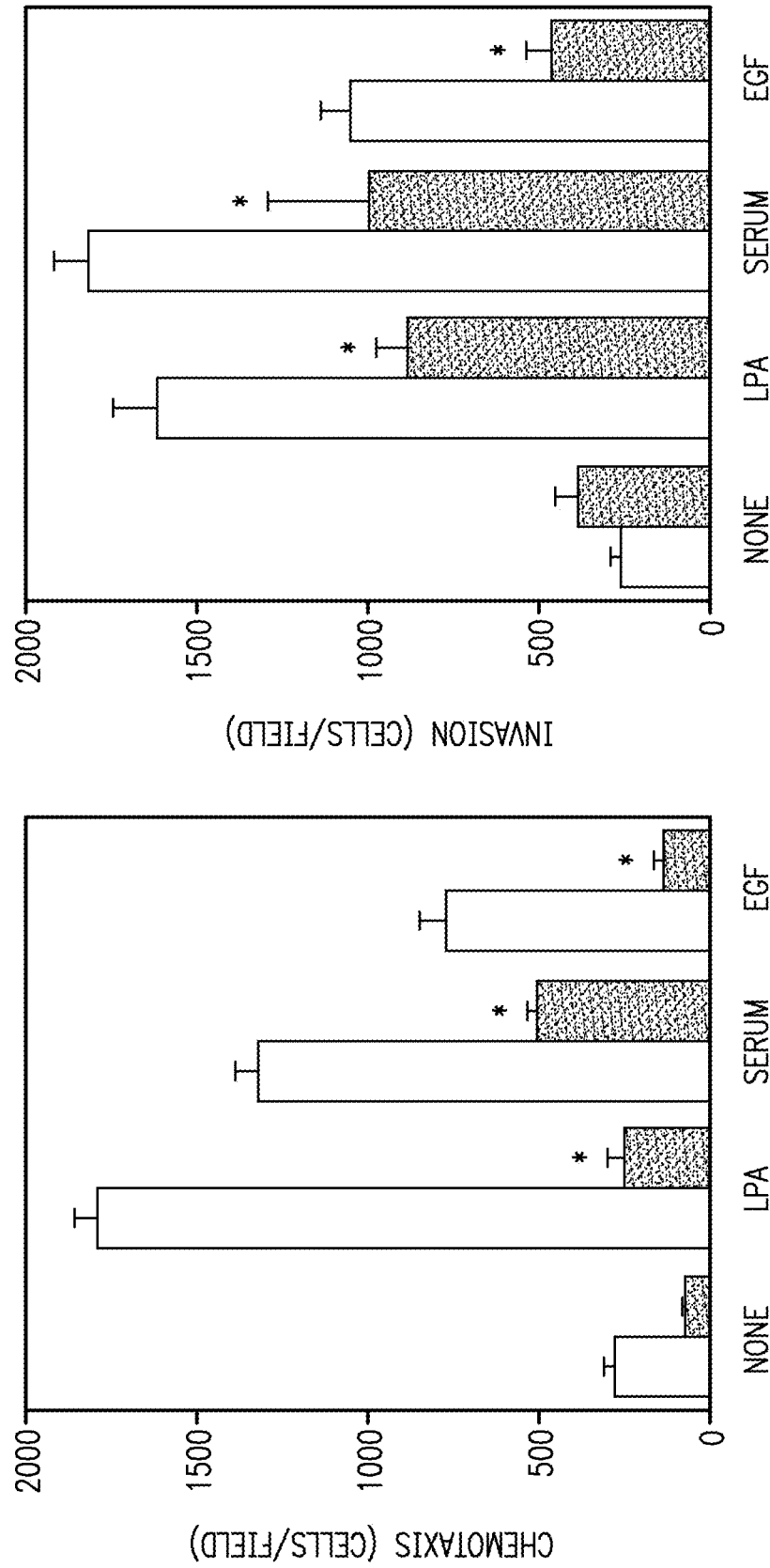

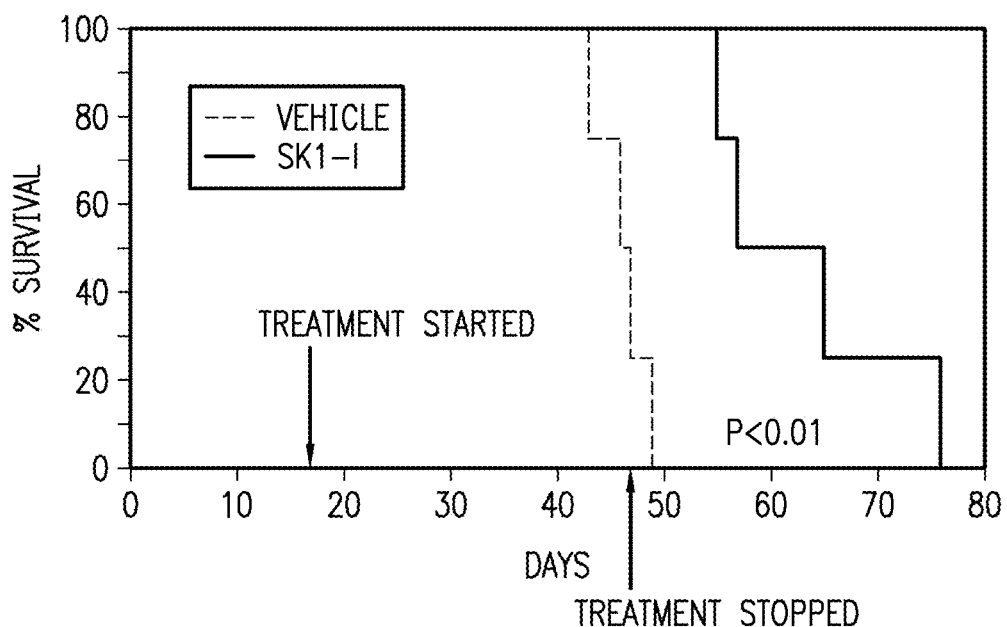
FIG. 7C
FIG. 7D
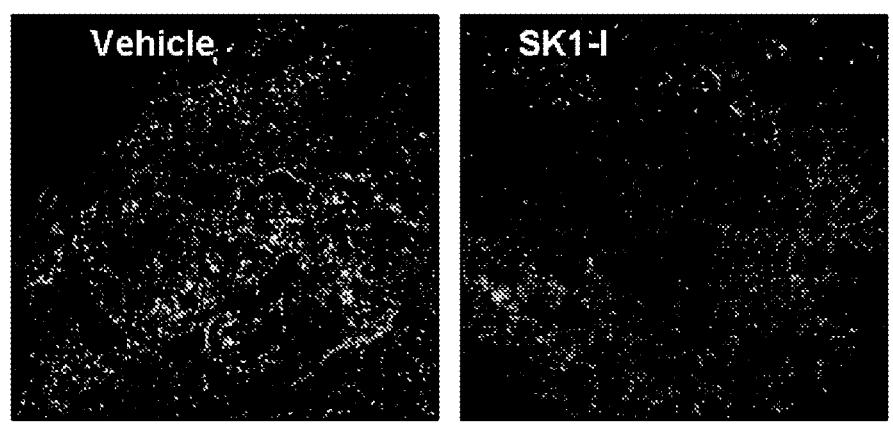

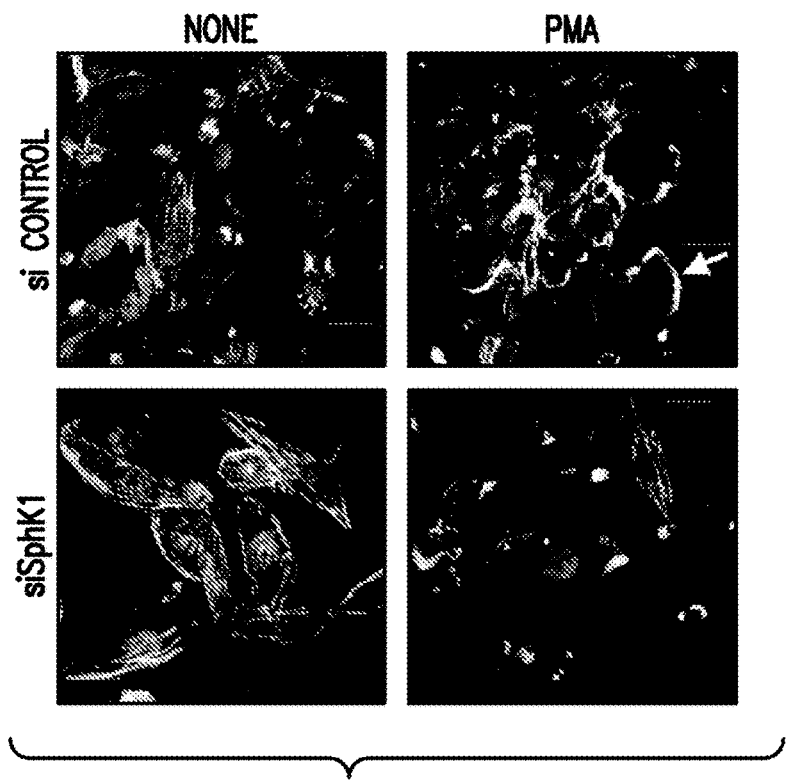
FIG. 8A
FIG. 8B
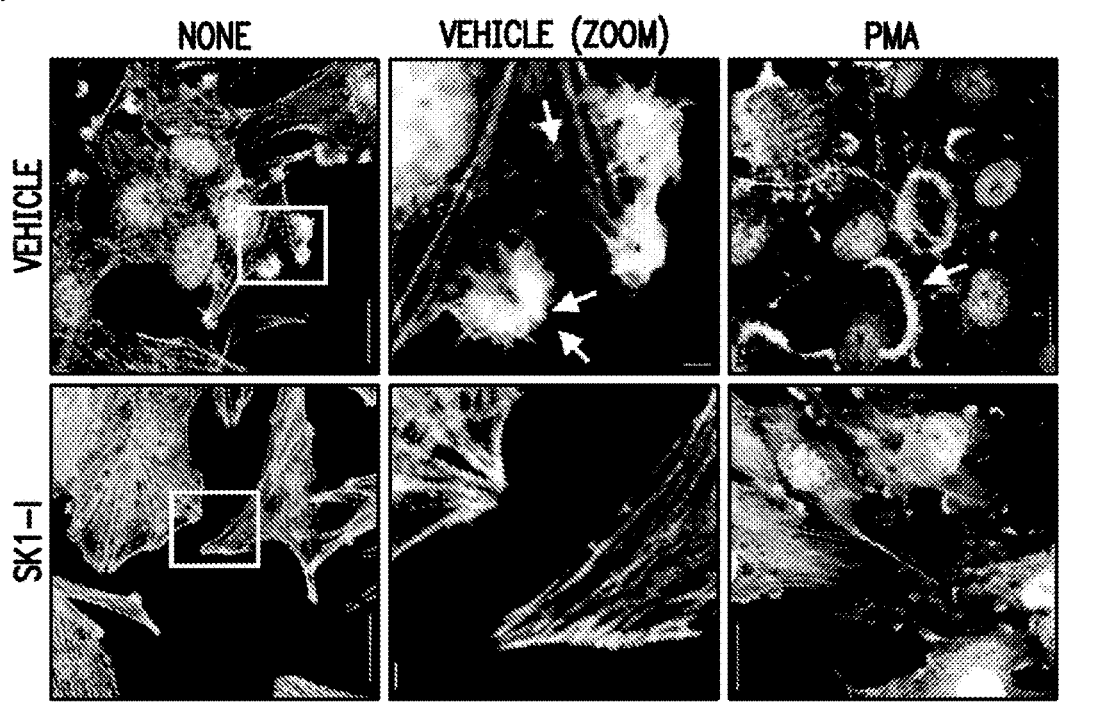

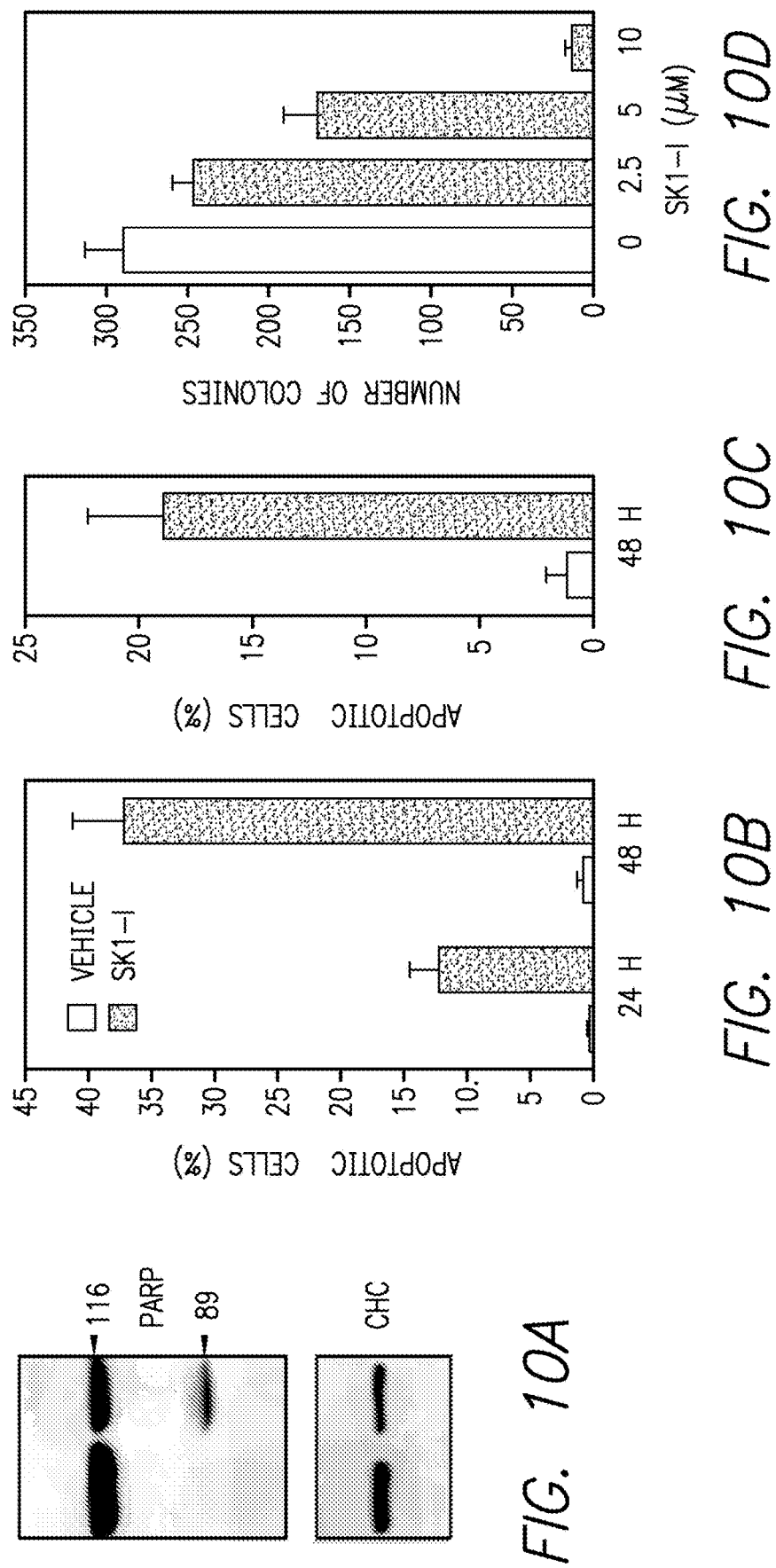

SPHINGOSINE KINASE TYPE 1 INHIBITORS AND USES THEREOF

CROSS-REFERENCE TO RELATED APPLICATIONS

This application is a continuation of U.S. application Ser. No. 16/813,961 filed Mar. 10, 2020, which is a continuation of U.S. application Ser. No. 16/572,699 filed Sep. 17, 2019, which is a continuation of U.S. application Ser. No. 16/199,337 filed Nov. 26, 2018 (now U.S. patent Ser. No. 10/456,370), which is a continuation of U.S. application Ser. No. 15/954,131 filed Apr. 16, 2018, (now U.S. Pat. No. 10,166,204), which is a continuation of U.S. application Ser. No. 15/181,826 filed Jun. 14, 2016 (now U.S. Pat. No. 9,974,758), which is a continuation of U.S. application Ser. No. 13/649,221 filed Oct. 11, 2012 (now U.S. Pat. No. 9,388,121), which is a divisional of U.S. application Ser. No. 12/584,131 filed Aug. 31, 2009 (now U.S. Pat. No. 8,314,151), which is a continuation-in-part of U.S. application Ser. No. 12/387,228 filed Apr. 29, 2009 (now U.S. Pat. No. 8,372,888), which claims the benefit of U.S. Provisional Application No. 61/048,638 filed Apr. 29, 2008, the contents of all of which are hereby incorporated by reference in their entireties.

GOVERNMENT SUPPORT STATEMENT

This invention was made with government support under Grant R01 CA61774 awarded by the National Cancer Institute (NCI). The government has certain rights in the invention.

SEQUENCE LISTING

The instant application contains a Sequence Listing which has been submitted electronically in ASCII format and is hereby incorporated by reference in its entirety. Said ASCII copy, created on Jan. 13, 2020, is named ENZ-91-CIP-D1-CON-CON-CON-CON-CON-CON-Application-SL.txt and is 921 bytes in size.

FIELD OF THE INVENTION

The invention relates to the field of sphingosine kinase Type 1 (SphK1) inhibitors.

BACKGROUND OF THE INVENTION

Sphingosine-1-phosphate (S1P), a potent lipid mediator produced from sphingosine by sphingosine kinases (SphKs), regulates many processes important for cancer progression, including cell growth and survival (Spiegel et al., *Nature Rev Mol Cell Biol.* 4:397-407, 2003). In contrast to S1P, its precursors, sphingosine and ceramide, are associated with growth arrest and induction of apoptosis (Ogretman & Hannun, *Nature Rev Cancer* 4:604-616, 2004). Thus, the balance between these interconvertible sphingolipid metabolites has been viewed as a cellular rheostat determining cell fate (Cuvillier et al., *Nature* 381:800-803, 1996). Numerous studies have shown that perturbations in the S1P/ceramide rheostat are involved in the regulation of resistance to chemotherapy and radiation therapy of neoplastic cells, including those of hematopoietic origin (Ogretman et al., supra.; Hait et al., *Biochim Biophys Acta* 1758: 2016-2026. 2006; and Milstien & Spiegel, *Cancer Cell* 9:148-150, 2006).

Two Sphk isoenzymes, SphK1 and SphK2, have been described which, while sharing many features (Kohama et al., *J. Biol Chem* 273:23722-23728, 1998; and Liu et al., *J. Biol Chem* 275:19513-19520, 2000) exhibit distinct functions. SphK1 promotes cell growth and survival (Olivera et al., *J Cell Biol* 147:545-558, 1999; Xia et al., *J. Biol Chem* 277:7996-8003, 2002; Bonhoure et al., *Leukemia* 20:95-102, 2006; and Sukocheva et al., *J Cell Biol* 173:301-310, 2006), whereas SphK2, when overexpressed, has opposite effects (Maceyka et al., *J Biol Chem* 280:37118-37129, 2005; and Okada et al., *J Biol Chem* 280:36318-36325, 2005). SphK1 is a key enzyme that regulates the S1P/ceramide rheostat (Maceyka et al., supra.; Berdyshev et al., *Cell Signal* 18:1779-1792, 2006; and Taha et al., *FASEB J* 20:482-484, 2006). Indeed, S1P and SphK1 have long been implicated in resistance of both primary leukemic cells and leukemia cell lines to apoptosis induced by commonly used cytotoxic agents (Cuvillier et al., *Nature*, 2004 supra.; Cuvillier et al., *J. Biol Chem* 273:2910-2916, 1998; Cuvillier et al., *Blood* 98:2828-2836, 2001; and Jendiroba et al., *Leuk Res* 26:301-310, 2002). Non-isozyme specific inhibitors of SphKs, such as L-threo-dihydrosphingosine (safingol) and N,N-dimethylsphingosine (DMS), are cytotoxic to leukemia cells (Jarvis et al., *Mol Pharmacol* 54:844-856, 1998; and Jendiroba et al., 2002, supra.). Interestingly, multi-drug resistant HL-60 myelogenous leukemia cells were more sensitive to DMS than the parental cells (Jendiroba et al., 2002, supra.). Moreover, SphK1 activity was lower in HL-60 cells sensitive to doxorubicin or etoposide than in MDRI- or MRP1-positive HL-60 cells. Enforced expression of SphK1 in sensitive HL-60 cells blocked apoptosis whereas downregulation of Sphk1 overcame chemoresistance by inducing mitochondria-dependent apoptosis (Bonhoure et al., 2006, supra.). These observations take on added significance in light of evidence that MDR expression is a strong prognostic indicator in acute myelogenous leukemia (AML) (Filipits et al., *Leukemia* 14:68-76, 2000) and that the MDR phenotype, which commonly arises following treatment of AML with anthracyclines or plant-based alkaloids, is thought to represent an obstacle to successful chemotherapy. In addition, resistance of K562 human chronic myeloid leukemia cells to Imatinib, an inhibitor of Bcr-Abl tyrosine kinase, correlated with expression of SphK1 and generation of S1P, whereas downregulation of SphK1 increased sensitivity to Imatinib-induced apoptosis in resistant cells (Baran et al., *J Biol Chem* 282:10922-10934, 2007). Thus, the development of effective and specific inhibitors of SphK1 might prove useful not only in diminishing levels of pro-survival S1P, but also in potentiating ceramide generation, a process that mediates, at least in part, the pro-apoptotic actions of certain cytotoxic agents (Maggio et al., *Cancer Res* 64:2590-2600, 2004; Rahmani et al., *Cancer Res* 65:2422-2432, 2005; and Rosato et al., *Mol Pharmacol* 69:216-225, 2006).

Sphingosine kinase inhibitors have been described (Kim et al., *Bioorg & Med Chem* 13:3475-3485, 2005; Kono et al., *J. Antibiotics* 53:459-466, 2000; Kono et al., *J. Antibiotics* 53:753-758, 2000; Marsolais & Rosen, *Nature Reviews/Drug Discovery* 8:297-307, 2009; and US 2008/0167352 A1 (Smith et al., published Jul. 10, 2008). None of these publications describe, however, the novel sphingosine kinase Type 1 inhibitors herein. Halide modified analogs of sphingosine derivatives have also been described (Qu et al., *Bioorg & Med Chem Letters* 19:3382-3385 (2009).

In U.S. patent application Ser. No. 12/387,228 (filed Apr. 29, 2009), there is described a potent, water-soluble inhibitor of SphK1 (SK1-I) that triggers multiple perturbations in activation of various signaling and survival-related proteins.

SK1-I markedly induced apoptosis in human leukemic cell lines as well as blasts obtained from patients with AML and inhibited growth of AML xenograft tumors. SK1-1 serves as model for other related compounds which are described further below.

Glioblastoma multiforme (GBM) is the most prevalent and lethal type of primary central nervous system tumors with a median survival of 10-12 months, even after aggressive surgery, radiation and advanced chemotherapy (Maher et al., *Genes Dev* 15:1311-1333, 2001). Poor prognosis of patients with GBM has recently been correlated with elevated expression of sphingosine kinase type 1 (SphK1) (Van Brocklyn et al., *J Neuropathol Exp Neurol* 64:695-705, 2005; Li et al., *Clin Cancer Res* 14:6996-7003, 2008), one of the SphK isoenzymes that generates the pleiotropic lipid mediator, sphingosine-1-phosphate (S1P). S1P has been implicated in the etiology of GBM due to its involvement in various cell processes particularly important for cancer progression, including growth, survival, migration, invasion, tumor growth, angiogenesis, and metastasis (Van Brocklyn et al., *Cancer Lett* 181:195-204, 2002; Lepley et al., *Cancer Res.* 65:3788-3795, 2002; Radeff-Huang et al., *J Biol Chem* 282:863-870, 2007; and Young et al., *Exp Cell Res* 313:1615-1627, 2007). The biological effects of this serum-borne lipid are mainly mediated by a family of five specific G protein-coupled receptors, designated $S1P_{1-5}$. (Murph and Mills, *Expert Rev Mod Med* 9:1-18, 2007). Of those, $S1P_{1-3}$, are expressed in the majority of human glioblastoma cell lines and are involved in S1P-mediated proliferation (Van Brocklyn et al., *Cancer Lett* 181:195-204, 2002, supra). Although S1P has no effect on matrix metalloproteinase secretion, it enhances glioblastoma cell adhesion and also stimulates their motility and invasiveness (Van Brocklyn et al., *Cancer Lett* 199:53-60, 2003). Because S1P is present at high levels in brain tissue, it is possible that autocrine or paracrine signaling by S1P through its receptors enhances both glioma cell proliferation and invasiveness (Anelli et al., *J Biol Chem* 283:3365-3375, 2008).

To explore the therapeutic implications of targeting SphK1 for treatment of GBM, the effects of a newly developed isozyme-specific inhibitor of SphK1, SK1-1 (Paugh et al., *Blood* 112:1382-1391, 2008), was examined and found that it inhibits growth of GBM in vitro and in vivo. These specific SphK1 inhibitors are useful for treatment, either alone or in combination with advanced chemotherapeutic agents.

SUMMARY OF THE INVENTION

This invention provides a composition of matter having the structure:

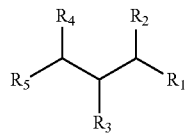

wherein $R_1$ is H or comprises N, S, a phosphate group or a phosphonate group, and any combination thereof; wherein $R_2$ is H, or comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_3$ is H or comprises OH, $NR_6R_7$, $N^+R_6R_7R_8$, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_6$, $R_7$ and $R_8$ independently comprise H, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_4$ is H or comprises OH, a halide, =O, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_5$ comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

This invention also provides a composition of matter having the structure:

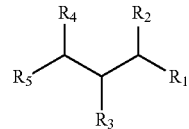

wherein $R_1$ is H or comprises OH, N, S, a phosphate group or a phosphonate group, and any combination thereof; wherein $R_2$ comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing, wherein said $R_2$ is substituted with one or more halides; wherein $R_3$ is H or comprises OH, $NR_6R_7$, $N^+R_6R_7R_8$, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_6$, $R_7$ and $R_8$ independently comprise H, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_4$ is H or comprises OH, a halide, =O, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_5$ comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

This invention additionally provides a composition of matter having the structure:

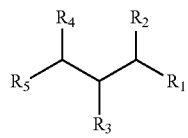

wherein $R_1$ is H or comprises OH, N, S, a phosphate group or a phosphonate group, and any combination thereof; wherein $R_2$ is H, or comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_3$ is H or comprises OH, $NR_6R_7$, $N^+R_6R_7R_8$, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_6$, $R_7$ and $R_8$ independently comprise H, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_4$ is H or comprises OH, a halide, =O, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_5$ comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_3$ and $R_4$ each comprises respectively an isomer that is 2R, 3R; 2S, 3S or 2R, 3S.

Also provided by the present invention is a composition of matter having the structure:

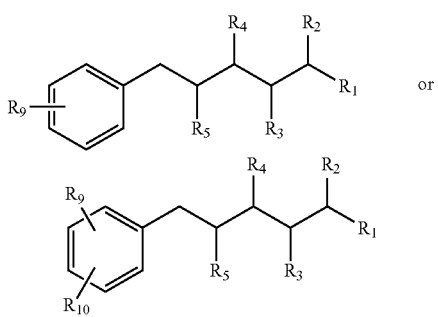

wherein $R_1$ is H or comprises O, N, S, a phosphate group or a phosphonate group, and any combination thereof; wherein $R_2$ is H, or comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_3$ is H or comprises OH, $NR_6R_7$, $N^+R_6R_7R_8$, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_6$, $R_7$ and $R_8$ independently comprise H, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_5$ is H or comprises OH, a halide, =O, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_9$ and $R_{10}$ independently comprise a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

Also provided by the present invention is a composition of matter having the structure:

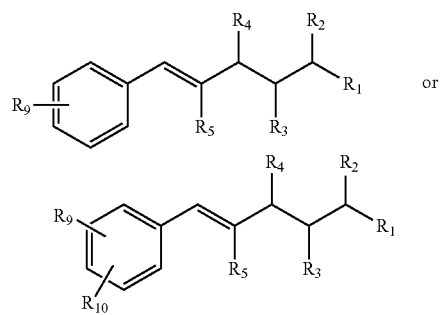

wherein $R_1$ is H or comprises O, N, S, a phosphate group or a phosphonate group, and any combination thereof; wherein $R_2$ is H, or comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_3$ is H or comprises OH, $NR_6R_7$, $N^+R_6R_7R_8$, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_6$, $R_7$ and $R_8$ independently comprise H, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_5$ is H or comprises OH, a halide, =O, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_9$ and $R_{10}$ independently comprise a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

This invention also provides a method for monitoring the course of pharmacokinetics of a drug after administration to a subject or patient, the process comprising administering to a subject or patient a drug comprising any of the above described compounds, and detecting the administered drug at selected intervals, thereby monitoring the course of pharmacokinetics of the drug in the subject or patient.

These compounds are useful in a number of indications or disease conditions, including treatments for cancer, asthma, anaphylaxis, autophagy, central nervous system, including glioblastoma multiforme and others. Additionally, this invention provides a method for treating tumors of the central nervous system in which any of the above described compounds are administered to a subject or patient having a tumor or tumors of the central nervous system.

Other aspects of the compounds and methods of the present invention are provided in further detail below.

BRIEF DESCRIPTION OF THE DRAWINGS

FIGS. 1A-1J. FIG. 1A shows decreased growth of U373 cells in serum-free medium in the presence (filled squares) and in the absence (open circles) of siRNA targeted to a specific sequence of SphK1 mRNA. FIG. 1B shows decreased growth of U373 cells in medium containing serum in the presence (filled squares) and in the absence (open circles) of siRNA targeted to a specific sequence of SphK1 mRNA. FIG. 1C shows decreased growth of LN229 cells in serum-free medium in the presence (filled squares) and in the absence (open circles) of siRNA targeted to a specific sequence of SphK1 mRNA. FIG. 1D shows decreased growth of LN229 cells in medium containing serum in the presence (filled squares) and in the absence (open circles) of siRNA targeted to a specific sequence of SphK1 mRNA. FIG. 1E shows the drastic reduction of SphK1 in U373 and LN229 cells in the presence of siRNA targeted to a specific sequence of SphK1 mRNA. FIG. 1F shows that expression of SphK1 in U373 cells is much lower than expression of SphK1 in LN229 cells. FIG. 1G shows decreased growth of U373 cells in serum-free medium in the presence of 3 μM (filled squares) and 10 μM SK1-I (filed diamonds) as compared to growth in the absence (open triangles) of SK1-I. FIG. 1H shows decreased growth of U373 cells in medium containing serum in the presence of 3 μM (filled squares) and 10 μM SK1-I (filed diamonds) as compared to growth in the absence (open triangles) of SK1-I. FIG. 1I shows decreased growth of LN229 cells in serum-free medium in the presence of 3 μM (filled squares) and 10 μM SK1-I (filed diamonds) as compared to growth in the absence (open triangles) of SK1-I. FIG. 1J shows decreased growth of LN229 cells in medium containing serum in the presence of 3 μM (filled squares) and 10 μM SK1-I (filed diamonds) as compared to growth in the absence (open triangles) of SK1-I.

FIGS. 2A-2D. FIG. 2A shows chemotaxis of LN229 cells toward serum, EGF and lysophosphatidic acid (LPA) is significantly inhibited by SK1-I. FIG. 2B shows that LPA, serum and EGF also stimulated in vitro invasion of LN229 cells into the basement membrane matrix Matrigel, which was greatly attenuated in the presence of SK1-I. FIG. 2C shows that SK1-I reduced Akt phosphorylation at Thr308, Ser473, and p70S6K phosphorylation at Thr 389 in LN229 cells stimulated by serum, LPA and EGF, but that SK1-I did not significantly affect EGF- or serum-induced ERK1/2 activation or serum-, LPA- or EGF-stimulated ERK1/2 phosphorylation. FIG. 2D shows the reversal of inhibition of EGF-induced Akt phosphorylation by SK1-I by addition of S1P, and that SK1-I did not affect EGF-induced tyrosine phosphorylation of GEFR or Gab 1.

FIG. 3A shows a significant reduction in S1P levels within 20 minutes after addition of SK1-I, and 70% reduction in S1P levels within 1 hour that was accompanied by increased sphingosine levels and no major changes in ceremide levels. FIG. 3B shows that increased phosphorylation of JNK in LN229 cells after addition of SK1-I was accompanied by enhanced phosphorylation of c-JUN and ATF-2, and that SP600125 blocked JNK activation as demonstrated by inhibition of c-Jun and ATF-2 phosphorylation. FIG. 3C shows that 1 μM of SP600125 reversed SK1-I induced lethality of LN229 cells. FIG. 3D shows that addition of a specific JNK peptide inhibitor significantly reversed the cytotoxic effects of SK1-I, whereas a control peptide was ineffective. FIG. 3E shows that addition of agents that perturb ERK1/2, Akt or INK signaling greatly enhanced SK1-I lethality. FIG. 3F shows that expression of dominant-negative MEK1 enhanced SK1-I induced LN229 cell death, while dominant-negative Akt did not. In addition, expression of constitutively-activated AKT or MEK1 or expression of Bcl-xL suppressed cell death induced by SK1-I.

FIG. 4A shows that growth of GMB6 glioblastoma cells in serum-free medium is greatly reduced by SK1-I in a dose-dependent manner. FIG. 4B shows that 10 μM SK1-I markedly reduced growth of GMB6 cells in medium containing serum. FIG. 4C shows that SK1-I suppressed serum- and EGF-induced invasion of GBM6 cells. FIG. 4D shows that SK1-I reduced basal and serum- and EGF-stimulated phosphorylation of Akt shortly following treatment without affecting pERK1/2 levels.

FIG. 5A shows that tumors resulting from subcutaneous injection of LN229 cells into the flanks of mice that were subsequently either treated with SK1-I or vehicle were significantly smaller in the SK1-I treatment group. FIG. 5B shows that treatment with SK1-I reduced tumor weight by almost 4-fold as compared to vehicle treated controls. FIG. 5C shows that tumor volume and size were reduced in mice treated with SK1-I as compared to vehicle treated controls.

FIGS. 7A-7D. FIG. 7A shows that mice implanted intracranially with GFP-labeled LN229 cells and subsequently treated with SK1-I showed no tumors whereas vehicle treated mice showed a large tumor in the right hemisphere of the brain. FIG. 7B shows that gadolinium enhancement showed a small tumor in the brain of one SK1-I mouse at the site of injection. FIG. 7C shows that at day 40 after intracranial implantation the vehicle treated group began to show symptoms of tumor burden while the SK1-I treated group did not show any symptoms, and that Sk1-I administration showed significant survival benefit as compared to vehicle treated mice. FIG. 7D shows significantly fewer invading cells and noticeable areas of necrosis in the middle of tumors in intracranial tumor sections from mice treated with Sk1-I compared to vehicle treated animals.

FIGS. 8A-8D. FIG. 8A shows distribution of F-actin across unstimulated U373 cells as revealed by staining with Alexa488-conjugated phalloidin (left panels) and F-actin condensation at the leading edge within lamellipodia in response to PMA exposure (right panels) in the absence (top panels) or in the presence (bottom panels) of siRNA targeted to a specific sequence of SphK1 mRNA. FIG. 8B shows distribution of F-actin across U373 cells as revealed by staining with Alexa488-conjugated phalloidin (left panels), in cells in vehicle (middle panels) and in response to PMA exposure (right panels) in the absence (top panels) or in the presence (bottom panels) of SK1-I. FIG. 8C shows lamellipodia length of F-actin in unstimulated U373 cells and in U373 cells in response to PMA exposure in the absence or in the presence of siRNA targeted to a specific sequence of SphK1 mRNA. FIG. 8D shows lamellipodia length of F-actin in unstimulated U373 cells and in U373 cells in response to PMA exposure in the absence or in the presence of SK1-I.

FIG. 9A shows chemotaxis of U373 cells toward serum or EGF in Boyden chamber assays was reduced in the presence of SK1-I. FIG. 9B shows that SK1-I reduced basal Akt phosphorylation, that serum and EGF enhanced phosphorylation of Akt in U373 cells and that Sk1-I did not reduce EGF- and serum-induced ERK1/2 activation in U373 cells.

FIGS. 10A-10D. FIG. 10A shows that treatment of LN229 cells with SK1-I induced apoptosis by increased cleavage of PARP. FIG. 10B shows that treatment of LN229 cells with SK1-I increased fragmented and condensed nuclei and delayed activation of JNK. FIG. 10C shows that treatment of LN229 cells with SK1-I increased DNA strand breaks as detected by TUNEL staining. FIG. 10D shows that treatment of LN229 cells with SK1-I suppressed long-term survival of the cells in clonogenic assays.

DETAILED DESCRIPTION OF THE INVENTION

Figure 1A:
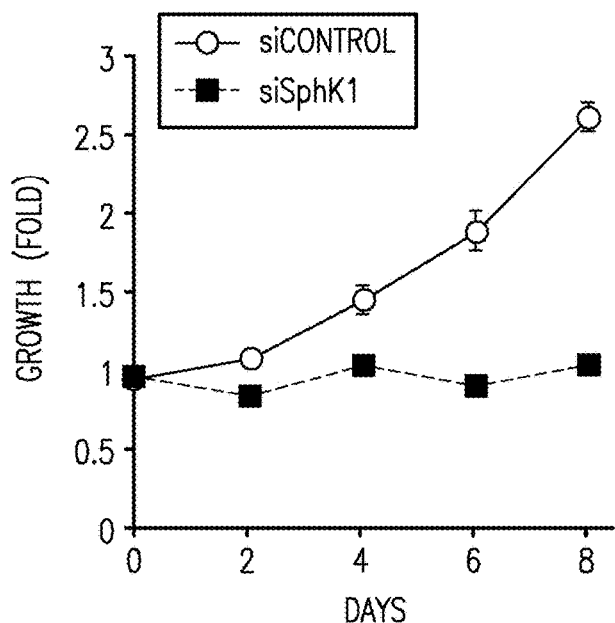

The compositions and analogs of the present invention are designed in various forms, including their resemblance to the substrate, to the product formed by reaction of the substrate and enzyme, e.g., sphingosine kinases including sphingosine kinase Type 1, and to any intermediates formed in reaction. Reaction products are usually characterized by low binding affinity, e.g., low Km. Still, by providing enough binding affinity to the reaction products, the compositions and analogs of the present invention are useful and thereby produce useful inhibitory or regulatory effects against the desired enzyme.

Preferential Inhibition of SphK1

The ability to identify compounds and analogs which preferentially inhibit or regulate SphK1 as opposed to SphK2 is desirable. Five fold and even ten fold greater inhibition of SphK1 over SphK2 is particularly useful.

The ability to inhibit SphK 1 differentially from SphK 2 allows assessments of the individual SphK 1 and SphK 2 activities when both activities are present in a cell extract. This is easily carried out by an analysis of the amount of the total SphK activity (i.e., transformation of Sph into Sph-P) in the absence of the inhibitor (which should be a composite of the individual SphK1 and SphK2 activities) and in the presence of the SphK 1 inhibitor where activity should only be generated by the SphK 2. Since the total activity as well as the contribution derived from SphK2 are known, a simple subtraction gives an estimate of the initial contribution by SphK1 in the assay carried out in the absence of the inhibitor. This is useful for diagnisitic or prognostic evaluations when viewed n the context of diseases where these levels are abnormal compared to the healthy state of an individual.

The present invention provides a composition of matter having the structure:

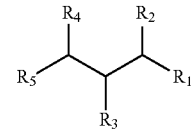

wherein $R_1$ is H or comprises N, S, a phosphate group or a phosphonate group, and any combination thereof; wherein $R_2$ is H, or comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_3$ is H or comprises OH, $NR_6R_7$, $N^+R_6R_7R_8$, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_6$, $R_7$ and $R_8$ independently comprise H, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_4$ is H or comprises OH, a halide, =O, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_5$ comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

In the just described composition, one or more of the groups, $R_2$, $R_3$, $R_4$, $R_5$, $R_6$, $R_7$ or $R_8$, comprise at least one double bond or at least one triple bond, or both at least one double bond and at least one triple bond.

In the just described composition, the straight carbon chain, the branched carbon chain, the straight carbon chain comprising one or more heteroatoms or the branched carbon chain comprising one or more heteroatoms in $R_2$, $R_3$, $R_4$, $R_5$, $R_6$, $R_7$ or $R_8$ comprises an alkyl, a substituted alkyl, an alkene, a substituted alkene, an alkyne or a substituted alkyne, and combinations of any of the foregoing.

Also provided by this invention is a composition, as just described but wherein $R_5$ comprises at least one double bond, this composition having the structure:

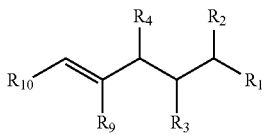

wherein $R_9$ comprises H, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_{10}$ comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing. In this composition, $R_9$ or $R_{10}$, or both $R_9$ and $R_{10}$ comprise at least one double bond or at least one triple bond, or at least one double bond and at least one triple bond.

Furthermore, in this composition just described, $R_5$ can comprise at least one triple bond, such composition having the structure:

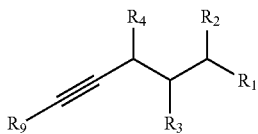

wherein $R_9$ comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

In the compositions above described, one or more of the groups, $R_2$, $R_3$, $R_4$, $R_5$, $R_6$, $R_7$, $R_8$, $R_9$ or $R_{10}$ comprise one or more halides.

Also provided by this invention is the composition in accordance with those just described, wherein $R_5$ comprises an aromatic ring, the composition having the structure:

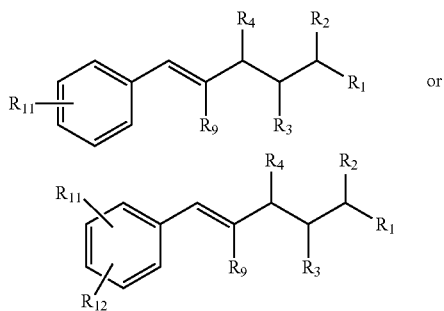

wherein $R_{11}$ comprises H, OH, a halide, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; an wherein $R_{11}$ and $R_{12}$ independently comprise a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

Additionally, in the composition just described, $R_{10}$ can comprise an aromatic group, the composition having the structure:

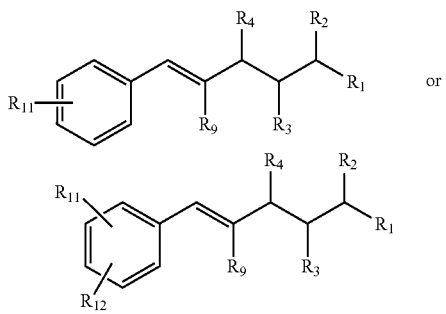

wherein $R_{11}$ comprises H, OH, a halide, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_{11}$ and $R_{12}$ independently comprise a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

In the just described compositions, $R_{10}$, $R_{11}$, or both $R_{10}$ and $R_{11}$ comprise one or more halides.

In another aspect of the above described compositions, $R_3$ and $R_4$ independently can comprise the same or different R or S isomer. $R_3$ and $R_4$ can also together comprise an isomer that is 2R, 3R; 2S, 3S; 2R, 3S; or 2S, 3R.

Additionally, in the compositions above described, the C4 atom may be asymmetric and may comprise the 4R conformation or the 4S conformation.

In the compositions of the present invention, a detectable label can be included. Such a detectable label comprises a ligand or a fluorescent dye. The ligand can comprise but is not limited to biotin, digoxygenin or fluorescein. The fluorescent dye can assume a number of various well-known fluorescent dyes including fluorescein, fluorescein isothiocyanate (FITC), 6-carboxyfluorescein (6-FAM), naphthofluorescein, rhodamine, rhodamine 6G, rhodamine X, rhodol, sulforhodamine 101, tetramethylrhodamine (TAMRA), tetramethylrhodamineisothiocyanate (TRITC), 4,7-dichlororhodamine, eosin, eosinisothiocyanate (EITC), dansyl, hydroxycoumarin, methoxycoumarin or p-(Dimethyl aminophenylazo) benzoic acid (DABCYL), cyanine dyes or derivatives, and any combinations of the foregoing.

Moreover, in the present compositions, the C1 atom can be asymmetric and can comprise the 1R conformation. Alternatively, the C1 atom can be asymmetric and comprises the is conformation.

In the above compositions, the heteroatom or heteroatoms comprise S, N or O, and combinations thereof. Such heteroatom or heteroatoms form linkages which are well known in the art. Those skilled in the art will readily appreciate such linkages which have been disclosed. See, for example, U.S.

Pat. No. 4,707,440. For illustration purposes only, the following linkages are useful in accordance with this invention:

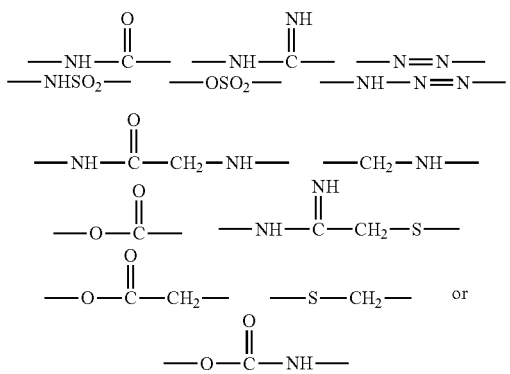

and a combination of any of the foregoing. Those skilled in the art will appreciate that such linkages can take the form just described, or they can take a reverse or opposite form.

In the compositions above described, at least two of the groups, $R_1$, $R_2$, $R_3$, $R_4$ or $R_5$, can be joined together to form one or more rings. Thus, any of these groups can be cyclized to form additional rings between such ring forming R groups. This cyclization through ring forming R groups can be carried out through conventional methods. Such joining of the individual R groups can be covalently or even non-covalent.

The invention herein also provides a composition of matter having the structure:

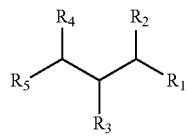

wherein $R_1$ is H or comprises OH, N, S, a phosphate group or a phosphonate group, and any combination thereof; wherein $R_2$ comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing, wherein said $R_2$ is substituted with one or more halides; wherein $R_3$ is H or comprises OH, $NR_6R_7$, $N^+R_6R_7R_8$, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_6$, $R_7$ and $R_8$ independently comprise H, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_4$ is H or comprises OH, a halide, =O, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_5$ comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

In this just described composition, one or more of the groups, $R_2$, $R_3$, $R_4$, $R_5$, $R_6$, $R_7$ or $R_8$, can comprise at least one double bond or at least one triple bond, or both at least one double bond and at least one triple bond.

Furthermore, the straight carbon chain, the branched carbon chain, the straight carbon chain comprising one or more heteroatoms or the branched carbon chain comprising one or more heteroatoms in $R_2$, $R_3$, $R_4$, $R_5$, $R_6$, $R_7$ or $R_8$ can comprise an alkyl, a substituted alkyl, an alkene, a substituted alkene, an alkyne or a substituted alkyne, and combinations of any of the foregoing.

In the just described composition, the group $R_5$ can comprise at least one double bond, the composition having the structure:

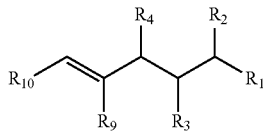

wherein $R_9$ comprises H, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_{10}$ comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

In the composition just described, the group $R_9$ or the group $R_{10}$, or both $R_9$ and said $R_{10}$ can comprise at least one double bond or at least one triple bond, or at least one double bond and at least one triple bond.

In the above composition wherein $R_5$ comprises at least one triple bond, the composition has the structure:

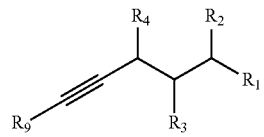

wherein $R_9$ comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

In the compositions above described, one or more of the groups, $R_3$, $R_4$, $R_5$, $R_6$, $R_7$, $R_8$, $R_9$ or $R_{10}$ comprises one or more halides.

In the above composition wherein $R_5$ comprises an aromatic ring, the composition has the structure:

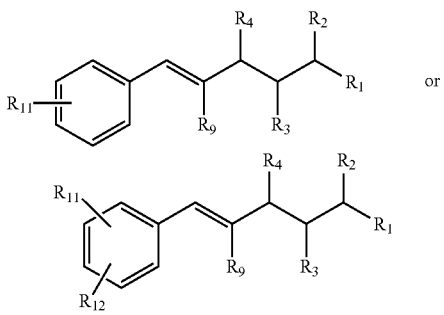

wherein $R_9$ comprises H, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_{11}$ comprises H, OH, a halide, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_{11}$ and $R_{12}$ independently comprise a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

In the above composition wherein $R_{10}$ comprises an aromatic group, the composition has the structure:

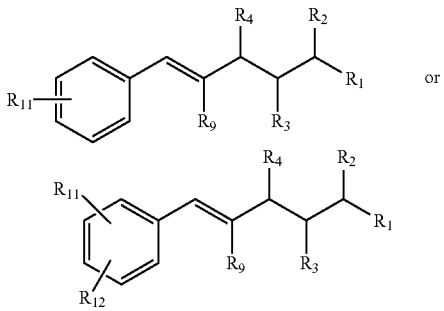

wherein $R_{11}$ comprises H, OH, a halide, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_{11}$ and $R_{12}$ independently comprise a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

Furthermore, in the above described compositions wherein the group $R_{10}$, the group $R_{11}$, or both $R_{10}$ and $R_{11}$ comprise one or more halides.

Also, in accordance with this invention, the groups $R_3$ and $R_4$ independently can comprise the same or different R or S isomer in the above-described compositions. Moreover, the groups $R_3$ and $R_4$ can together comprise an isomer that is 2R, 3R; 2S, 3S; 2R, 3S; or 2S, 3R.

In the above described composition, the C4 atom can be asymmetric and can comprise the 4R conformation. Alternatively, the C4 atom can be asymmetric and can comprises the 4S conformation.

The alkene containing compositions above can further comprise a detectable label. Such a detectable label can comprise a ligand or a fluorescent dye. Where the former, the ligand can comprise biotin, digoxygenin or fluorescein. Where a fluorescent dye is contemplated as the detectable label, the fluorescent dye can comprise fluorescein, fluorescein isothiocyanate (FITC), 6-carboxyfluorescein (6-FAM), naphthofluorescein, rhodamine, rhodamine 6G, rhodamine X, rhodol, sulforhodamine 101, tetramethylrhodamine (TAMRA), tetramethylrhodamineisothiocyanate (TRITC), 4,7-dichlororhodamine, eosin, eosinisothiocyanate (EITC), dansyl, hydroxycoumarin, methoxycoumarin or p-(Dimethyl aminophenylazo) benzoic acid (DABCYL), cyanine dyes or derivatives, and any combinations of the foregoing. The foregoing list of fluorescent dyes is illustrative and is not intended to limit this invention.

Additionally, in these alkene compositions, the C1 atom may be asymmetric and may comprise the 1R conformation or the 1S conformation.

In these alkene compositions just described, the heteroatom or heteroatoms can comprise S, N or O, and combinations thereof. As described earlier, the heteroatom or heteroatoms can form a linkage comprising any of the following linkages:

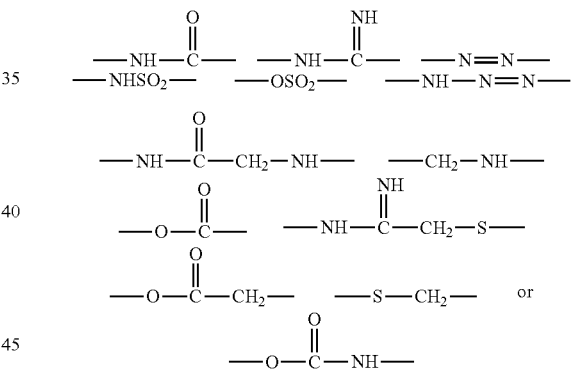

and a combination of any of the foregoing. Such linkages have been described (see, e.g., U.S. Pat. No. 4,707,440) and are known to those skilled in the chemical arts. These linkages can take the form above, or they can be used in a reverse or opposite orientation. Thus, the above form of such linkages is in no way intended to be limiting to this invention.

In the alkene containing composition, at least two of the groups, $R_1$, $R_2$, $R_3$, $R_4$ or $R_5$, can be joined together to form one or more rings through cyclization as described above.

This invention additionally provides a composition of matter having the structure:

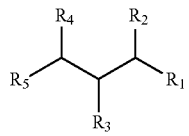

wherein $R_1$ is H or comprises OH, N, S, a phosphate group or a phosphonate group, and any combination thereof; wherein $R_2$ is H, or comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_3$ is H or comprises OH, $NR_6R_7$, $N^+R_6R_7R_8$, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_6$, $R_7$ and $R_8$ independently comprise H, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_4$ is H or comprises OH, a halide, =O, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_5$ comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_3$ and $R_4$ each comprises respectively an isomer that is 2R, 3R; 2S, 3S or 2R, 3S.

In another embodiment, one or more of said $R_2$, $R_3$, $R_4$, $R_5$, $R_6$, $R_7$ or $R_8$ in the just described composition can comprise at least one double bond or at least one triple bond, or both at least one double bond and at least one triple bond.

Furthermore, the straight carbon chain, the branched carbon chain, the straight carbon chain comprising one or more heteroatoms or the branched carbon chain comprising one or more heteroatoms in $R_2$, $R_3$, $R_4$, $R_5$, $R_6$, $R_7$ or $R_8$ can comprise an alkyl, a substituted alkyl, an alkene, a substituted alkene, an alkyne or a substituted alkyne, and combinations of any of the foregoing.

Additionally, in this composition, the group $R_5$ can comprise at least one double bond, so that the composition has the structure:

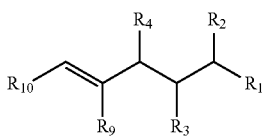

wherein $R_9$ comprises H, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_{10}$ comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing. In another embodiment, the group $R_9$ or the group $R_{10}$, or both $R_9$ and $R_{10}$ can comprise at least one double bond or at least one triple bond, or at least one double bond and at least one triple bond.

Also contemplated by this invention is a composition as just described but where $R_5$ comprises at least one triple bond, such a composition having the structure:

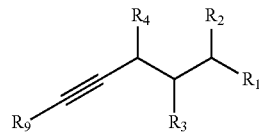

wherein $R_9$ comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

In the various just described compositions, one or more of the groups $R_2$, $R_3$, $R_4$, $R_5$, $R_6$, $R_7$, $R_8$, $R_9$ or $R_{10}$ can comprise one or more halides.

In a variation of this invention, the group $R_5$ can comprise an aromatic ring so that the composition has the structure:

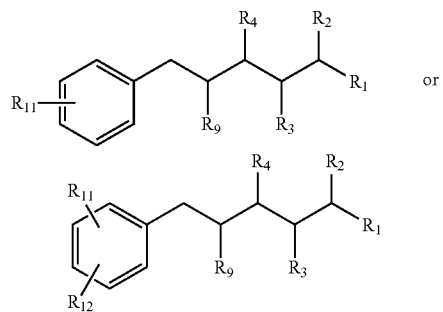

wherein $R_{11}$ comprises H, OH, a halide, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_{11}$ and $R_{12}$ independently comprise a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

In yet a different variation, this invention provides the above described composition where the group $R_{10}$ comprises an aromatic group so that the composition has the structure:

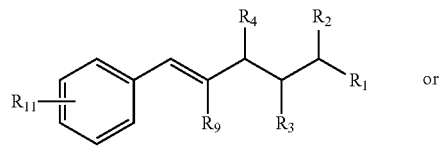

19

-continued

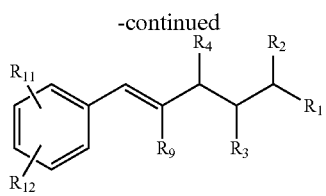

wherein $R_{11}$ comprises H, OH, a halide, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_{11}$ and $R_{12}$ independently comprise a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

In the just described compositions, the groups $R_{10}$, $R_{11}$, or both $R_{10}$ and $R_{11}$ comprise one or more halides.

It should also be appreciated that in the above compositions, the C4 atom may be asymmetric and may comprise the 4R conformation or the 4S conformation.

As in other compositions of this invention, the last described compositions can further comprise a detectable label. Such detectable labels are conventional and well known in the art. The detectable label can comprise a ligand or a fluorescent dye. In the case of the former, biotin, digoxygenin or fluorescein are contemplated and are useful. If fluorescent dyes are contemplated, a number of such dyes can be employed, including fluorescein, fluorescein isothiocyanate (FITC), 6-carboxyfluorescein (6-FAM), naphthofluorescein, rhodamine, rhodamine 6G, rhodamine X, rhodol, sulforhodamine 101, tetramethylrhodamine (TAMRA), tetramethylrhodamineisothiocyanate (TRITC), 4,7-dichlororhodamine, eosin, eosinisothiocyanate (EITC), dansyl, hydroxycoumarin, methoxycoumarin or p-(Dimethyl aminophenylazo) benzoic acid (DABCYL), cyanine dyes or derivatives, and any combinations of the foregoing.

In another embodiment for the above described compositions, the C1 atom may be asymmetric and may comprise the 1R conformation or the 1S conformation.

In these compositions just described, the heteroatom or heteroatoms can comprise S, N or O, and combinations thereof. As earlier described, the heteroatom or heteroatoms can form a number of linkages including those of the form

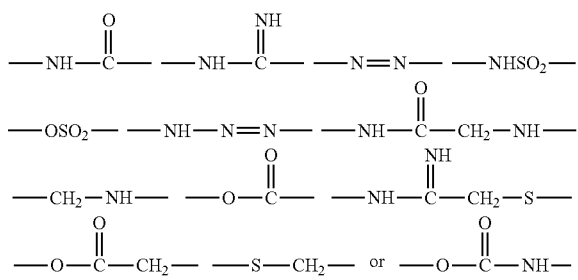

and a combination of any of the foregoing.

As in the case of other compositions of the present invention, at least two of the groups $R_1$, $R_2$, $R_3$, $R_4$ or $R_5$ can be joined together to form one or more rings. Cyclization and the formation of rings by joining R groups has been described above.

Also provided by the present invention is a composition of matter having the structure:

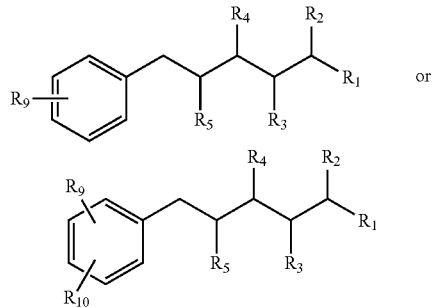

wherein $R_1$ is H or comprises O, N, S, a phosphate group or a phosphonate group, and any combination thereof; wherein $R_2$ is H, or comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_3$ is H or comprises OH, $NR_6R_7$, $N^+R_6R_7R_8$, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_6$, $R_7$ and $R_8$ independently comprise H, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_5$ is H or comprises OH, a halide, =O, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; and wherein $R_9$ and $R_{10}$ independently comprise a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

In another embodiment for the just described composition, one or more of the groups, $R_2$, $R_3$, $R_4$, $R_5$, $R_6$, $R_7$, $R_8$, $R_9$ or $R_{10}$, can comprise at least one double bond or at least one triple bond, or both at least one double bond and at least one triple bond. In yet another embodiment, the straight carbon chain, the branched carbon chain, the straight carbon chain comprising one or more heteroatoms or the branched carbon chain comprising one or more heteroatoms in $R_2$, $R_3$, $R_4$, $R_5$, $R_6$, $R_7$, $R_8$, $R_9$ or $R_{10}$ can comprise an alkyl, a substituted alkyl, an alkene, a substituted alkene, an alkyne or a substituted alkyne, and combinations of any of the foregoing. Moreover, one or more of the groups, $R_2$, $R_3$, $R_4$, $R_5$, $R_6$, $R_7$, $R_8$, $R_9$ or $R_{10}$, can comprise one or more halides.

It should also be appreciated that in these compositions, $R_3$ and $R_4$ can independently comprise the same or different R or S isomer. Moreover, $R_3$ and $R_4$ together can comprise an isomer that is 2R, 3R; 2S, 3S; 2R, 3S; or 2S, 3R. Furthermore, in these compositions, the C4 atom may be asymmetric and may comprise the 4R conformation or the 4S conformation.

These last described compositions can further comprise a detectable label, which are conventional and known in the art. Such detectable labels can comprise a ligand or a fluorescent dye. In the case of the former, biotin, digoxygenin or fluorescein are contemplated but should not be considered limiting. In the case of the latter, many fluorescent dyes are known in the art, but for the sake of illustration, the following are useful in accordance with this invention: fluorescein, fluorescein isothiocyanate (FITC), 6-carboxyfluorescein (6-FAM), naphthofluorescein, rhodamine, rhodamine 6G, rhodamine X, rhodol, sulforhodamine 101, tetramethylrhodamine (TAMRA), tetramethylrhodamineisothiocyanate (TRITC), 4,7-dichlororhodamine, eosin, eosinisothiocyanate (EITC), dansyl, hydroxycoumarin, methoxycoumarin or p-(Dimethyl aminophenylazo) benzoic acid (DABCYL), cyanine dyes or derivatives, and any combinations of the foregoing.

In other aspects for these compositions, the Cl atom may be asymmetric and comprise the 1R conformation. Alternatively, the Cl atom may be asymmetric and comprise the is conformation.

In the last described compositions of the present invention, the heteroatom or heteroatoms can comprise S, N or O, and combinations thereof. Furthermore, such heteroatom or heteroatoms can form a number of linkages, including the following list which should be considered limiting but only illustrative:

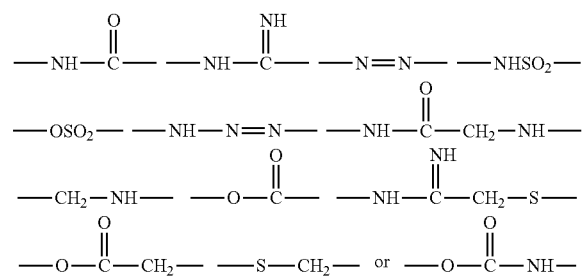

and a combination of any of the foregoing.

In these compositions described above, at least two of the groups, $R_1$, $R_2$, $R_3$, $R_4$ or $R_5$, can be joined together to form one or more rings through the cyclization of R groups using conventional methods of chemical synthesis.

This invention also provides a composition of matter having the structure:

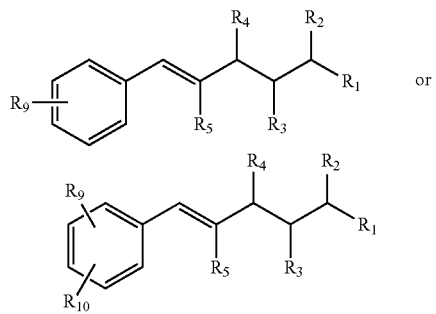

wherein $R_1$ is H or comprises O, N, S, a phosphate group or a phosphonate group, and any combination thereof; wherein $R_2$ is H, or comprises a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_3$ is H or comprises OH, $NR_6R_7$, $N^+R_6R_7R_8$, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_6$, $R_7$ and $R_8$ independently comprise H, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_5$ is H or comprises OH, a halide, =O, a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing; wherein $R_9$ and $R_{10}$ independently comprise a straight carbon chain, a branched carbon chain, a straight carbon chain comprising one or more heteroatoms, a branched carbon chain comprising one or more heteroatoms, a cyclic ring, a heterocyclic ring, an aromatic ring or a hetero-aromatic ring, and any combination of the foregoing.

In the last described composition, one or more of the groups, $R_2$, $R_3$, $R_4$, $R_5$, $R_6$, $R_7$, $R_8$, $R_9$ or $R_{10}$, can comprise at least one double bond or at least one triple bond, or both at least one double bond and at least one triple bond. Furthermore, the straight carbon chain, the branched carbon chain, the straight carbon chain comprising one or more heteroatoms or the branched carbon chain comprising one or more heteroatoms in $R_2$, $R_3$, $R_4$, $R_5$, $R_6$, $R_7$ or $R_8$ can comprise an alkyl, a substituted alkyl, an alkene, a substituted alkene, an alkyne or a substituted alkyne, and combinations of any of the foregoing. Moreover, one or more of the groups, $R_2$, $R_3$, $R_4$, $R_5$, $R_6$, $R_7$, $R_8$, $R_9$ or $R_{10}$, can comprise one or more halides.

In other embodiments for this composition, $R_3$ and $R_4$ can independently comprise the same or different R or S isomer. In a further aspect, $R_3$ and $R_4$ can together comprise an isomer that is 2R, 3R; 2S, 3S; 2R, 3S; or 2S, 3R.

As described for other compositions of the present invention, these last compositions can also comprise a detectable label which are conventional and known in the art. Such detectable labels can comprise a ligand or a fluorescent dye. In the case of the former, biotin, digoxygenin or fluorescein are contemplated but are not intended to be limiting. In the case of the latter, many fluorescent dyes are known. For purposes of illustration, these can include fluorescein, fluorescein isothiocyanate (FITC), 6-carboxyfluorescein (6-FAM), naphthofluorescein, rhodamine, rhodamine 6G, rhodamine X, rhodol, sulforhodamine 101, tetramethylrhodamine (TAMRA), tetramethylrhodamineisothiocyanate (TRITC), 4,7-dichlororhodamine, eosin, eosinisothiocyanate (EITC), dansyl, hydroxycoumarin, methoxycoumarin or p-(Dimethyl aminophenylazo) benzoic acid (DABCYL), cyanine dyes or derivatives, and any combinations of the foregoing.

The Cl atom in these compositions may be asymmetric and may comprise the 1R conformation or the 1S conformation.

In further aspects, the heteroatom or heteroatoms can comprise S, N or O, and combinations thereof. Such heteroatom or heteroatoms can form a linkage which are described in the art. For illustration purposes only, these linkages can comprise any of the following

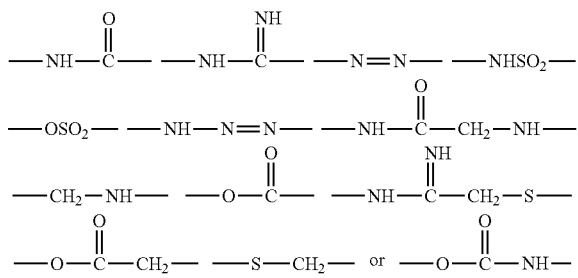

and a combination of any of the foregoing. Moreover, these linkages can take the above configuration, or they can be used in reverse or opposite configurations. In other words, the orientation can be varied and is not limited to the precise form shown above.

As described earlier, in these last compositions, at least two of the groups, $R_1$, $R_2$, $R_3$, $R_4$ or $R_5$, can be joined together to form one or more rings. Such cyclization and ring formation using R groups in the compounds and analogs can be carried out using conventional methods. The rings can be joined covalently or non-covalently.

Pharmacokinetics and Patient Management

Another important aspect of the present invention is a method for monitoring the course of pharmacokinetics of a drug after administration to a subject or patient. In this method, a drug comprising any of the compounds described above is administered to a subject or patient. The administered drug can be detected at selected intervals, thereby monitoring the course of pharmacokinetics of the drug. Such a method is useful in studying and monitoring patient management because the course and progress of the administered drug can be followed within cells, tissues, organs or the subject or patient as a whole. By attaching signaling moieties to the compounds and analogs of this invention, in vivo imaging can be carried out following the administration of the drug to detect the presence of the drug within cells of the subject or patient. Cell staining can also be carried out to locate the presence of the drug within cells of the subject or patient's sample or specimen. Radioactivity in the form of radioactively labeled drugs, i.e., compounds or analogs, can also be utilized.

Indications/Diseases

Yet another important feature of this invention is a method for treating tumors of the central nervous system. This method comprises the step of administering to a subject or patient having a tumor or tumors of the central nervous system any of the above-described compounds of the present invention. The tumors of the central nervous system can comprise various forms known in the art, including glioblastoma, and more particularly, glioblastoma multiforme (GBM). Useful in the treatment of GBM is the compound below which comprises

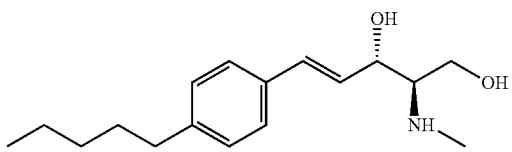 [SMILES: CCCCCc1ccc(/C=C/[C@H](O)[C@@H](CO)NC)cc1]

The above-described compounds and analogs of the present invention are useful for treatment and monitoring of a number of indications and diseases. In Ser. No. 12/387,228, filed Apr. 29, 2009 (contents incorporated by reference), the following indications and diseases are disclosed: killing or damaging cancer cells (leukemia cells, breast cancer cells, prostate cancer cells, pancreatic cancer cells, glioma cancer cells, colon cancer cells, lung cancer cells, ovarian cancer cells, melanoma cells, renal cancer cells); causing cancer cells to undergo apoptosis; inhibiting growth, metastasis and development of chemoresistance in cancer cells, treating or reducing symptoms of leukemia; increasing the ability of anticancer agent to kill cancer cells; inhibiting survival signaling in cancerous cells; attenuating immune reactivity; and reducing symptoms of multiple sclerosis.

In addition to the above-named indications and diseases, the compounds and analogs of the present invention are useful for diseases associated with neural cell death or muscular cell death, such as Parkinson's disease, Alzheimer's disease, amniotropic lateral sclerosis and muscular dystrophy, AIDS, fulminant hepatitis, and diseases linked to degeneration of the brain (e.g., Creutzfeld-Jakob disease, retinitis pigmentosa and cerebellar degeneration, myelodysplasis (e.g., aplastic anemia, ischemic diseases such as myocardial infarction and stroke, hepatic diseases such as alcoholic hepatitis, hepatitis B and hepatitis C, joint diseases such as osteoarthritis, atherosclerosis, alopecia, damage to the skin due to UV light, lichen planus, atrophy of the skin, cataract and graft rejections. These compounds and analogs described herein are applicable to immunopathology caused by influenza virus. Other diseases include those implicating caveolar endocytosis, plasma membrane microdomain formation, transmembrane signaling or integrin function (e.g., inflammatory diseases including cancer, MS, prothrombotic risk, ulcerative colitis and renal disease). These might occur as the result of infection by certain bacteria, fungi or viral species, e.g., SV40 virus.

Among other uses of the compounds and analogs of the present invention are inhibition of angiogenesis in tumors, modulation of the immune system by altering lymphocyte trafficking for treatment of autoimmune diseases or prolongation of allograft transplant survival, and preventing, inhibiting or treating neuropathic pain. Also within the scope of use for the present compounds and analogs are the treatment or prevention of disorders or syndromes including cell proliferative disorders, e.g., cancer, ischemia or restenosis. The compounds and analogs of the present invention can also be used to screen for a modulator of disorders/syndromes including the aforementioned cell proliferative disorders (cancers, ischemia or restenosis).

These compounds and analogs are applicable to treating or attenuating complications in subjects or patients suffering from trauma or sepsis.

Other pathological conditions can be addressed through the use and application of the present compounds and analogs, including cardiovascular diseases, diabetes, stroke, autoimmune and inflammatory diseases, allergic diseases such as dermatitis, T helper-1, related diseases, chronic obstructive pulmonary disease, asthma, cancer and neurodegenerative disorders, some of which have already been described above.

The following examples are offered by way of illustration and not by way of limitation to the present invention.

Example 1: Synthesis of BML-258

The compound described and used below, BML-258, was synthesized according to the following protocol and procedures.

BML-258 Synthetic Protocol

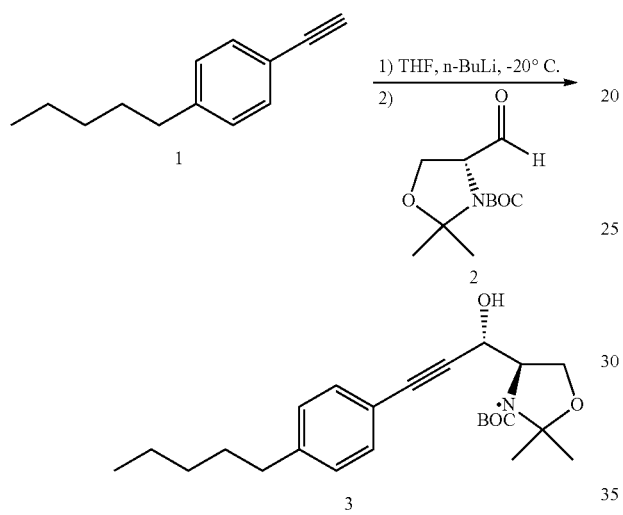

To 4-n-pentylphenylacetylene 1 (3.343 g, 0.01776 mol) in 65 mL dry THF at −20° C. under an atmosphere of N2 was added n-BuLi (10.2 mL of 1.6M in hexanes, 0.01628 mol) dropwise. The reaction mixture was stirred at −20° C. for 2 hours. Methyl (R)-(+)-3-(t-butoxycarbonyl)-2,2-dimethyl-4-oxazolidinecarboxylate 2 (3.393 g, 0.01480 mol) in 25 mL dry THF was added via cannula/N2. The reaction was stirred overnight at −20° C. overnight. TLC (20% ethyl acetate/hexanes) indicated completeness of reaction. The mixture was diluted with Et2O and carefully washed with water and brine. Flash column chromatography (12% Ethyl acetate/hexanes, silica gel) yielded 4.50 g (73%) of a mixture of erythro and threo products. Preparative HPLC (Dynamax Si, 15% Ethyl acetate/hexanes, 260 nm) yielded 3.71 g erythro 3 and 0.49 g threo. 1H NMR (CDCl3) erythro: 7.34-7.32 (d, 2H), 7.12-7.09 (d, 2H), 5.19-5.16 (d, 1H), 4.73-4.70 (d, 1H), 4.26-3.96 (m, 3H), 2.61-2.56 (t, 2H), 1.62 (s, 3H), 1.60-1.50 (m, 2H), 1.54 (s, 3H), 1.50 (s, 9H), 1.34-1.27 (m, 4H), 0.91-0.86 (t, 3H).

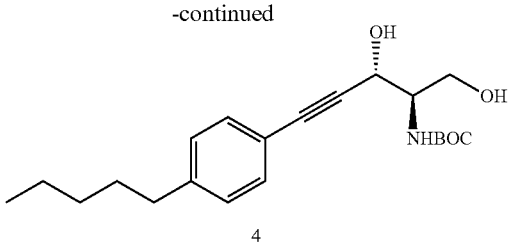

To oxazolidine 3 (3.48 g, 0.00814 mol) in 100 mL MeOH was added Amberlyst-15 (200 mg). The reaction was stirred overnight at room temperature. TLC (30% Ethyl acetate/hexanes) indicated completeness of reaction. The mixture was filtered and flash chromatographed (5% MeOH/methylene chloride, silica gel) to give 2.44 g (79%) of aminoalcohol 4. 1H NMR (CDCl3): 7.34-7.32 (d, 2H), 7.12-7.09 (d, 2H), 5.45-5.38 (d, 1H), 4.88-4.82 (m, 1H), 4.25-4.19 (m, 1H), 3.91- 3.80 (m, 2H), 3.26-3.23 (d, 1H), 2.61-2.56 (t, 2H), 1.63-1.54 (m, 2H), 1.49 (s, 9H), 1.35-1.26 (m, 4H), 0.91-0.86 (t, 3H).

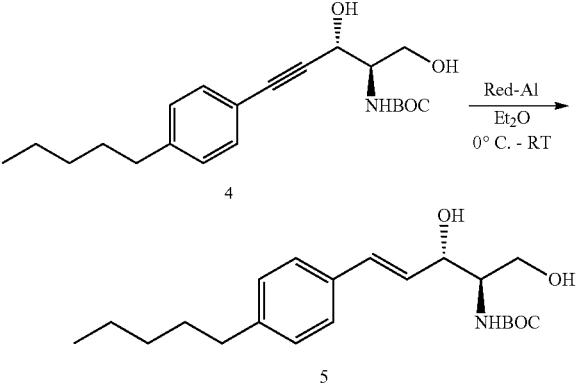

To alkyne 4 (2.44 g, 0.00646 mol) in 125 mL dry Et2O at 0° C. under an atmosphere of N2 was added Red-Al (9.85 mL of 65 wt % in toluene, 0.03232 mol) dropwise. The reaction was allowed to warm to room temperature following the addition and was stirred for 36 hours. TLC (40% Ethyl acetate/hexanes) indicated completeness of reaction. The reaction was cooled to 0° C. and carefully quenched with 15% NaOH solution. This mixture was stirred vigorously until both layers were clear (45 min). The layers were separated and the aqueous layer extracted with chloroform (3×). The combined organic layers were washed with 15% NaOH, water and brine. Flash chromatography (gradient of 5% MeOH/methylene chloride to 20% MeOH/methylene chloride+1% NH4OH, silica gel) yielded 1.76 g (72%) of trans alkene 5. 1H NMR (CDCl3): 7.31-7.29 (d, 2H), 7.15-7.12 (d, 2H), 6.70-6.65 (d, 1H, J=16 Hz), 6.26-6.18 (dd, 1H, J=16 Hz), 5.35- 5.32 (d, 1H), 4.55-4.49 (m, 1H), 4.03-3.96 (m, 1H), 3.80-3.68 (m, 2H), 2.83-2.79 (d, 1H), 2.61-2.56 (t, 2H), 1.65-1.55 (m, 2H), 1.44 (s, 9H), 1.34-1.25 (m, 4H), 0.91-0.86 (t, 3H).

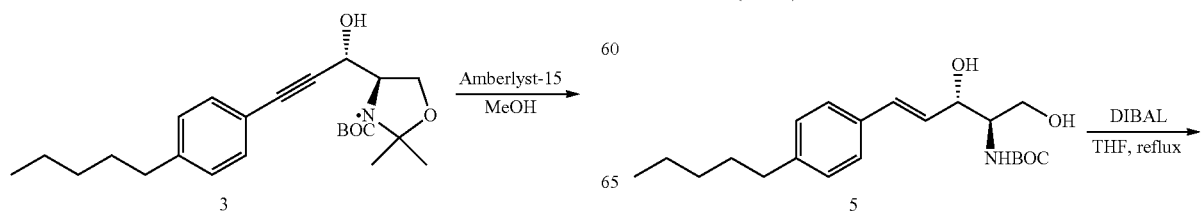

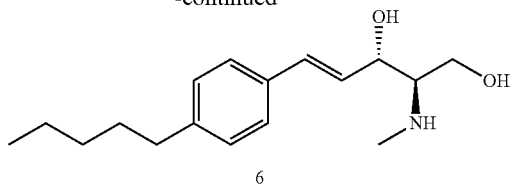

To BOC-alkene 5 (0.350 g, 0.00092 mol) in 20 mL dry THF under an atmosphere of N₂ was carefully added DIBAL (9.22 mL of 1M in THF, 0.00922 mol) at room temperature. Following the addition, the reaction was brought to reflux. After 24 hours of reflux, the mixture was cooled to room temperature and an additional 5.0 mL DIBAL solution (0.00500 mol) was added. Reflux was resumed for another 24 hours. The reaction was cooled to 0° C. and carefully quenched with water (0.60 mL), 15% NaOH (0.60 mL) and water again (1.50 mL). THF (50 mL) was added and the mixture stirred vigorously for 15 minutes. Na₂SO₄ (2 g) and celite (2 g) were then added and stirring was continued for 30 minutes while warming to room temperature. The mixture was filtered and the filter cake extracted with copious THF. Flash chromatography (gradient of 2% MeOH/methylene chloride to 10% MeOH/methylene chloride+0.75% NH₄OH) yielded 0.187 g (73%) of amine 6. 1H NMR (CDCl₃): 7.31-7.29 (d, 2H), 7.15-7.12 (d, 2H), 6.68-6.63 (d, 1H, J=16 Hz), 6.22-6.14 (dd, 1H, J=16 Hz), 4.51-4.47 (m, 1H), 3.80-3.74 (m, 3H), 2.61-2.56 (t, 2H), 2.50 (s, 3H), 2.40-2.10 (broad, 2H), 1.65-1.55 (m, 2H), 1.34-1.25 (m, 4H), 0.91-0.86 (t, 3H). HRMS (MH+): Calc. −278.2120, Found −278.2119.

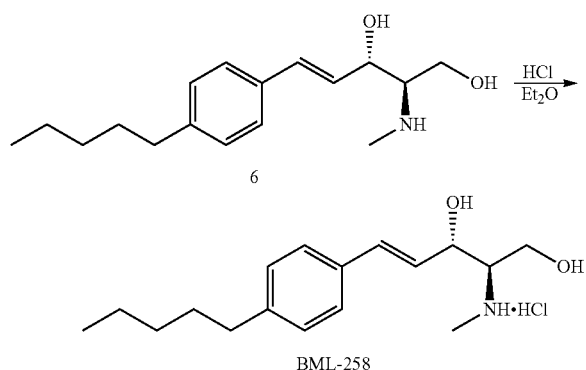

To amine 6 (0.335 g, 0.00121 mol) in 15 mL dry Et₂O at 0° C. was added 3.0 mL of 1M HCl/Et₂O. A white precipitate formed immediately. After stirring for 15 minutes at room temperature, the precipitate was filtered and washed with Et₂O to give 0.325 g (89%) of BML-258. 1H NMR (DMSO): 8.75-8.50 (bd, 2H), 7.38-7.34 (d, 2H), 7.19-7.15 (d, 2H), 6.65-6.60 (d, 1H, J=16 Hz), 6.30-6.22 (dd, 1H, J=16 Hz), 5.84-5.82 (m, 1H), 5.30-5.25 (m, 1H), 4.60-4.54 (m, 1H), 3.76-3.72 (m, 2H), 3.18-3.10 (m, 1H), 2.64 (s, 3H), 2.56-2.50 (t, 2H), 1.60-1.50 (m, 2H), 1.34-1.23 (m, 4H), 0.90-0.85 (t, 3H).

SK1-I, (2R,3S,4E)-N-methyl-5-(4'-pentylphenyl)-2-aminopent-4-ene-1,3-diol (BML-258), was synthesized by BIOMOL International (Plymouth Meeting, Pa.) as described in Example 1. Sphingosine and N,N-dimethylsphingosine were obtained from BIOMOL. [γ-³²P]ATP (3000 Ci/mmol) was purchased from Perkin Elmer (Boston, Mass.). Boc-D-FMK (BOC), Z-VAD-FMK (ZVAD) and etoposide were from EMD Biosciences (San Diego, Calif.). Terminal deoxynucleotidyl transferase Br-dUTP nick end labeling (TUNEL) kit for flow cytometry was from Sigma Aldrich (St. Louis, Mo.). TUNEL kit for immunohistochemistry was from Roche Applied Science (Indianapolis, Ind.). FITC-4 labeled annexin V/propidium iodide staining kit for apoptosis was from BD Biosciences (San Jose, Calif.).

Example 2: General Procedure for Synthesis of SK1-I Analogs from Alkynes

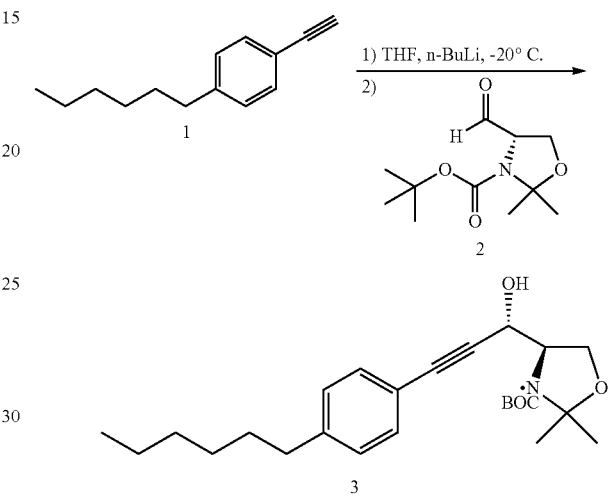

To alkyne, 1, (1.2 eq) in dry THF at −20° C. was added n-BuLi (1.1 eq. of 1.6M hexanes) drop wise. The reaction was stirred at −20° C. for 2 hours. The aldehyde, 2, (1 eq., dissolved in dry THF, was added drop wise. The reaction was placed in a −20° C. freezer overnight. After approximately 18 hours, the reaction was diluted with diethyl ether and washed with water and brine. Flash column chromatography yielded a mixture of erythro and threo products. The pure erythro compound, 3, was isolated via HPLC.

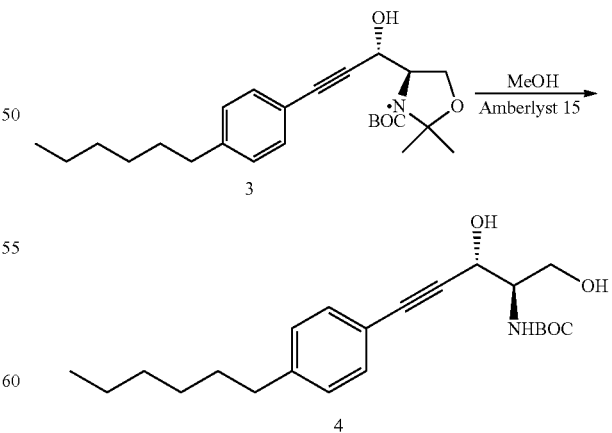

The resulting erythro oxazolidine, 3, was stirred with Amberlyst 15 resin in methanol overnight to remove the acetonide protecting group. Flash column chromatography yielded the Boc protected aminodiol, 4.

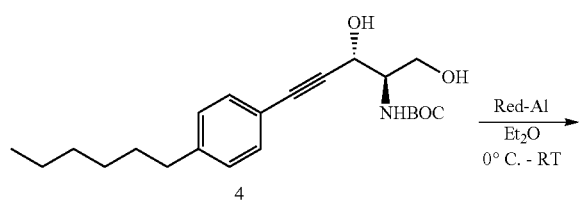

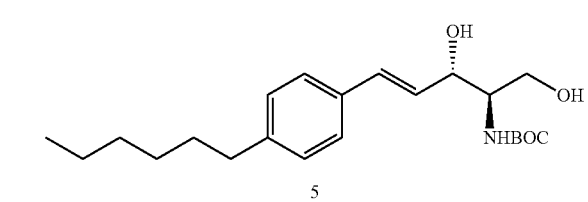

To alkyne aminodiol, 4, (1 eq.) in diethyl ether at 0° C. was added Red-Al (5 eq. of 65 wt % in toluene) drop wise. The reaction was allowed to warm to room temperature overnight. After approximately 18 hours of reaction, the mixture was cooled to 0° C. and quenched with 15% NaOH (5 eq). Flash column chromatography yielded the alkenyl aminodiol 5.

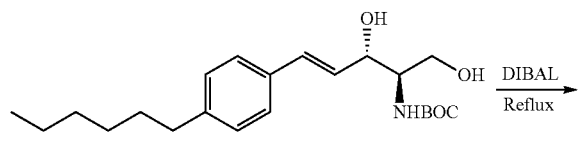

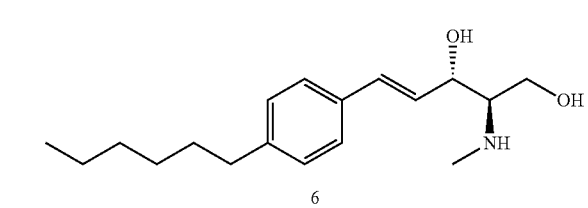

To alkenylaminodiol, 5, (1 eq) in dry THF at 0° C. was added DIBAL (10 eq. of 1M/THF) drop wise. Following the addition, the reaction was gradually warmed to room temperature and then refluxed overnight. After 24 hours of reaction, the mixture was cooled to 0° C. and quenched successively with water (4 eq), 15% NaOH (4 eq) and water (10 eq). Flash column chromatography yielded the target compound, 6.

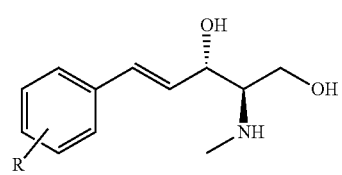

Analogs of general structure, 7, are prepared using the appropriately substituted alkyne following the general procedure. R=3,4-dimethoxy; 4-phenyl; 3-pentyl.

Synthesis of SK1-I Analogs with Various N-Alkyl Groups

The appropriately substituted BOC-protected SK1-I analog is synthesized using the general procedure outlined previously.

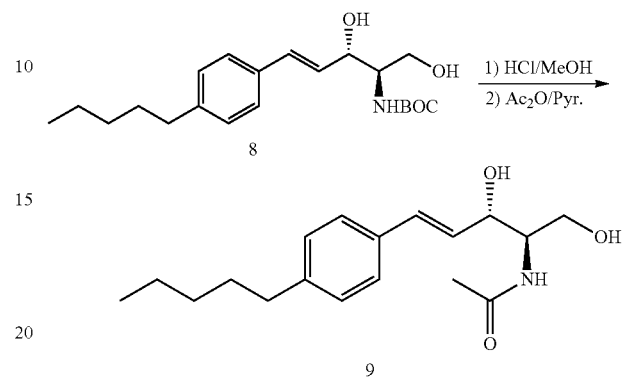

To BOC-protected SKI-1, 8, (1 eq) in methanol at 0° C. is bubbled hydrogen chloride gas until the mixture is saturated. The reaction is stirred at room temperature until TLC indicates completeness of reaction. The resulting solution is evaporated to dryness and dissolved in dry pyridine. Acetic anhydride (1 eq.) is added and the reaction stirred at room temperature until complete by TLC. Flash chromatography yielded the monoacetyl derivative, 9.

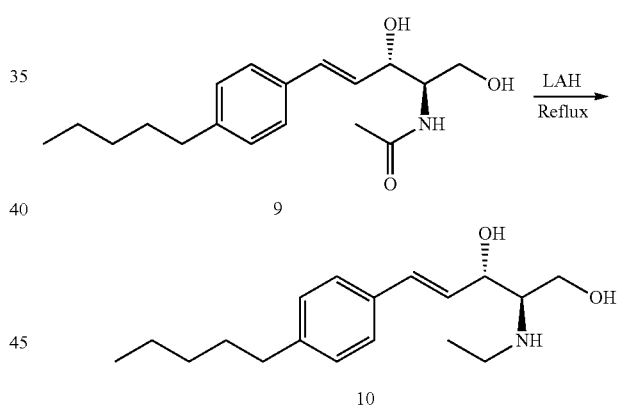

To N-acetyl-SKI-1, 9, (1 eq) in dry THF at 0° C. is added Lithium Aluminum Hydride (4 eq. of 1M/THF). Following the addition, the reaction mixture is warmed to room temperature and then refluxed overnight. The mixture was then cooled to 0° C. and quenched successively with water (4 eq), 15% NaOH (4 eq) and water (10 eq). Flash column chromatography yielded the target alkylamine, 10.

Synthesis of Di-N-Alkyl SK1-I Analogs

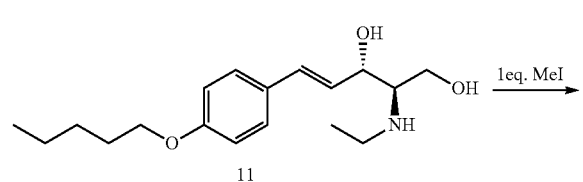

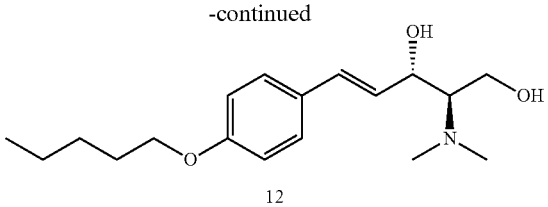

12

To SK1-I, 11, (1 eq) in dry THF at room temperature was added methyl iodide (1 eq). The reaction was stirred until TLC indicated complete reaction. Flash column chromatography yielded the desired compound, 12.

Materials and Methods

Cell culture. U373-MG and LN229 human glioblastoma cells (ATTC, Manassas, Va.) were cultured in DMEM supplemented with 5% FCS. Primary human non-established glioblastoma GBM6 cells were kindly provided by Dr. C. David James and were passaged as tumors in nude mice and subcultured for 1 week following isolation from tumors in media containing 2% FCS to prevent growth of contaminating rodent fibroblasts and then cultured in 5% FCS as described (Yacoub et al., *Mol Cancer Ther* 7:314-329, 2008). LN229 cells were transfected with H2B-EGFP plasmid and stable colonies were isolated following selection with 1 mg/ml of G418. LN229-H2B-EGFP cells were passaged as tumors as described above.

Xenograft tumors. Adult male NCI nu/nu mice were purchased from NCI (Frederick, Md.). All animal studies were conducted in the Animal Research Core Facility at VCU School of Medicine in accordance with the institutional guidelines. LN229 cells ($1\times10^6$) were injected in the flanks (4 sites per mouse). Palpable tumors appeared in about one week. Five days later, when tumors reached 3-4 mm in diameter, mice were randomly separated into 2 groups and injected i.p. with saline or SK1-I (10 mg/kg) every other day. Tumor measurements were made with calipers, and tumor volume was calculated using the formula: ($\pi\times$[length in millimeters]$\times$[width in millimeters]2)/6. At the end of the experiment, the animals were euthanized and the tumors removed, fixed in formalin and embedded in paraffin, or frozen in liquid nitrogen.

Intracranial LN229 xenograft tumors. Adult female NCI nu/nu mice were anesthetized and LN229-H2B-EGFP cells ($2.5\times10^4$ in 1 µl PBS) were stereotactically implanted in the putamen region (1 mm anterior and 2.5 mm lateral to the Bregma at the depth of 3.5 mm at a rate of 0.1 µl/min). Mice were monitored for recovery until complete wakening. 20 days after implantation, mice were injected i.p. with SK1-I (20 mg/kg in PBS) every other day. Mice were observed daily following tumor implantation and were euthanized on reaching a moribund state.

Details about infection of cells with recombinant adenoviruses, cell proliferation and cell death assays, immunohistochemistry, immunocytochemistry, and confocal microscopy are presented in the information below.

Results

SK1-I Potently Inhibits Growth and Survival of Human Glioblastoma Cells

Figure 1B:
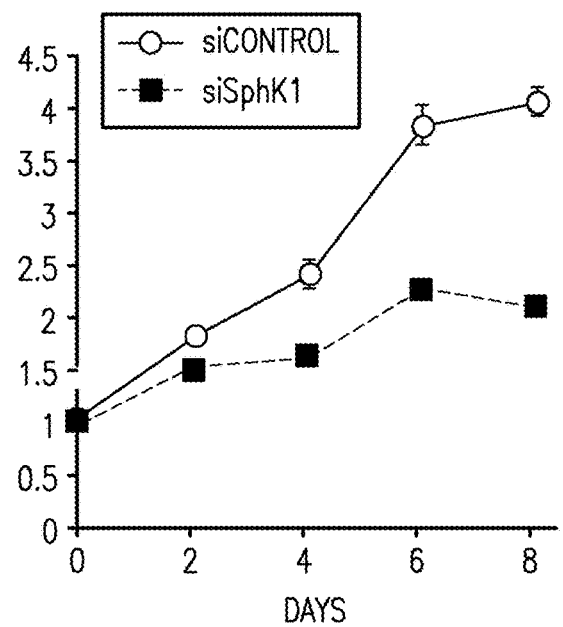
Figure 1C:
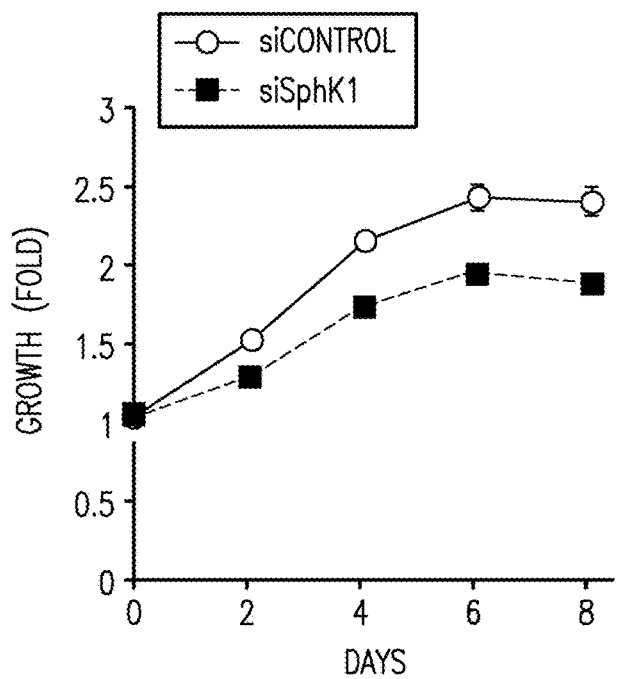
Figure 1D:
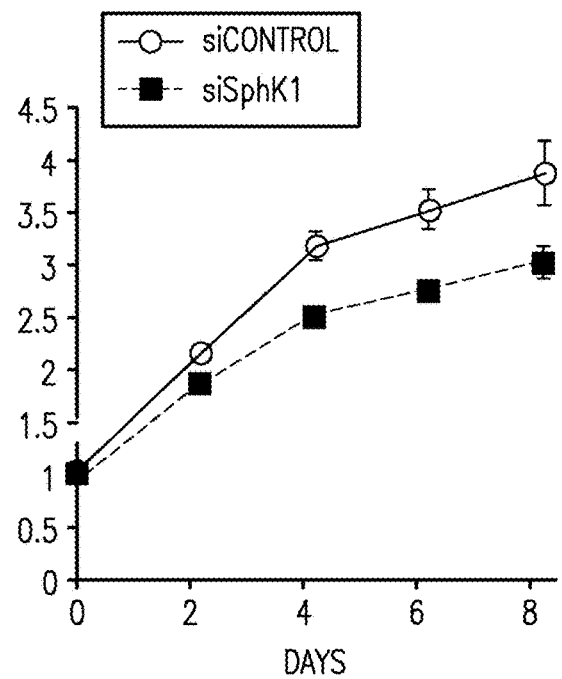
Figure 1E:
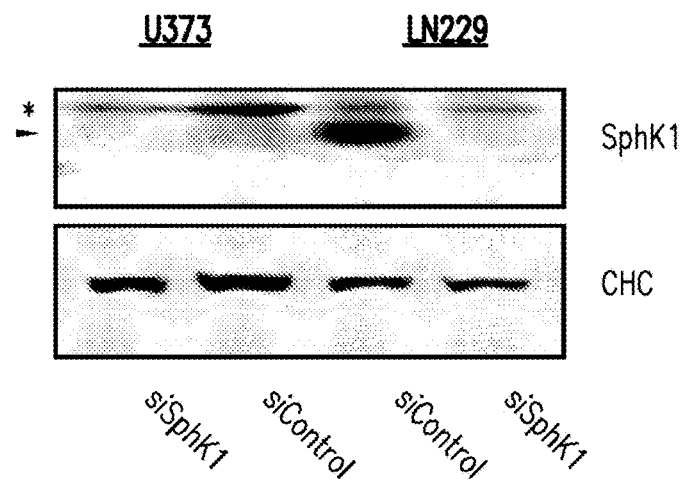
Figure 1F:
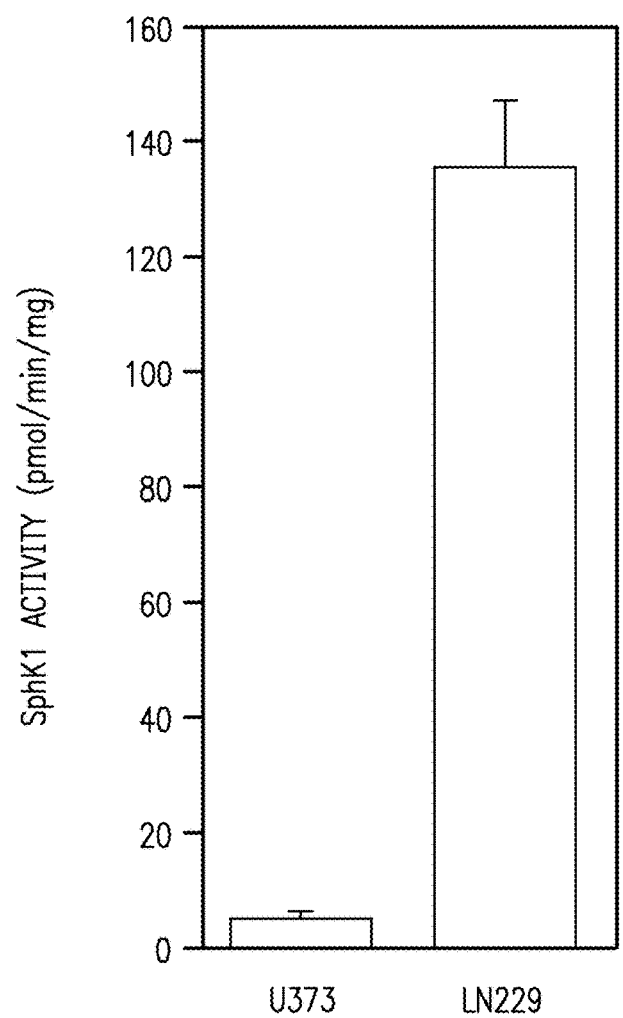

Previous studies demonstrated that S1P and SphK1, the kinase that produces it, play critical roles in growth and survival of glioblastoma cells (Van Brocklyn et al., *J Neuropathol Exp Neurol* 64:695-705, 2005; Van Brocklyn et al., *Cancer Lett* 181:195-204, 2002; and Radeff-Huang et al. *J Biol Chem* 282:863-870, 2007). In agreement, downregulation of SphK1 expression decreased growth of both U373 cells, which express mutated PTEN, and LN229 cells expressing wild type PTEN, in serum-free medium (FIGS. 1A, 1C) as well as in the presence of serum (FIGS. 1B, 1D), which greatly enhanced their growth. Expression of SphK1 in these cells was drastically reduced by siRNA targeted to a specific sequence of SphK1 mRNA, as detected by western blotting with a polyclonal anti-SphK1 antibody (FIG. 1E). The greater sensitivity of U373 cells to downregulation of SphK1 might be due to much lower SphK1 expression and enzymatic activity compared to LN229 cells (FIG. 1F).

The first SphK1-specific inhibitor, SK1-I, was recently described (Paugh et al., *Blood* 283:3365-3375, 2008). SK1-I inhibited growth of both U373 (FIGS. 1G, 1H) and LN229 (FIGS. 1I, 1J) cells in a dose-dependent manner. A significant inhibitory effect was observed at 3 µM. SK1-I at 10 µM strongly inhibited growth of U373 and LN229 cells cultured in the absence of serum (FIGS. 1G, 1I). SK1-I was less effective when cells were cultured in the presence of serum, which contains multiple growth factors and S1P. However, even in the presence of serum, within 2-4 days, there were severe reductions in cell numbers after treatment with 10 µM SK1-I (FIGS. 1H, 1J).

SK1-I Inhibits Migration and Invasion of Glioblastoma Cells

Figure 8C:
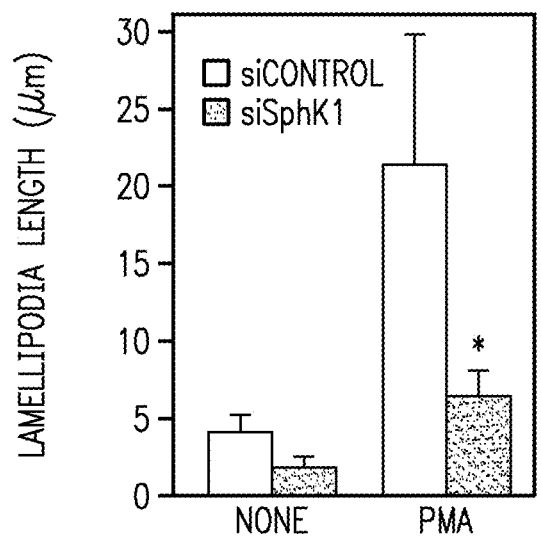
Figure 8D:
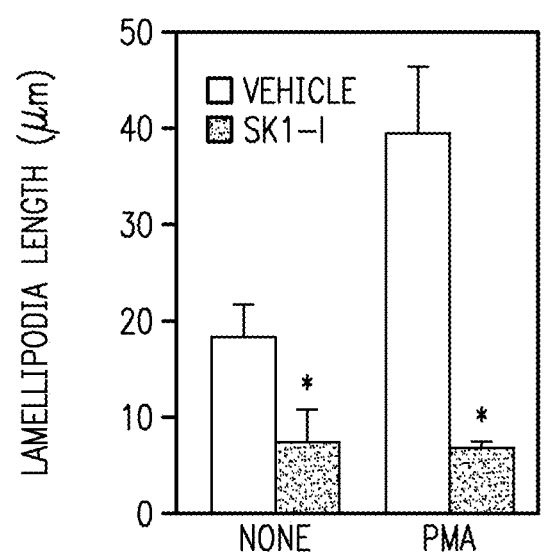

As S1P and SphK1 have been shown to regulate migration and invasion of glioblastoma cells (Lepley et al. *Cancer Res* 65:3788-3795, 2005; Young et al. *Exp Cell Res* 313:1615-1627, 2007; Van Brocklyn et al. *Cancer Lett* 199:53-60, 2003; and Malchinkhuu et al. *Oncogene* 24:6676-6688, 2005), and SphK1 regulates actin cytoskeletal dynamics (Kusner et al. *J Biol Chem* 282:23147-23162, 2007) and lamellipodia formation (Maceyka et al. *Mol Cell Biol* 28:5687-5697, 2008), it was of interest to examine whether inhibition of SphK1 by SK1-I correlated with changes in reorganization of the actin cytoskeleton. F-actin was distributed across unstimulated U373 cells, as revealed by staining with Alexa488-conjugated phalloidin (FIG. 8A). In response to PMA the actin cytoskeleton underwent robust reorganization, and more F-actin was condensed at the leading edge within structures termed lamellipodia (FIG. 8A). In agreement with a previous study with human macrophages (Kusner et al., *J Biol Chem* 282:23147-23162, 2007), downregulation of SphK1 markedly reduced the number of actin-rich lamellipodia produced by treatment with PMA (FIGS. 8A, 8C). Similarly, inhibiting SphK1 with SK1-I dramatically reduced PMA-stimulated F-actin reorganization at the leading edge and formation of lamellipodia and induced disassembly of filopodia (FIGS. 8B, 8D).

Figure 9A:
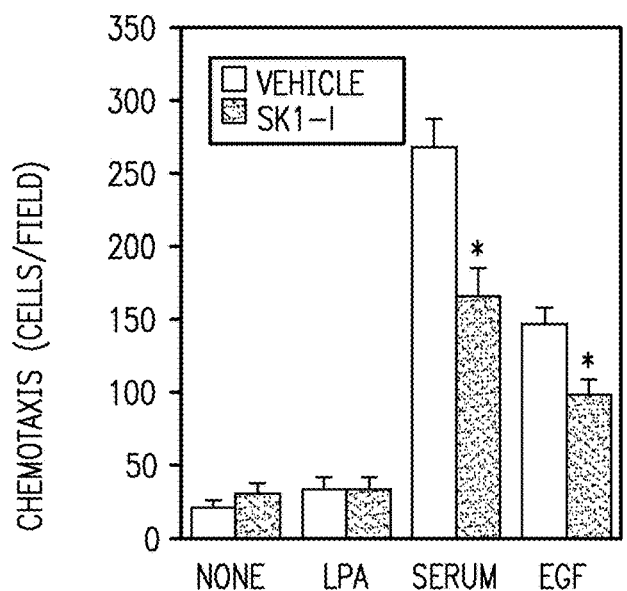
FIGS. 9A-9B.

These results support the notion that SphK1 activity is required for actin filament dynamics (Kusner et al. *J Biol Chem* 282:23147-23162, 2007). Therefore, the effect of SK1-I on migration and invasion of glioma cells was next examined. Directed motility (chemotaxis) of U373 cells toward serum or EGF in Boyden chamber assays was reduced by SK1-1 (FIG. 9A). Similarly, chemotaxis of LN229 cells, which show much greater rates of basal and stimulated migration toward serum and EGF than U373 cells, is also significantly inhibited by SK1-I (FIG. 2A). SK1-I also drastically inhibited chemotaxis of LN229 cells toward lysophosphatidic acid (LPA), another serum-borne lysophospholipid that has been shown to be a potent chemoattractant for certain glioblastoma cell lines, including LN229 cells (Malchinkhuu et al. *Oncogene* 24:6676-6688, 2005) (FIG. 2A). LPA, serum, and EGF also stimulated in vitro invasion of LN229 cells (FIG. 2B), determined by their ability to invade the basement membrane matrix Matrigel, which was also greatly attenuated by SK1-I (FIG. 2B).

SK1-I Reduces Basal and Stimulated Akt Phosphorylation

Figure 2C:
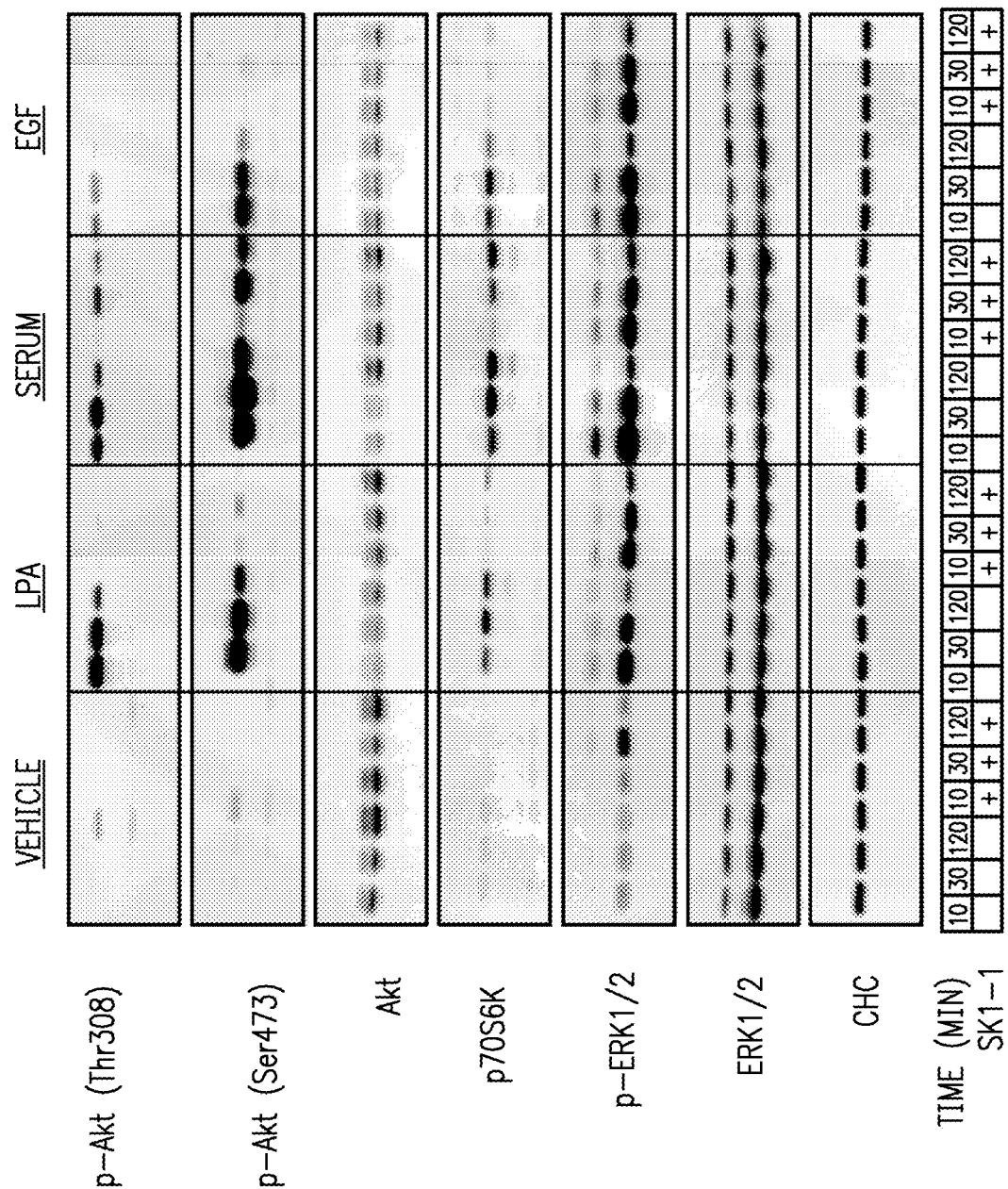
Figure 9B:
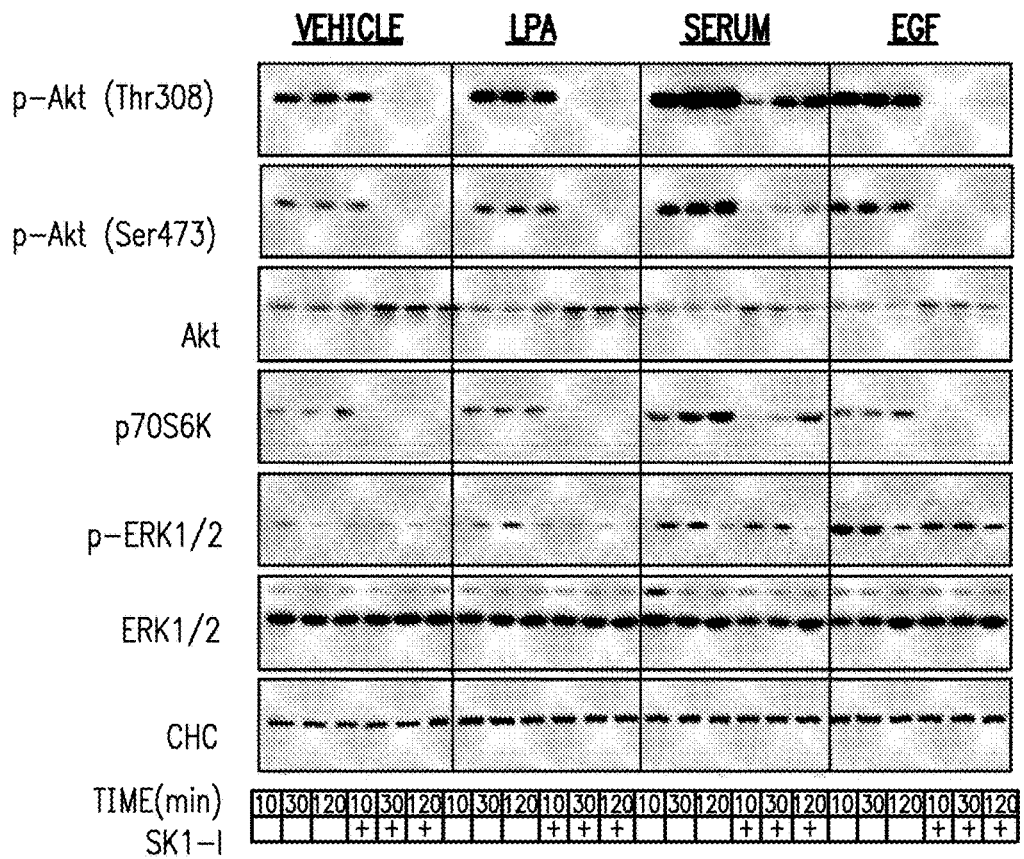

S1P-induced glioblastoma cell proliferation is greatly suppressed by inhibition of ERK1/2 and PI3K/Akt pathways (Van Brocklyn et al. *Cancer Lett* 181:195-204, 2002). Thus, it was of interest to examine the effects of SK1-I on these signaling pathways. We utilized phospho-specific antibodies to examine phosphorylation of Akt at Thr308 in the activation loop and at Ser473 at the C-terminus, which are required for full activation (Haas-Kogan et al. *Curr. Biol* 8:1195-1198, 1998). Consistent with their expression of wild-type PTEN, LN229 cells have low basal Akt phosphorylation, which was rapidly increased by serum, LPA, and EGF, to a lesser extent (FIG. 2C). SK1-I reduced Akt activation induced by all three stimuli. Treatment with SK1-I for only 20 minutes markedly suppressed phosphorylation of Akt at both Thr308 and Ser473 (FIG. 2C). SK1-I also reduced activation of p70S6K (Thr389), a downstream target of Akt. In sharp contrast, although serum, LPA, and EGF stimulated ERK1/2, in these short-term assays, SK1-I did not significantly affect stimulated ERK1/2 phosphorylation at Thr202/Tyr204 (FIG. 2C). Moreover, although Akt is active in U373 cells because, like many human gliomas they express a nonfunctional mutant form of PTEN that does not inhibit the PI3K/Akt pathway (Haas-Kogan et al. *Curr Biol* 8:1195-1198, 1998), SK1-I reduced their basal Akt phosphorylation at Thr308 and Ser473 (FIG. 9B). A significant inhibitory effect was observed within 20 min (FIG. 9B), which lasted for at least 24 hours (data not shown). As expected, serum and EGF enhanced phosphorylation of Akt, whereas SK1-I reduced it (FIG. 9B). The inhibitory effect of SK1-I on Akt phosphorylation was not due to its degradation as there were no significant reductions in total Akt levels after treatment with SK1-I. However, SK1-I did not reduce EGF- and serum-induced ERK1/2 activation in both U373 (9B) and LN229 cells (FIG. 2C).

Figure 2D:
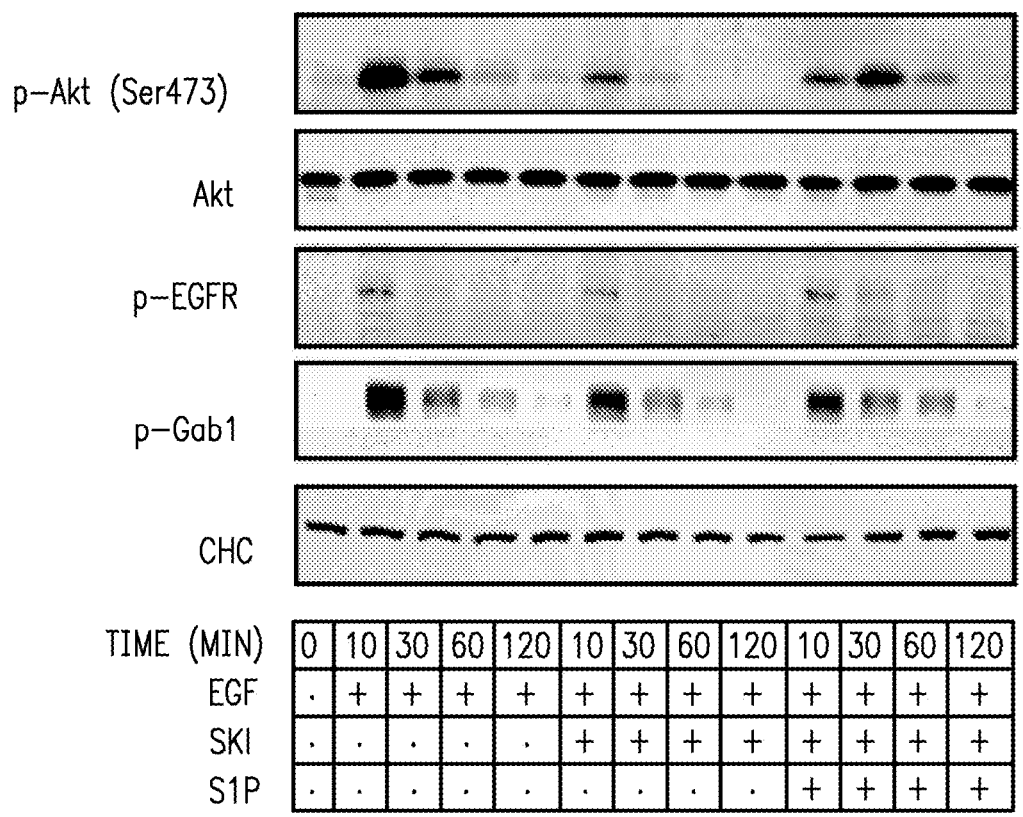

To substantiate that the effects of SK1-I were due to its ability to inhibit SphK1, S1P add-back experiments were carried out. Consistent with the reduction in levels of S1P by SK1-I (FIG. 3A), inhibition of EGF-induced Akt phosphorylation by SK1-I was reversed by addition of SIP (FIG. 2D). EGF has been shown to activate PI3K/Akt by phosphorylating growth factor receptor-bound protein 2 (Grb2)-associated binder 1 (Gab 1) (Mattoon et al. *BMC Biol* 2:24-35, 2004). However, SK1-I did not affect EGF-induced tyrosine phosphorylation of EGFR or of Gab1 (FIG. 2D), indicating that SK1-I did not directly interfere with EGFR activation. Thus, the SphK1 inhibitor SK1-I specifically inhibits phosphorylation and activation of Akt in GBM cells in a S1P-dependent manner.

Figures 3A, 3B, 3C:
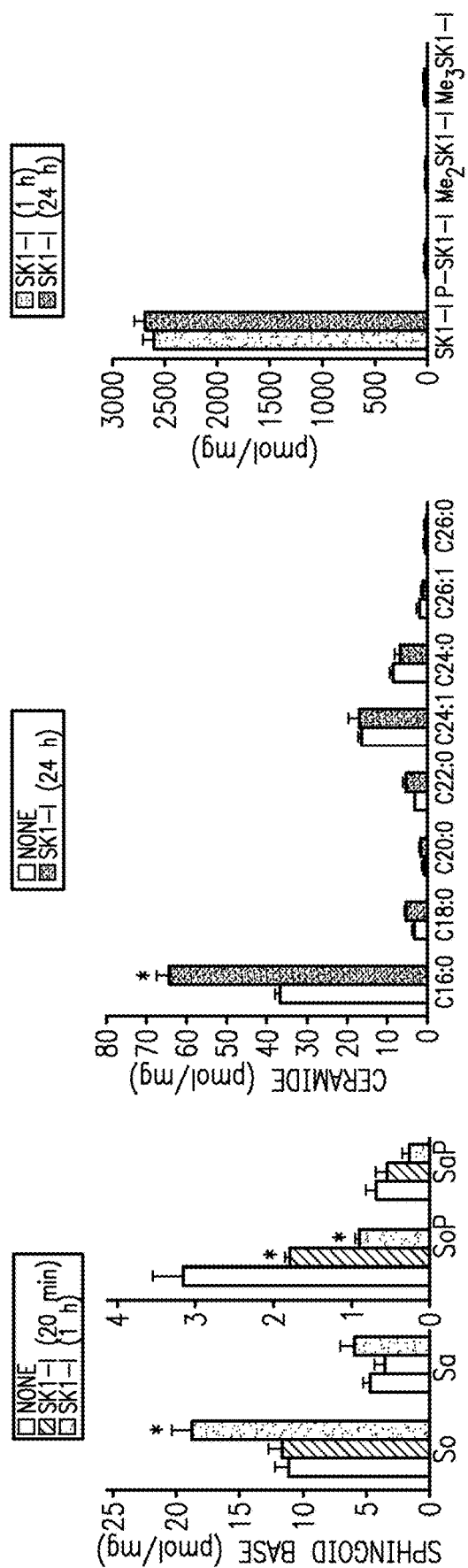
FIGS. 3A-3F.

Because downregulation of SphK1 not only decreases S1P, it also increases ceramide levels (Maceyka et al. *J Biol Chem* 280:37118-37129, 2005; Pchejetski et al. *Cancer Res* 65:11667-11675, 2005; Taha et al. *FASEB J* 20:482-484, 2006; Berdyshev et al. *Cell Signal* 18:1779-1792, 2006), it was of interest to examine the effects of inhibition of SphK1 with SK1-I on these sphingolipid metabolites that have been reported to have opposing effects on cell growth and apoptosis (Cuvillier et al. *Nature* 381:800-803, 1996; and Hannun et al. *Nat Rev Mol Cell Biol* 9:139-150, 2008). There was a significant reduction in S1P levels within 20 min after addition of SK1-I (FIG. 3A), which correlated with the rapid inhibition of Akt phosphorylation. Furthermore, within 1 h after addition of SK1-I, S1P levels were dramatically decreased by 70% that was accompanied by an increase in sphingosine levels without major changes in ceramide levels (FIG. 3A). However, after 24 h of treatment with SK1-I, ceramide levels increased markedly, particularly pro-apoptotic C16-ceramide. Unlike safingol (L-threo-dihydrosphingosine) (Coward et al. *Autophagy* 5:184-193, 2009), a pan SphK inhibitor, only less than 1% of SK1-I was converted to the tri-N-methyl metabolite after 24 h (FIG. 3A) and no other metabolites were detected. Moreover, in contrast to its structural analogue, the immunosuppressant drug FTY720, SK1-I is not readily phosphorylated, ruling out potential actions through S1P receptors.

Inhibition of c-Jun N-Terminal Kinase Attenuates SK1-I-Induced Cell Death

In agreement with many previous studies showing that downregulation of SphK1 and ceramide elevation are associated with increased apoptosis (reviewed in (Hannun et al. *Nat Rev Mol Cell Biol* 9:139-150, 2008; Cuvillier, O. *Expert Opin Ther Targets* 12:1009-1020, 2008; and Shida et al. *Curr Drug Targets* 9:662-673, 2008), treatment with SK1-I induced apoptosis of LN229 cells as demonstrated by increased cleavage of PARP (FIG. 10A), a substrate for caspase-mediated proteolysis during apoptosis, increased fragmented and condensed nuclei (FIG. 10B), and increased DNA strand breaks detected by TUNEL staining (FIG. 10C). Moreover, SK1-I markedly suppressed long-term survival of LN229 cells in clonogenic assays (FIG. 10D).

Sphingolipid metabolites, S1P versus sphingosine and ceramide, usually have opposing effects on Akt and the stress-related c-Jun NH2-terminal kinase (JNK) pathways (Cuvillier et al. *Nature* 381:800-803, 1996; and Hannun et al. *Nat Rev Mol Cell Biol* 9:139-150, 2008). Concomitant with the inactivation of the cytoprotective Akt pathway, exposure of LN229 cells to SK1-I was accompanied by delayed activation of JNK (FIG. 10B), without affecting p38 MAPK (data not shown). Increased phosphorylation of JNK after addition of SK1-I was accompanied by enhanced phosphorylation of its substrates, the transcription factors c-Jun (Ser63/73) and ATF-2 (Thr71) (FIG. 3B).

Figure 3D:
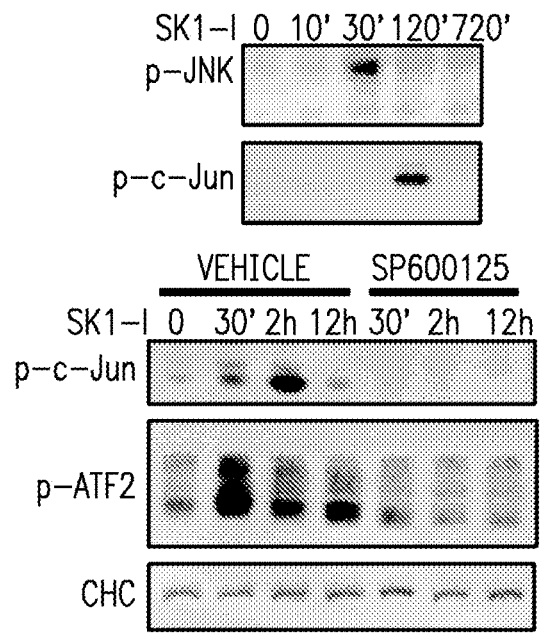
Figure 3E:
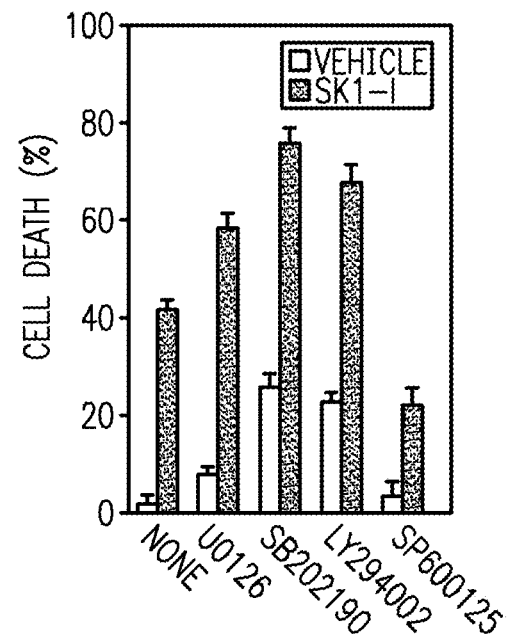
Figure 3F:
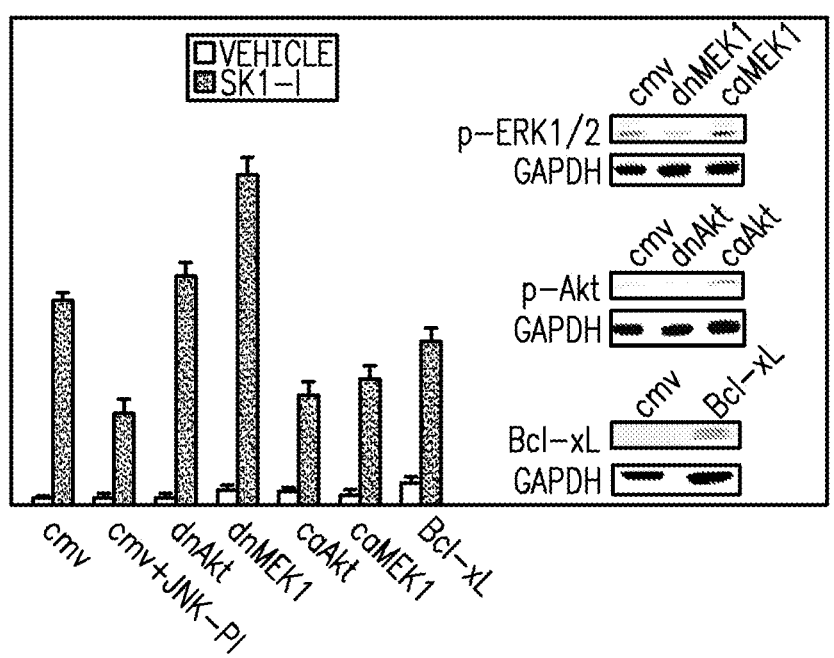

The output of ERK1/2 and Akt signaling versus JNK signaling represents a key homeostatic mechanism that in many cells regulates the balance between cell survival and cell death processes (Xia et al. *Science* 270:1326-1231, 1995). Thus, the effects of a variety of agents that perturb these signaling pathways on SK1-I mediated lethality was next examined. Inhibition of MEK1/2, PI3K, and p38 by U0126, LY294002, SB202190, respectively, enhanced SK1-I lethality, whereas inhibition of JNK by SP600125 markedly attenuated the effects of SK1-I in both U373 and LN229 cells (FIG. 3E and data not shown). As expected, SP600125 efficiently blocked JNK activation, as demonstrated by inhibition of c-Jun and ATF-2 phosphorylation (FIG. 3B). Even at 1 µM, a concentration believed to specifically inhibit JNK without having non-specific effects on other kinases, SP600125 markedly reversed SK1-I-induced lethality (FIG. 3C). The importance of the INK pathway using a specific INK peptide inhibitor was further examined. The INK peptide inhibitor blocks the activation domain of INK and prevents phosphorylation of c-Jun. This peptide also significantly reversed the cytotoxic effects of SK1-I (FIG. 3D), whereas the control peptide was ineffective. Similarly, expression of dominant-negative MEK1 also enhanced SK1-I-induced LN229 cell death, while dominant-negative Akt did not (FIG. 3F). Moreover, expression of constitutively-activated Akt or MEK1, or expression of Bcl-xL, suppressed cell death induced by SK1-I (FIG. 3F).

Effect of SK1-I on Primary Non-Established Glioblastoma

Figure 4A:
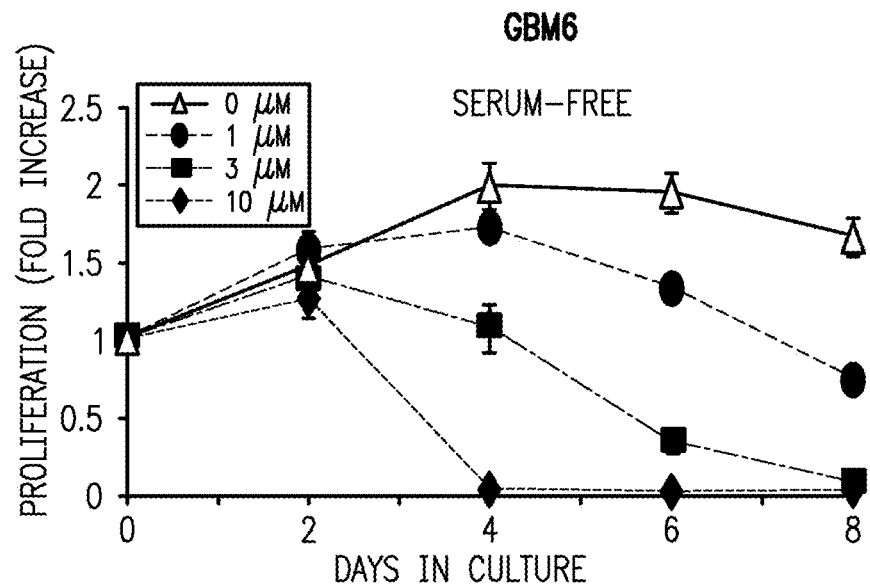
FIGS. 4A-4D.
Figure 4B:
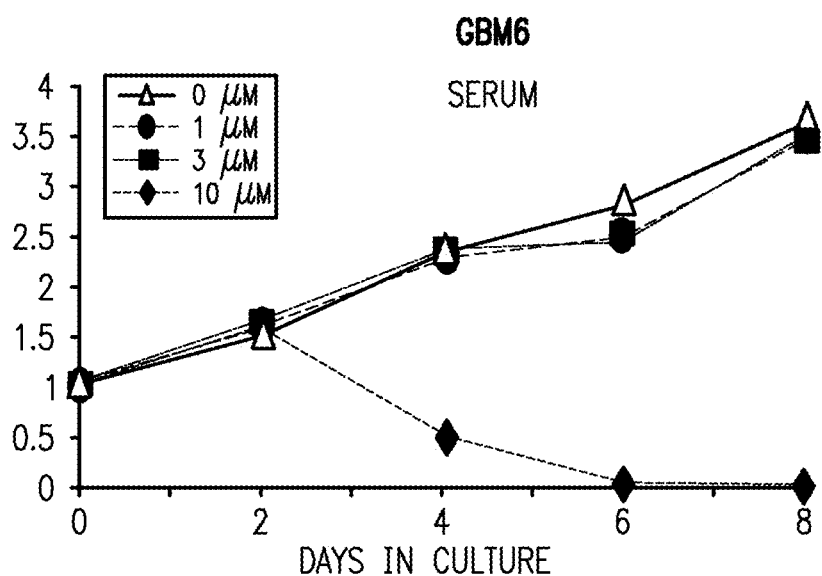
Figures 4C, 4D:
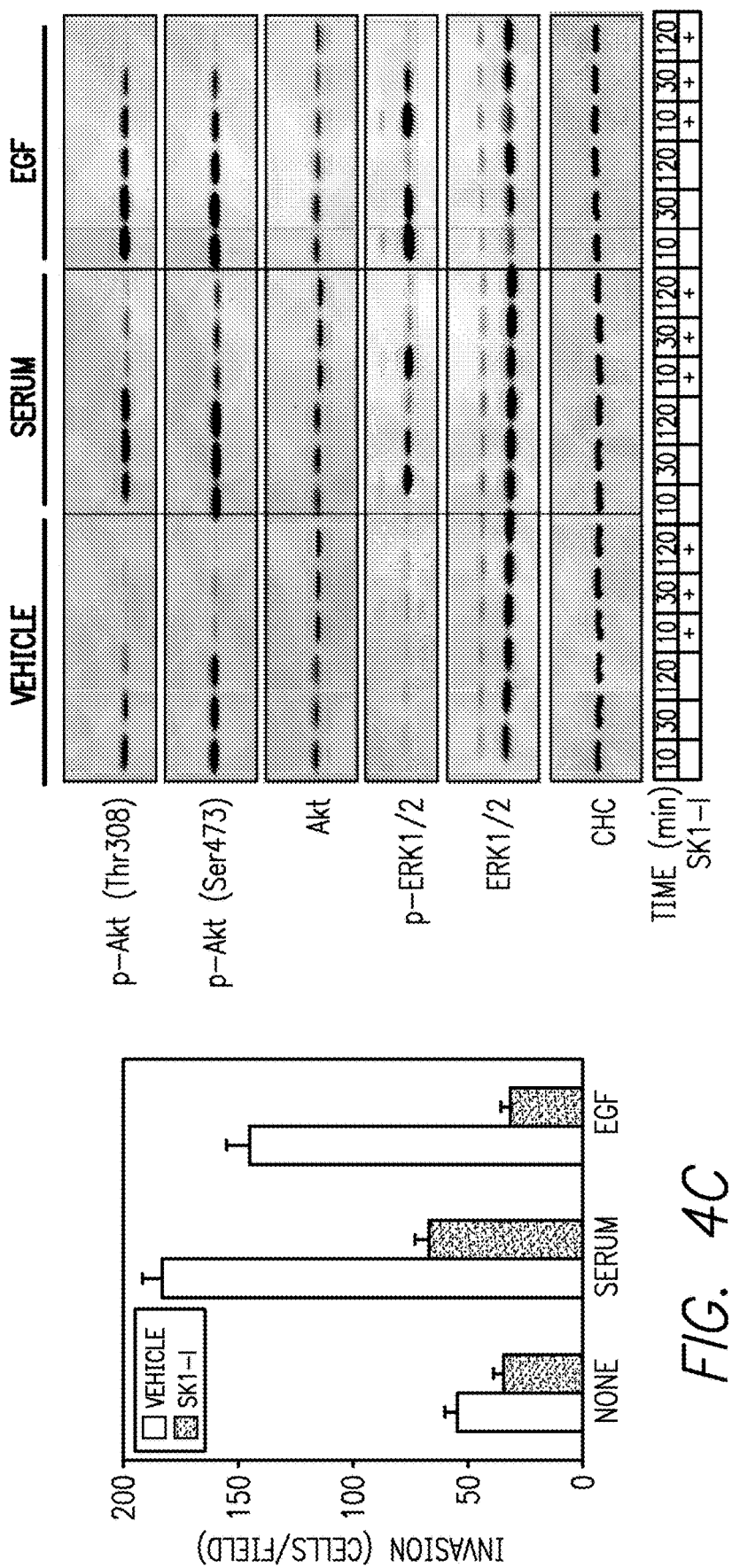

Observations with SK1-I to primary non-established human GBM6 glioblastoma cells was expanded. GBM6 glioblastoma cells have been shown to produce invasive, diffuse tumors in the brains of mice (Giannini et al. *Neuro-oncol* 7:164-176, 2005; and Yacoub et al. *Cancer Biol Ther* 7:917-933, 2008). GBM6 express mutant p53, wild-type PTEN, and EGFRvIII, a constitutively activated mutant form of EGFR (Yacoub et al. *Cancer Biol Ther* 7:917-933, 2008; and Yacoub et al. *Cancer Biol Ther* 3:739-751, 2004). Similar to LN229 and U373 cells, growth of GBM6 cells was greatly reduced by SK1-I (FIG. 4A). In the absence of serum there was a dose-dependent effect of SK1-I and significant growth inhibition was observed at a concentration as low as 1 µM (FIG. 4A). Moreover, as with the glioblastoma cell lines, 10 µM SK1-I markedly reduced growth of GBM6 in the presence of serum (FIG. 4B). SK1-I also suppressed serum- and EGF-induced invasion of GBM6 (FIG. 4C). Similar to the effects on the established glioblastoma cell lines, SK1-I reduced basal and serum- and EGF-stimulated phosphorylation of Akt shortly following treatment, without affecting pERK1/2 levels (FIG. 4D).

SK1-I Reduces Tumor Growth in Mice

Figure 5A:
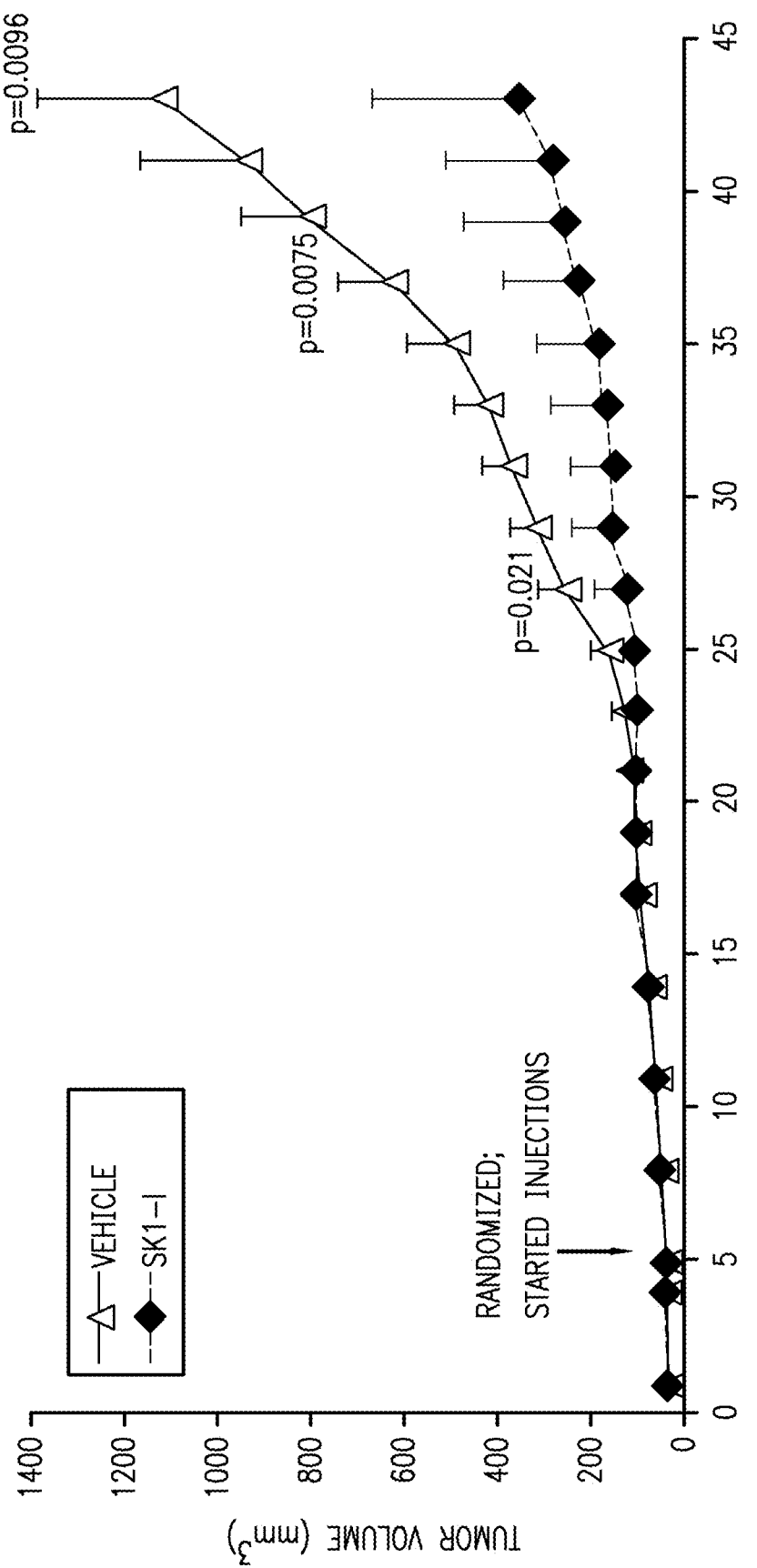
FIGS. 5A-5C.
Figure 5C:
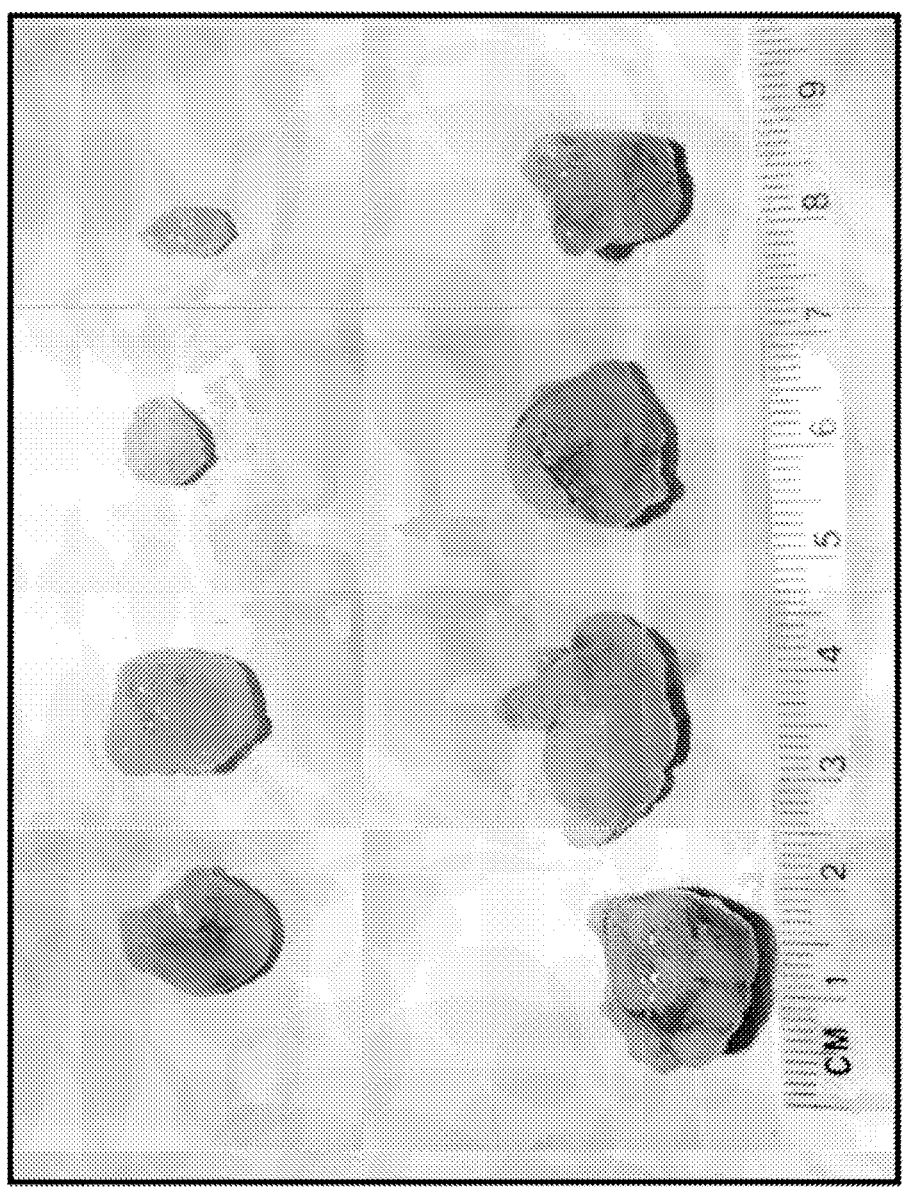
Figure 5B:
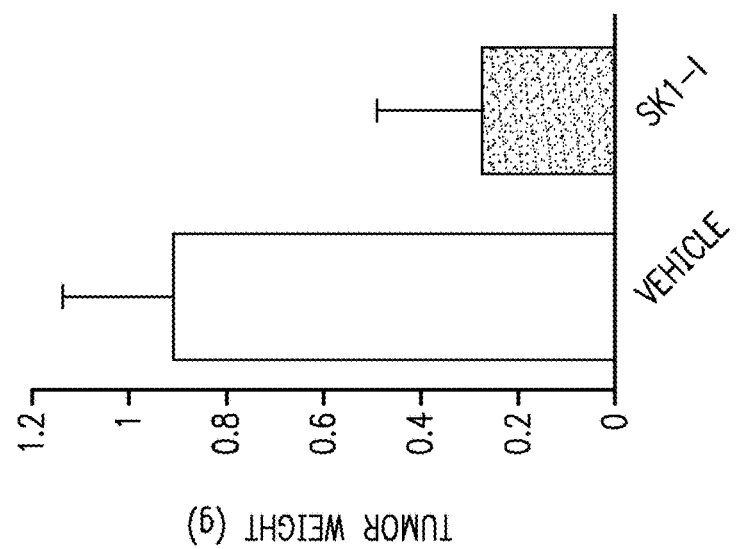
Figure 6:
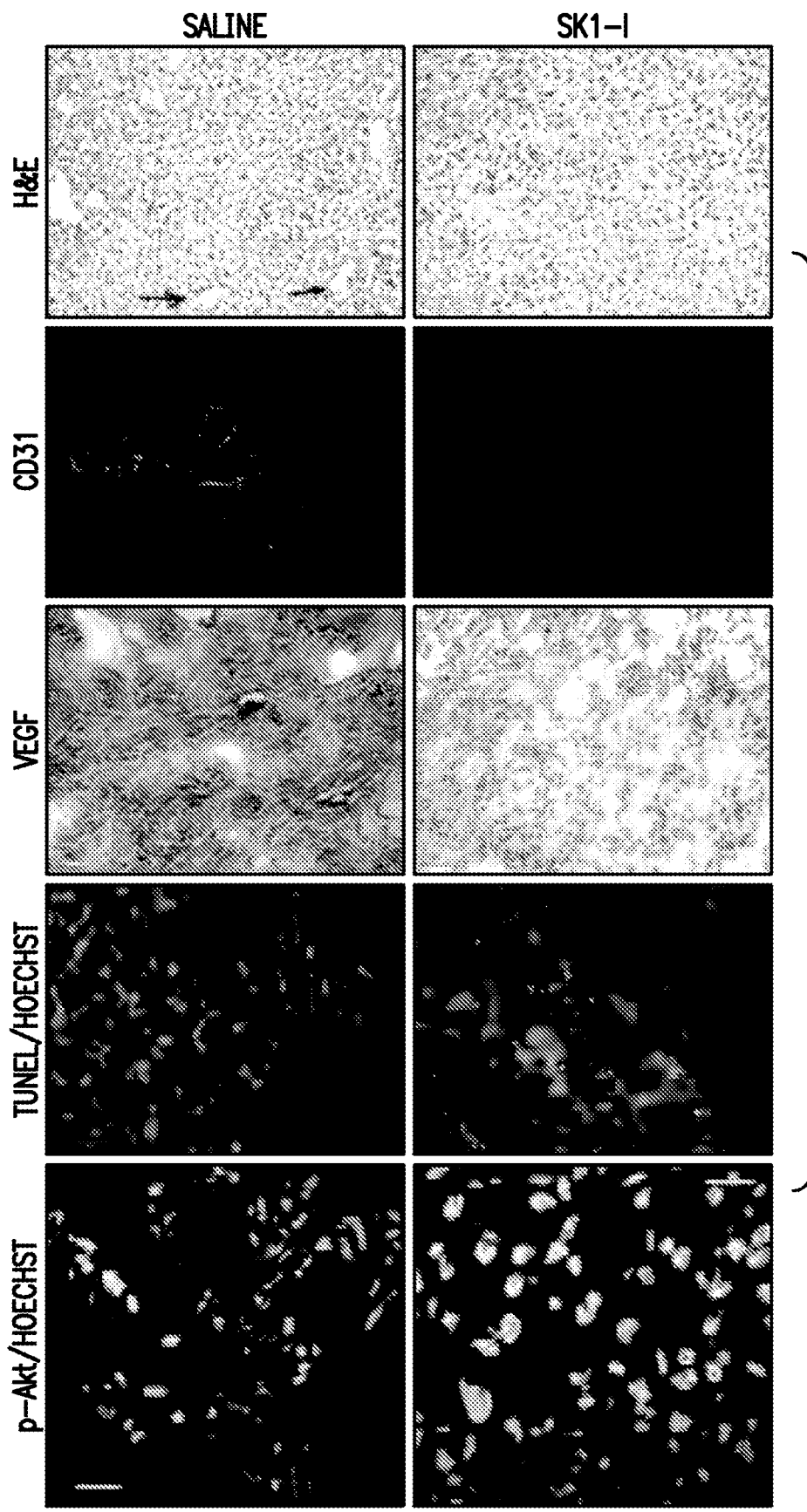
FIG. 6 shows decreased vascularization, reductions in blood vessel density, greatly reduced VEGF expression, increased numbers of TUNEL positive apoptotic tumor cells, and markedly decreased levels of phosphorylated Akt in tumors of mice treated with SK1-I as compared to vehicle treated controls.

Encouraged by these findings, the effect was examined of SK1-I on subcutaneous tumor growth of LN229 cells, which are fairly invasive and grow phenotypically similar to invasive gliomas in situ (Nakamizo et al. *Cancer Res* 65:3307-3318, 2005). Tumors appeared as palpable masses about one week after subcutaneous injection of one million cells in the flank of a mouse (FIG. 5A). Five days later, when the tumor size could be reliably measured (3-4 mm in diameter), animals were randomized and SK1-I was injected intraperitoneally every other day at a dose of 10 mg/kg. Tumors in control animals showed significant increases in volume as early as day 27, and growth accelerated thereafter. Statistical analysis (single factor ANOVA) revealed significantly smaller tumors in the SK1-I treatment group (FIG. 5A). After 43 days, animals had to be sacrificed due to the tumor burden in control mice. Tumors were excised, weighed, and histology examined. In addition to the tumor volume and size (FIGS. 5A, 5C), SK1-I treatment reduced tumor weight by almost 4-fold (FIG. 5B) and decreased vascularization in tumors, as shown by hematoxylin and eosin staining (FIG. 6). Similar reductions in blood vessel density were observed by staining with antibodies to the mouse-specific endothelial cell marker CD31 (FIG. 6). In agreement, immunohistochemistry for VEGF also revealed elevated expression of this angiogenic factor in vehicle treated tumors that was greatly reduced in SK1-I treated mice (FIG. 6). The disruption of tumor cyto-architecture by SK1-I was accompanied by increased numbers of TUNEL positive apoptotic tumor cells (FIG. 6). In agreement with attenuation of Akt phosphorylation in GBM cells by SK1-I, immunostaining for phosphorylated Akt in tumors was markedly decreased by treatment with SK1-I (FIG. 6).

SK1-I Enhances Survival of Mice with LN229 Orthotopic Tumors

Figure 7A:
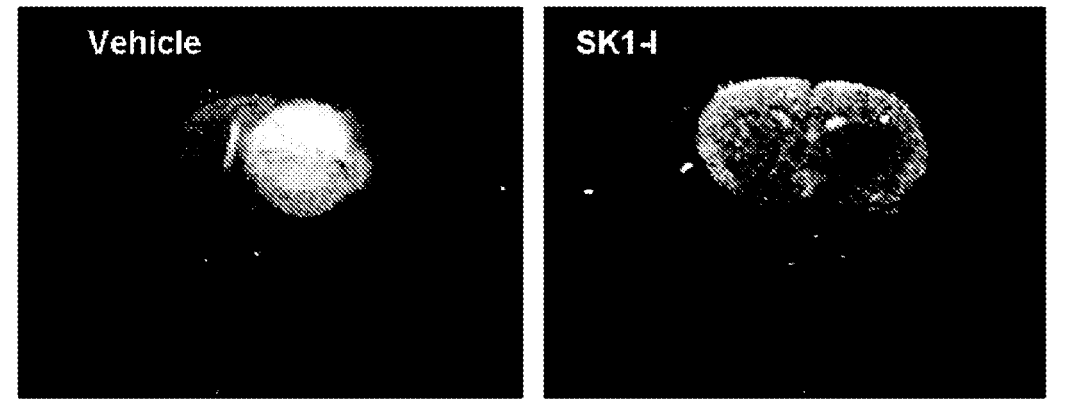
Figure 7B:
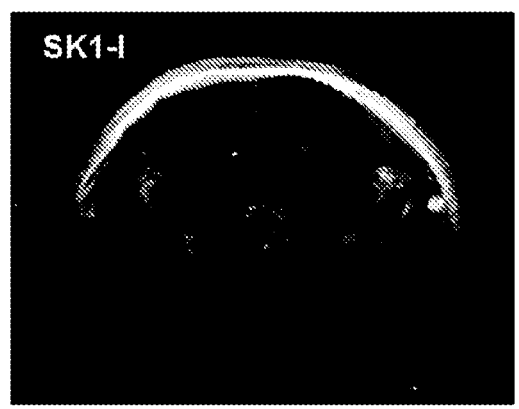

It was of interest to also examine whether SK1-I was effective in the more clinically relevant orthotopic model of intracranially implanted LN229 cells. On the basis of trial growth rate analyses, intraperitoneal treatment with SK1-I was initiated at day 20 after intracranial implantation of GFP-labeled LN229 cells when the tumors would be established and the mice would be expected to be asymptomatic. Animals in the vehicle treated group began to show symptoms of tumor burden at day 40 and were euthanized on reaching a moribund state between day 43 and 49 (FIG. 7C). None of the SK1-I treated mice showed any symptoms at this point and SK1-I administrations was then halted (FIG. 7C). At day 48, T2W MRI revealed the presence of a large tumor in the right hemisphere of vehicle treated mice (FIG. 7A), while no tumors were evident in SK1-I treated mice (FIG. 7A). Gadolinium enhancement revealed a small tumor in the brain of this SK1-I treated mouse at the site of the injection (FIG. 7B). Moreover, visualization of GFP-labeled LN229 cells in intracranial tumor sections showed significantly fewer invading cells and noticeable areas of necrosis in the middle of the tumors from SK1-I treated animals compared to vehicle treated animals (FIG. 7D). Kaplan-Meier survival analysis of intracranial glioblastoma xenografts showed significant survival benefit from SK1-I administration compared to vehicle control animals (FIG. 7C), indicating that SK1-I was remarkably efficacious in the brain even when administered intraperitoneally.

Discussion

Currently available therapies only minimally improve the prognosis of GBM patients and new therapeutic targets are desperately needed. Accumulating evidence suggests that SphK1 is an attractive new target. SphK1 message and protein levels are upregulated in GBM (Van Brocklyn et al. *J Neuropathol Exp Neurol* 64:695-705, 2005) and in astrocytoma tissues compared to adjacent normal brain (Li et al. *Clin Cancer Res* 14:6996-7003, 2008). Patients whose tumors were among the highest one-third with regard to SphK1 expression survived a median of 102 days, whereas those within the lower two-thirds survived a median of 357 days (Van Brocklyn et al. *J Neuropathol Exp Neurol* 64:695-705, 2005). High expression of SphK1 was shown to be a predictor of poor prognosis for astrocytoma patients (Li et al. *Clin Cancer Res* 14:6996-7003, 2008).

Here targeting SphK1 with SK1-I has been shown to suppress proliferation of several human glioblastoma cell lines, including U373, LN229, U87, and U118 cells as well as non-established GBM6 cells. SK1-I also potently induced apoptosis and inhibited invasion of these cells. Similar to the effects of SK1-I, downregulation of SphK1 expression has been shown to reduce glioblastoma cell growth, survival, migration, and invasion (Van Brocklyn et al. *J Neuropathol Exp Neurol* 64:695-705, 2005). SK1-I was effective in GBM that are mutant for PTEN or p53 or have a constitutively activated form of EGFR. This is particularly important since more than 80% of GBMs show strong Akt activation, many due to lost or mutated PTEN. Activation of EGFR is also a critical pathogenetic event, with amplifications, mutations, or rearrangements commonly observed (Wen et al. *N Eng J Med* 359:492-507, 2008). SK1-I also showed significant antitumor activity in vivo, inducing GBM tumor cell apoptosis and reducing tumor vascularization.

The mechanisms by which inhibition of SphK1 by SK1-I so profoundly reduces proliferation and survival of GBM in vitro and inhibits tumor growth in vivo is now beginning to become unraveled. SK1-I rapidly suppresses phosphorylation of Akt and its targets p70S6K and GSK3□, and thus interferes with signaling through the Akt pathway, which is frequently activated in gliomagenesis (Wen et al. *N Eng J Med* 359:492-507, 2008). This inhibition by SK1-I is not due to a direct effect on Akt, as it did not inhibit Akt activity in an in vitro kinase assay (Paugh et al. *Blood* 112:1382-1391, 2008). It is also well accepted that S1P produced by activation of SphK1 is released from cells and stimulates its receptors that are linked to activation of Akt. Indeed, the reduction of S1P levels by SK1-I is rapid and could contribute to decreased phosphorylation of Akt. The effects of SK1-I may not be mediated solely by reduction of "inside-out signaling" by S1P but also by reduction of intracellular S1P. These results are consistent with previous reports showing that SphK1 and intracellular S1P are critical for Akt activation and cell proliferation independently of S1P receptors (Radeff-Huang et al. *J Biol Chem* 282:863-870, 2007; and Oliviera et al. *J. Biol Chem* 278:46452-46460, 2003). Moreover, in 1321N1 glioblastoma cells, DNA synthesis and cyclin D expression was increased in a SphK1- and Akt-dependent manner independently of S1P receptors (Radeff-Huang et al. *J Biol Chem* 282:863-870, 2007). In agreement, overexpression of SphK1 promotes cell survival and growth even in cells devoid of functional S1PRs (Olivier et al., ibid.). Similarly, overexpression of SphK1 is a S1P receptor-independent oncogenic event in progression of erythroleukemia that involves activation of Akt (Le Scolan et al. *Blood* 106:1808-1816, 2005). In agreement with previous results in leukemia cells (Paugh et al. *Blood* 112:1382-

1391, 2008), SK1-I not only inhibited S1P production in glioma cells, it also increased levels of its pro-apoptotic precursor ceramide that has been shown to cause growth inhibition and apoptosis by inhibiting Akt (Hannun et al. *Nat Rev Mol Cell Biol* 9:139-150, 2008). Thus, biphasic inhibition of Akt is likely due to a rapid decrease in intracellular S1P and later sustained increases in ceramide. Furthermore, a recent study in glioma cells showed that inhibition of the Akt pathway strongly upregulated ceramide levels by inhibiting conversion of ceramide to complex sphingolipids due to reduction of ER to Golgi trafficking of ceramide (Giussani et al. *J Biol Chem* 284:5088-5096, 2009). Because ceramide in turn further inhibits Akt, this engages a vicious cycle that amplifies the apoptotic effect of SK1-I. Activation of JNK may also be due to inhibition of Akt following SK1-I treatment as several studies raised the intriguing possibility that the ability of Akt to inhibit JNK signaling is due to phosphorylation of specific targets in this pathway (Kim et al. *Mol Cell Biol* 21:893-901, 2001; and Barthwal et al. *J Biol Chem* 278:3897-3902, 2003).

Downregulation of SphK1, similar to SK1-I, causes a marked elevation in levels of ceramide (Maceyka et al. *J Biol Chem* 280:37118-37129, 2005; Pchejetski et al. *Cancer Res* 65:11667-11675, 2005; Taha et al. *FASEB J* 20:482-484, 2006; Berdyshev et al. *Cell Signal* 18:1779-1792, 2006). Consistent with the higher expression of SphK1 in GBM, ceramide levels are lower in human gliomas compared to surrounding brain tissue, and are inversely related to tumor progression and short patient survival (Riboni et al. *Glia* 39:105-113, 2002). Thus, actions of SphK1 might be related to its role in regulation of ceramide levels.

The existence of redundant survival pathways suggests that targeting a single dysregulated pathway may not be sufficient to eliminate tumors. Indeed, it has been suggested that effective GBM therapy may require combinations of inhibitors targeting multiple signaling pathways (Stommel et al. *Science* 318:287-290, 2007). The finding of the present invention that inhibiting SphK1 with SK1-I further enhanced glioblastoma cell lethality induced by inhibitors of other important signaling pathways that are frequently dysregulated in GBM may have implications for the design of protocols combining SphK1 inhibitors together with conventional anticancer agents or experimental therapeutics.

Supplementary Materials and Methods

Reagents. S1P was obtained from BIOMOL (Plymouth Meeting, Pa.). Serum and medium was from Biofluids (Rockville, Md.). EGF was from Life Technologies (Gaithersburg, Md.). Anti-phospho Akt (Ser473 and Thr308), anti-Akt, anti-phospho-ERK1/2 (Thr202/Tyr204), anti-phospho-ATF2 (Thr71), anti-phospho-JNK (Thr183/Tyr185) antibodies were from Cell Signaling (Beverly, Mass.) and anti-ERK2, anti-phospho-c-Jun (Ser63/73) and anti-clathrin heavy chain (CHC) antibodies were from Santa Cruz (Santa Cruz, Calif.). Rabbit polyclonal SphK1 antibodies were described previously (Hait et al. *J Biol Chem* 280:29462-29469, 2005). Horseradish peroxidase (HRP)-conjugated and fluorescently labeled secondary antibodies were from Jackson ImmunoResearch (West Grove, Pa.) and Molecular Probes (Eugene, Oreg.), respectively. Control and SphK1-specific siRNAs (Hait et al., ibid.) were obtained from Qiagen (Valencia, Calif.). WST-1 cell proliferation reagent and TUNEL kit for immunohistochemistry were from Roche Applied Science (Indianapolis, Ind.). SK1-I ((2R,3S,4E)-N-methyl-5-(4'-pentylphenyl)-2-aminopent-4-ene-1,3-diol, BML-258), was synthesized as the HCl salt by BIOMOL International (now Enzo Life Sciences International, Plymouth Meeting Pa.). SP600125 and SB202190 were from Sigma-Aldrich (St. Louis, Mo.), JNK peptide inhibitor 1 and the negative control peptide were from EMD Biosciences (San Diego, Calif.), and LY294002 and U0126 were from Cell Signaling Technology.

Downregulation of SphK1. U373-MG and LN229 cells were transfected with 100 nM control siRNA or siRNA against SphK1 (sequence targeted: GGGCAAGGCCTTGCAGCTC [SEQ ID NO:1]), using Dharmafect 1 reagent (Dharmacon, Chicago, Ill.) as described (Paugh et al. *FASEB J* 22:455-465, 2008).

SphK1 activity. SphK1 activity was determined exactly as described (Hait et al. *J Biol Chem* 280:29462-29469, 2005).

Western blotting. Cells were scraped in buffer containing 20 mM Tris-HCl, pH 7.5, 50 mM NaCl, 50 mM NaF, 30 mM $Na_4P_2O_7$, 20 mM 2-glycerophosphate, 1 mM $Na_3VO_4$, 5 mM EDTA, 2 mM EGTA, 0.5% SDS and protease inhibitor cocktail (1:200 dilution) and probe-sonicated. Equal amounts of protein determined with bicinchoninic acid (Pierce, Rockford, Ill.), were resolved by SDS-PAGE and transferred to nitrocellulose membranes. Blots were blocked with 5% non-fat dry milk in Tris-buffered saline containing 0.1% Triton X-100 (TBST) for 1 h at room temperature, and then incubated with primary antibodies (1:3,000 in 1% BSA) overnight, followed by the appropriate HRP-conjugated secondary antibodies (1:40,000 in 1% BSA). Immunocomplexes were visualized by enhanced chemiluminescence (Pierce).

Immunohistochemistry. Paraffin sections were dewaxed, rehydrated, incubated with proteinase K before permeabilization, and then stained with hematoxylin-eosin. Frozen sections were dried, fixed in formalin, and stained with antibodies against mouse CD-31 (BD Pharmingen, San Jose, Calif.), or rabbit antibodies against phospho-Akt (Ser473) (Cell Signaling) followed by immunohistochemistry with Alexa-488-conjugated species-specific secondary antibodies. Cryosections were air dried, permeabilized with 0.5% Triton X-100, and stained with a fluorescein TUNEL labeling kit (Roche Applied Sciences, Indianapolis, Ind.) followed by counterstaining with Hoechst. Sections were also stained with goat anti-human VEGF affinity-purified antibody (R&D), visualized with anti-goat horseradish peroxidase-diaminobenzidene staining kit (R&D) and counterstained with hematoxylin.

Immunocytochemistry and confocal microscopy. Cells were grown on 3-aminopropyl-triethoxysilane-treated 15 mm glass cover slips in 24 well plates. Following treatments, cells were washed with PBS, fixed with 3% paraformaldehyde for 10 min at room temperature, and blocked in TBST buffer containing 1% BSA. After washing, cells were incubated in the same buffer containing Alexa-conjugated phalloidin for 30 min, followed by 15 min incubation in 10 μg/ml of Hoechst 33342. For TUNEL assays, fixed cells were permeabilized with 0.5% TX-100 for 30 min, washed and incubated in TdT buffer supplemented with 250 μM $CoCl_2$, 20 units TdT (NEB, Ipswich, Mass.) and 1 nM fluorescein-12-dUTP (Roche) for 1 h at 37° C. Coverslips were washed with TBST, rinsed in water, air dried and mounted on glass slides with Cytoseal 60 polymer (Richard-Allan Scientific, Kalamazoo, Mich.). Images were collected on an LSM 510 laser confocal microscope (Zeiss, Thornwood, N.Y.) with a 100× oil immersion objective.

Cell proliferation and cell death assays. Cells were plated at 10,000 cells/well in 48-well plates and allowed to attach for 24 h. Cell proliferation was measured at the indicated times with WST-1 and absorbance was measured in a plate reader at 450 nm with background subtraction at 630 nm. Cell death was detected by trypan blue exclusion assays in which the percent of blue dye incorporating cells were determined using a light microscope and a hemacytometer as described (Yacoub et al. *Mol Cancer Ther* 7:314-329, 2008). Apoptotic cell death was measured by staining cell nuclei with the Hoechst dye bisbenzimide and apoptotic cells were identified by condensed, fragmented nuclear regions as described previously (Sankala et al. *Cancer Res* 67:10466-10474, 2007). A minimum of 300 cells was scored.

Colony formation assay. Cells were plated at a density of 1000 cells/well in a 12-well plate in DMEM containing 5% serum. After 8 h, SK1-I was added and 2 h later, the media was changed. After 10 days, cells were fixed in 4% paraformaldehyde and stained with crystal violet (0.05%). Colonies larger then 0.5 mm in diameter were counted.

Infection of cells with recombinant adenoviruses. Cells were plated at $3 \times 10^3$ per $cm^2$ and infected after 24 h (at a multiplicity of infection of 50) with a control empty vector virus (CMV) or adenoviruses expressing constitutively active (ca) Akt, dominant-negative (dn) Akt, caMEK1, dnMEK1, or Bcl-xL (Vector Biolabs, Philadelphia, Pa.).

Invasion and chemotaxis assays. Boyden chamber invasion assays were carried out essentially as described (Shida et al. *Cancer Res* 68:6569-6577, 2008).

Mass spectrometric analyses. Lipids were extracted and phosphorylated and unphosphorylated sphingoid bases, individual ceramide acyl chain species, as well as SK1-I and its metabolites were quantified by liquid chromatography, electrospray ionization-tandem mass spectrometry (LC-ESI-MS/MS) as described previously (Merrill et al. *Methods* 36:207-224, 2005).

Statistical analysis. Experiments were repeated at least three times with consistent results. For each experiment, data from triplicate samples were expressed as means±S.D. Statistics were performed by single factor ANOVA, and $p<0.05$ was considered significant. The Kaplan-Meier estimator was used to generate the survival curves and to estimate the median survival values. Differences between survival curves were compared using a log-rank test.

All patents, patent applications, patent publications, scientific articles and the like, cited or identified in this application, are hereby incorporated by reference in their entireties.

Many obvious variations will no doubt be suggested to those of ordinary skill in the art, in light of the above detailed description and examples of the present invention. It will be appreciated by those skilled in the art that any arrangement which is calculated to achieve the same purpose may be substituted for the specific embodiments shown. This application and invention are intended to cover any adaptations or variations of the present invention. All such variations are fully embraced by the scope and spirit of the invention as more particularly defined in the claims that now follow.

What is claimed is:

1. A method for treating neuropathic pain in a patient, comprising:
   administering to a patient in need of treatment for neuropathic pain a compound having the formula

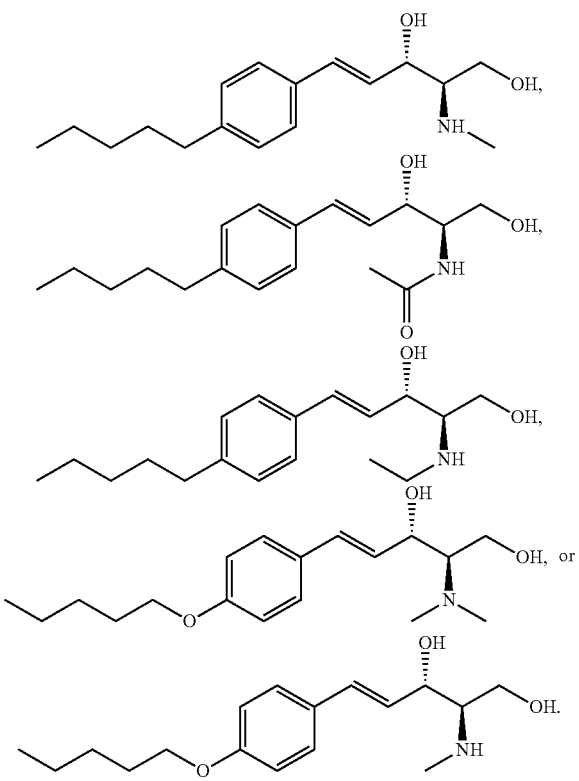

2. The method of claim 1, wherein the administering step comprises administering

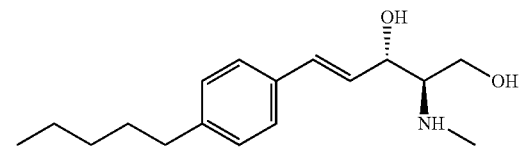 [SMILES: CCCCCc1ccc(/C=C/[C@H](O)[C@@H](CO)NC)cc1]

to the patient.

SEQUENCE LISTING

<160> NUMBER OF SEQ ID NOS: 1

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gggcaaggcc ttgcagctc                                                19

3. The method of claim 2, wherein the step of administering

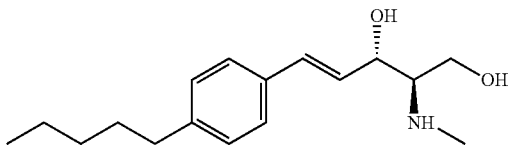 [SMILES: CCCCCc1ccc(/C=C/[C@H](O)[C@@H](CO)NC)cc1]

to the patient comprises administering

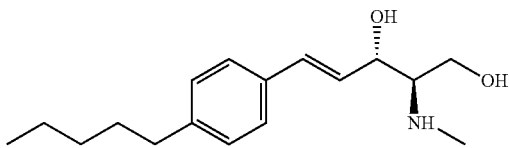 [SMILES: CCCCCc1ccc(/C=C/[C@H](O)[C@@H](CO)NC)cc1]

HCl to the patient.

4. A method for treating neuropathic pain in a patient, comprising:
administering to a patient in need of treatment for neuropathic pain a compound having the formula

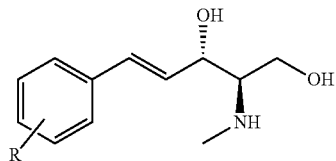

wherein R comprises a straight carbon chain, a branched carbon chain, a straight carbon chain comprising one or more heteroatoms, a branched carbon chain comprising one or more heteroatoms, a cyclic ring, a heterocyclic ring, an aromatic ring, a hetero-aromatic ring, or any combination of the foregoing.

5. The method of claim 4, wherein R is a straight carbon chain, a branched carbon chain, a straight carbon chain comprising one or more heteroatoms, a branched carbon chain comprising one or more heteroatoms, a cyclic ring, a heterocyclic ring, an aromatic ring, a hetero-aromatic ring, or any combination of the foregoing.

6. The method of claim 5, wherein R is a straight carbon chain, a branched carbon chain, a straight carbon chain comprising one or more heteroatoms, a branched carbon chain comprising one or more heteroatoms, a cyclic ring, a heterocyclic ring, an aromatic ring, or a hetero-aromatic ring.

7. The method of claim 6, wherein R is a straight carbon chain, a branched carbon chain, a straight carbon chain comprising one or more heteroatoms, or a branched carbon chain comprising one or more heteroatoms.

8. The method of claim 7, wherein R is a straight carbon chain or a branched carbon chain.

9. The method of claim 8, wherein R is a straight carbon chain.

10. A method for treating neuropathic pain in a patient, consisting essentially of:
administering

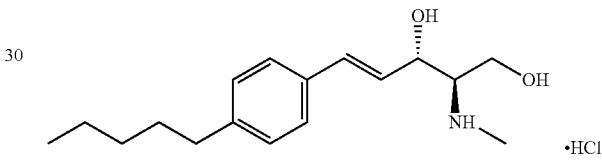

to the patient.

* * * * *